US009656978B2

(12) United States Patent
Griffin et al.

(10) Patent No.: US 9,656,978 B2
(45) Date of Patent: May 23, 2017

(54) ACYLPIPERAZINES AS INHIBITORS OF TRANSGLUTAMINASE AND THEIR USE IN MEDICINE

(71) Applicant: ASTON UNIVERSITY, Birmingham (GB)

(72) Inventors: Martin Griffin, Bleasby (GB); Daniel Rathbone, Conventry (GB); Leonas Eduard Badarau, Villenave D'Ornon (FR)

(73) Assignee: ASTON UNIVERSITY, Birmingham (GB)

( * ) Notice: Subject to any disclaimer, the term of this patent is extended or adjusted under 35 U.S.C. 154(b) by 0 days.

(21) Appl. No.: 14/431,472

(22) PCT Filed: Oct. 9, 2013

(86) PCT No.: PCT/GB2013/052631
§ 371 (c)(1),
(2) Date: Mar. 26, 2015

(87) PCT Pub. No.: WO2014/057266
PCT Pub. Date: Apr. 17, 2014

(65) Prior Publication Data
US 2015/0259310 A1 Sep. 17, 2015

(30) Foreign Application Priority Data

Oct. 9, 2012 (GB) ................................. 1218084.0

(51) Int. Cl.
| | | |
|---|---|---|
| *A61K 31/495* | (2006.01) | |
| *A61P 25/28* | (2006.01) | |
| *A61P 31/18* | (2006.01) | |
| *A61P 17/06* | (2006.01) | |
| *A61P 7/02* | (2006.01) | |
| *A61P 29/00* | (2006.01) | |
| *C07D 295/26* | (2006.01) | |
| *C07D 233/84* | (2006.01) | |
| *C07D 295/185* | (2006.01) | |
| *C07D 295/205* | (2006.01) | |

(52) U.S. Cl.
CPC ......... *C07D 295/26* (2013.01); *C07D 233/84* (2013.01); *C07D 295/185* (2013.01); *C07D 295/205* (2013.01)

(58) Field of Classification Search
CPC combination set(s) only.
See application file for complete search history.

(56) References Cited

U.S. PATENT DOCUMENTS

| | | | |
|---|---|---|---|
| 5,721,365 A | 2/1998 | Keefer | |
| 6,030,946 A | 2/2000 | Klaus | |
| 6,667,342 B1 | 12/2003 | Clarke | |
| 7,915,261 B2 * | 3/2011 | Ishii | ........................ A61K 31/44 514/253.12 |
| 2010/0160323 A1 * | 6/2010 | Bischoff | .............. C07D 209/88 514/235.8 |

FOREIGN PATENT DOCUMENTS

| | | |
|---|---|---|
| EP | 0411909 | 2/1991 |
| EP | 0771565 | 7/1997 |
| EP | 0838460 | 4/1998 |
| JP | H0288549 | 3/1990 |
| WO | 0107440 | 2/2001 |
| WO | 2004089470 | 10/2004 |
| WO | 2013022550 | 2/2013 |
| WO | 2014057266 | 4/2014 |

OTHER PUBLICATIONS

Kondo et al. "Design and synthesis of DPP-IV inhibitors lacking the electrophilic nitrile group," Bioorganic and Medicinal Chemistry, 2007, 1613-1631, 16(4).
PubChem Compound Accession No. CID 3291454 (2005).
PubChem Compound Accession No. CID 3254510 (2005).
PubChem Compound Accession No. CID 55477654 (2012).
PubChem Compound Accession No. CID 42658068 (2009).
PubChem Compound Accession No. CID 42658077 (2009).
Chemical Abstracts Service CAPLUS Database accession No. 1996: 708181, "Preparation of bisphosphonic acid derivatives as cysteine protease inhibitors" (1996) Compounds RN 183383-61-1.
PubChem Compound Accession No. CID 51135247 (2011).
PubChem Compound Accession No. CID 52522414 (2011).
PubChem Compound Accession No. CID 52522415 (2011).
Chemical Abstracts Service Database accession No. 1321660-27-8 (2011).
Chemical Abstracts Service Database accession No. 1276484-50-4 (2011).
Chemical Abstracts Service Database accession No. 1371966-00-5 (2012).
Chemical Abstracts Service Database accession No. 1331040-78-8 (2011).
Chemical Abstracts Service Database accession No. 1371000-53-1 (2012).
Chemical Abstracts Service Database accession No. 1214799-76-4 (2010).
Chemical Abstracts Service Database accession No. 338734-10-4 (2001).
Chemical Abstracts Service Database accession No. 338733-99-6 (2001).

(Continued)

*Primary Examiner* — Michael Barker
*Assistant Examiner* — Amanda L Aguirre
(74) *Attorney, Agent, or Firm* — Robert C. Netter, Jr.; Dann, Dorfman, Herrell & Skillman

(57) ABSTRACT

The present invention relates to novel compounds of Formula I capable of inhibiting tissue transglutaminase, and uses of the same in medicine. In particular, the invention provides compounds for use in the treatment of prevention of disease and conditions such as fibrosis (e.g. cystic fibrosis), scarring, neurodegenerative diseases (e.g. Alzheimer's disease, Huntington's disease and Parkinson's disease), autoimmune diseases (e.g. multiple sclerosis and coeliac disease), thrombosis, proliferative disorders (e.g. cancers), AIDS, psoriasis and inflammation (e.g. chronic inflammatory diseases).

21 Claims, 1 Drawing Sheet

(56) References Cited

OTHER PUBLICATIONS

Chemical Abstracts Service Database accession No. 337508-08-04 (2001).
Watts et al., "Structure-activity relationship analysis of the selective inhibition of transglutaminase 2 by dihydroisoxazoles," Journal of Medicinal Chemistry, 2006, 7493-7501, 49(25).
Siegel et al., "Transglutaminase 2 inhibitors and their therapeutic role in disease states," Pharmacology and Therapeutics, 2007, 232-245, 115(2).

* cited by examiner

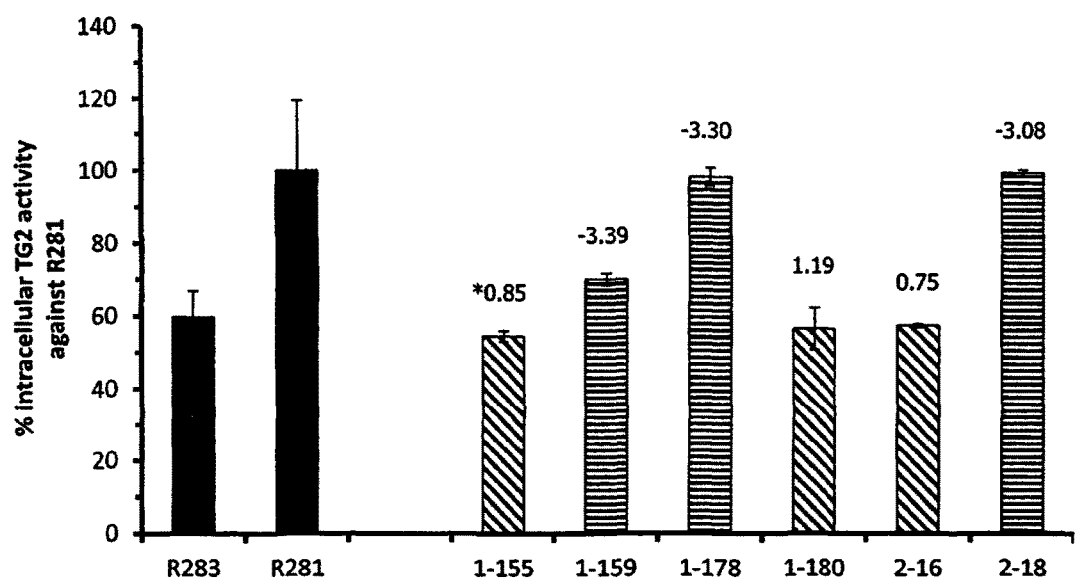
* cLogP values, weighted averages of three methods calculated using MarvinView 5.11.4.

ACYLPIPERAZINES AS INHIBITORS OF TRANSGLUTAMINASE AND THEIR USE IN MEDICINE

This application is a §371 application of PCT/GB2013/052631, filed Oct. 9, 2013, which in turn claims priority to GB Application 1218084.0, filed Oct. 9, 2012. The entire disclosure of each of the foregoing applications is incorporated by reference herein.

FIELD OF THE INVENTION

The present invention provides novel compounds with transglutaminase inhibitory activity, and uses thereof in medicine.

INTRODUCTION

Transglutaminases (TGs or TGases) are a group of enzymes able to modify proteins by mediating an acyl-transfer reaction between the γ-carboxamide group of peptide-bound glutamine and a primary amine. The result of this reaction is post-translational modification, either through protein crosslinking, if the amine is the ε-amino group of peptide-bound lysine, or modification of the peptide glutamine by crosslinking to a primary amine such as a polyamine. Under certain conditions and in the absence of a suitable primary amine, the deamidation of peptide bound glutamine can also occur. Because of their ability to cross-link proteins into high molecular weight protein aggregates TGs have been termed as "Nature's Biological glues" (Griffin et al., 2002). TGs are found widely in nature, but in mammals their enzymatic activity is $Ca^{2+}$-dependent, and other factors including GTP/GDP can also affect the activity of some of the mammalian TGs (Verderio et al., 2004). Not all of the eight active members (TG1-7 and factor XIII) of the mammalian TG family have been fully characterized (Collighan and Griffin, 2009). Another member of this family, band 4.2, is catalytically inactive and is mainly associated with the regulation of the erythrocyte cytoskeleton. TG2 (tissue transglutaminase, TG2M, tTG) is probably the most ubiquitous member of the mammalian TG family which is found both in the intra- and extra-cellular environment. In addition to its transamidating, GTPase and ATPase activity (Nakaoka et al., 1994), further novel activities have recently been reported for TG2 e.g. the protein disulfide isomerase (PDI) (Hasegawa et al., 2003) and protein kinase activities (Mishra and Murphy, 2004), thus further extending the potential physiological and pathological importance of this diverse group of enzymes. Abnormal levels of transglutaminase particularly TG2 and/or activity have been observed in many disease states, like celiac sprue, neurodegenerative diseases (Alzheimer, Parkinson, Huntington disease), fibrosis, cataract, cancer metastasis, and the list is certainly not intended to be exhaustive. Moreover, proof of concept studies using either TG2−/− animal models (Bailey and Johnson, 2005; Mastroberardino et al., 2002) or inhibitor studies (Huang et al., 2009; Johnson et al., 2008) have shown the enzyme to be a potential novel candidate for therapeutic intervention.

Due to its implication in a wide variety of biological processes and pathologies, developing chemicals tools to further investigate TG2s multifunctional roles is an active research area. Most of the inhibitors developed so far target the enzyme's catalytic site, but there are also reports of small molecules competing for the TG2 cofactor binding site. Depending on their ability to reach and react with the catalytic cysteine residue (CYS277 in case of hTG2), they can further be divided into reversible and irreversible inhibitors. Peptidic inhibitors bearing various electrophilic moieties (e.g. chloroacetamides (Pardin et al., 2006), α,β-unsaturated amides (Pardin et al., 2006), maleimides (Halim et al., 2007), sulfonium methyl ketones (Griffin et al., 2008), dihydroisoxazoles (Dafik and Khosla, 2011), cinnamoyl derivatives (Pardin et al., 2008a; Pardin et al., 2008b), oxindoles (Klock et al., 2011), sulfonamidopiperazines (Prime et al., 2012) are recent examples of such derivatives. The resolved TG2 structures co-crystallized either with irreversible inhibitors (Lindemann et al., 2012; Pinkas et al., 2007) or nucleotides (Han et al., 2010; Liu et al., 2002), revealed the huge conformational change of the enzyme when passing from the inactive to the active state, and will certainly enhance the design of more potent inhibitors in the future.

The present invention seeks to provide novel compounds which inhibit transglutaminase activity, for use in medicine.

SUMMARY OF THE INVENTION

This invention stems from the discovery that a new class of peptidomimetic derivatives, comprising a piperazine scaffold, are capable of interacting with transglutaminase enzymes, such as tissue transglutaminase, and inhibiting their activity.

According to a first aspect of the invention, there is provided a compound according to Formula I

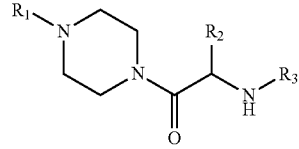

Formula I wherein $R_1$ is selected from the group consisting of $R_4C(O)$—, $R_5OC(O)$— and $R_6S(O)_2$— (wherein '-' denotes the bond between the $R_1$ substituent group and the nitrogen of the piperazine ring)

wherein $R_4$ is a lower alkyl group $R_5$ and $R_6$ are selected from the group consisting of heterocyclic groups, aralkyl groups and lower alkyl groups $R_2$ is a side chain of an amino acid; and $R_3$ is selected from the group consisting of —C(O)$R_7$ and —S(O)$_2$CHCH$_2$ (wherein '-' denotes the bond between the $R_3$ substituent group and the nitrogen of the amino acid moiety within the compound of the invention)

wherein $R_7$ is selected from the group consisting of alkyl halide, alkylene dialkyl sulfonium, alkylenethioimidazolium, lower alkyl, lower alkenyl, epoxide and alkylene dihydroisoxazole groups and pharmaceutically and/or veterinarily acceptable derivatives thereof.

The compounds of the invention are inhibitors of transglutaminase enzymes, of which eight are currently known (TG1-7 and factor XIII). Thus, by "transglutaminase" we include enzymes as defined in accordance with Enzyme Commission System of Classification 2.3.2.13.

In a preferred embodiment, the transglutaminase enzyme is tissue transglutaminase.

In an alternative embodiment, the transglutaminase enzyme may be factor XIII.

The transglutaminase enzyme, e.g. tissue transglutaminase, is preferably human.

By "transglutaminase inhibitor" we include any compound that inhibits, in part or in whole, the transamidating activity of a transglutaminase enzyme (preferably in vivo).

In one embodiment, the compounds of the invention are irreversible inhibitors of tissue transglutaminase.

In one embodiment, the compounds of the invention are selective inhibitors of tissue transglutaminase. By "selective", we mean that the compound inhibits tissue transglutaminase (preferably human TG2) to a greater extent than it inhibits other transglutaminase enzymes, such as Factor XIII, TG1 and TG3. Advantageously, the compound exhibits an IC50 for tissue transglutaminase (preferably human TG2) which is at least one order of magnitude lower than its IC50 for other transglutaminase enzymes, such as Factor XIII, TG1 and TG3 (see Example 2).

The term "lower alkyl" is intended to include linear or branched, cyclic or acyclic, $C_1$-$C_{20}$ alkyl, which is saturated. Lower alkyl groups which $R_2$, $R_3$, $R_4$, $R_5$ and/or $R_6$ may include $C_1$-$C_{10}$ alkyl, $C_1$-$C_5$ alkyl, $C_1$-$C_4$ alkyl, $C_1$-$C_3$ alkyl, $C_1$-$C_2$ alkyl, $C_2$-$C_5$ alkyl, $C_3$-$C_5$ alkyl, $C_4$-$C_5$ alkyl, $C_2$-$C_4$ alkyl, $C_2$-$C_3$ alkyl and $C_3$-$C_4$ alkyl. Preferred lower alkyl groups which $R_2$, $R_3$, $R_4$, $R_5$ and/or $R_6$ may represent include $C_1$, $C_2$, $C_3$, $C_4$ and $C_5$ alkyl.

It will be appreciated that the term "lower alkyl" encompasses cycloalkyl groups, for example $C_6$-$C_{20}$ cycloalkyl (carbocyclic) groups, including single and multiple (fused) rings, as well as planar and non-planar ring structures.

In one embodiment, the "lower alkyl" group is a $C_6$-$C_{10}$ cycloalkyl group.

The term "alkylene" is to be construed accordingly.

The term 'lower alkyl halide' is also to be construed accordingly.

The term "lower alkenyl" is intended to include linear or branched, cyclic or acyclic, $C_2$-$C_{20}$ alkenyl.

The term "lower alkenyl" also includes both the cis and trans geometric isomers. Lower alkenyl groups which $R_3$ may represent include $C_2$-$C_{10}$ alkenyl, $C_2$-$C_9$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl and $C_3$-$C_4$ alkenyl. Preferred lower alkenyl groups which $R_3$ may represent include $C_2$, $C_3$, $C_4$ and $C_5$ alkenyl.

In the compounds of the invention, $R_1$ is selected from the group consisting of $R_4C(O)$—, $R_5OC(O)$— and $R_6S(O)_2$— (wherein '-' represents the bond to the nitrogen of the piperazine ring to which $R_1$ is attached), wherein $R_4$ is a lower alkyl group and $R_5$ and $R_6$ are selected from the group consisting of heterocyclic groups, aralkyl groups and lower alkyl groups.

Thus, in one embodiment, $R_1$ is $R_4C(O)$—.

In one embodiment, $R_4$ is a cycloalkyl group (such as a planar or fused ring comprising six to twenty carbons).

For example, $R_4$ may be an adamantyl substituent group of the following structure:

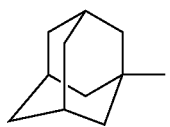

(wherein the dashed line represents the bond to the carbon of the carbonyl group of the compound of Formula I to which $R_4$ is attached).

In an alternative embodiment, $R_1$ is $R_5OC(O)$—, wherein $R_5$ is a heterocyclic group, aralkyl group or lower alkyl group.

By "heterocyclic" we include carbon ring structures comprising at least one non-carbon atom, such as nitrogen or oxygen. In one embodiment, the heterocyclic group is a single or multi-ring structure (planar or non-planar) comprising four to nine carbon atoms together with at least one nitrogen atom (such as a quinolyl ring).

By "aralkyl" we include aryl groups joined to the piperazine ring of the compound of the invention via a saturated, acyclic lower alkylene group. The term "aryl" includes six to ten-membered carbocyclic aromatic groups, such as phenyl and naphthyl, which groups are optionally substituted by one or more substituents selected from fluoro, cyano, nitro, lower alkyl (i.e. alkaryl), OR, C(O)R, C(O)OR, C(O)NRR' and NRR' (were R and R' represent lower alkyl groups).

Thus, $R_5$ may comprise or consist of a phenyl or naphthyl group linked to the ester moiety of $R_5OC(O)$— by a straight chain $C_{1-6}$ alkylene group (such as a methylene or ethylene group).

In one embodiment, the phenyl or naphthyl group is substituted with one or more ester substituent groups of formula $R_8OOC$—, wherein $R_8$ is a lower alkyl group (such as a methyl, ethyl, propyl or butyl group), For example, $R_5$ may be selected from the group consisting of

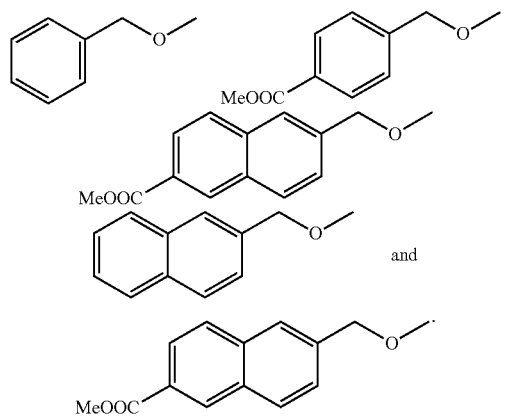

and (wherein the dashed line represents the bond to the carbon of the carbonyl group of the compound of Formula I to which $R_1$ is attached).

In a further embodiment, $R_5$ is a lower alkyl group, which may be linear or branched, cyclic or acyclic.

Thus, $R_5$ may be —$CR_9(R_{10})(R_{11})$, wherein $R_9$, $R_{10}$ and $R_{11}$ are each independently methyl or ethyl groups.

For example, $R_1$ may be:

(wherein the dashed line represents the bond to the carbon of the carbonyl group of the compound of Formula I to which $R_1$ is attached).

In a further embodiment, $R_5$ comprises a cycloalkyl group, such as an adamantyl ring.

For example, $R_5$ may be:

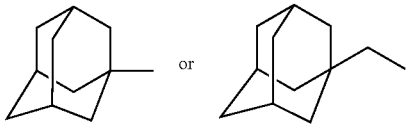

(wherein the dashed line represents the bond to the carbon of the carbonyl group of the compound of Formula I to which $R_5$ is attached).

In a further embodiment, $R_1$ is $R_6S(O)_2$—, wherein $R_6$ is a heterocyclic group, aralkyl group or lower alkyl group.

For example, $R_6$ may be a heterocyclic group, an aralkyl group or a lower alkyl group (as disclosed above in relation to $R_5$).

In one embodiment, $R_6$ comprises or consists of a cycloalkyl group, such as a phenyl or naphthyl group.

Thus, one embodiment, $R_1$ may be a dansyl group, such as

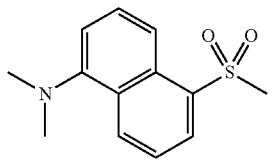

(wherein the dashed line represents the bond to the nitrogen atom of the piperazine of the compound of Formula I to which $R_1$ is attached).

The compounds of the invention comprise a central amino acid moiety, of which $R_2$ constitutes the amino acid side chain.

Thus, $R_2$ may be a side chain of a naturally-occurring, proteinogenic amino acid, for example selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

However, in one embodiment, $R_2$ is not aromatic. For example, in one embodiment, $R_2$ is not the side chain of phenylalanine and/or tyrosine.

It will be appreciated that the carbon to which $R_2$ is attached may exhibit stereoisomerism. For example, this portion of the compound may correspond to an L-amino acid (such as L-alanine). Alternatively, this portion of the compound may correspond to a D-amino acid (such as D-alanine).

In one embodiment, $R_2$ is selected from the group consisting of hydrogen (i.e. the 'side chain' of glycine) and alkyl groups (i.e. the side chains of alanine, isoleucine, leucine and valine). For example, $R_2$ may be a methyl group (i.e. the amino acid core is alanine).

$R_3$ is a substituent group attached to the amino acid core of the compound of the invention via the nitrogen of the amino acid moiety thereof.

$R_3$ is selected from the group consisting of —C(O)$R_7$ and —S(O)$_2$CHCH$_2$, wherein
$R_7$ is selected from the group consisting of alkyl halide, alkylene dialkyl sulfonium, alkylenethioimidazolium, lower alkyl, lower alkenyl, epoxide and alkylene dihydroisoxazole groups Thus, in one embodiment, $R_3$ is —C(O)$R_7$.

In one embodiment, $R_7$ is a lower alkyl halide group.

By "halide", we include fluoride (F$^-$), chloride (Cl$^-$), bromide (Br$^-$) and iodide (I$^-$).

Thus, the lower alkyl may be linear or branched $C_1$-$C_5$ alkyl and the halide may be bromide or chloride.

For example, $R_7$ may be

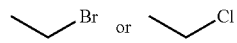

(wherein the dashed line represents the bond to the carbon of the carbonyl group to which $R_7$ is attached).

In an alternative embodiment, $R_7$ is an alkylene dialkyl sulfonium group, wherein the alkylene and alkyl groups are lower alkylene and alkyl, respectively (such as linear or branched $C_1$-$C_5$ alkylene or alkyl)

For example, $R_7$ may be

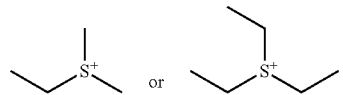

(wherein the dashed line represents the bond to the carbon of the carbonyl group to which $R_7$ is attached).

In a further alternative embodiment, $R_7$ is an alkylenethioimidazolium group, which may be substituted with one or more lower alkyl groups (such as linear or branched $C_1$-$C_5$ alkyl).

For example, $R_7$ may be

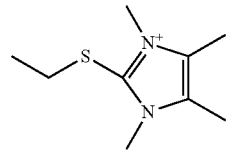

(wherein the dashed line represents the bond to the carbon of the carbonyl group to which $R_7$ is attached).

In a further alternative embodiment, $R_7$ is a lower alkyl group.

For example, $R_3$ may be —CH$_3$ (wherein '-' represents the bond to the carbon of the carbonyl group to which $R_7$ is attached).

In a further alternative embodiment, $R_7$ is a lower alkenyl group.

For example, $R_7$ may be

(wherein the dashed line represents the bond to the carbon of the carbonyl group to which $R_7$ is attached).

In a further alternative embodiment, $R_7$ is an epoxide group.

In a further alternative embodiment, $R_7$ is an alkylene 3-halo-4,5-dihydroisoxazole group (e.g. a methylene 3-bromo-4,5-dihydroisoxazole group).

In a further alternative embodiment, $R_3$ is —S(O)$_2$CHCH$_2$ (wherein '-' represents the bond to the nitrogen of the compound of the invention to which $R_3$ is attached).

Thus, $R_3$ forms a vinyl sulfonamide group (together with the —NH— moiety of the compound of the invention to which it is attached).

It will be appreciated that the various compounds of the invention may inhibit a transglutaminase enzyme with different potency.

In a preferred embodiment, the compound exhibits an IC50 for human tissue transglutaminase of less than 100 µM, for example less than 50 µM, 40 µM, 30 µM, 20 µM, 10 µM, 5 µM, 4 µM, 3 µM, 2 µM or less than 1 µM (see Example 2 for methodology).

Exemplary compounds of the invention are shown in Tables 1 to 3 (see Example 2 below).

However, in one embodiment, the compound is not EB 1-34, EB 1-45, EB 1-104, EB 1-105, EB 1-127, EB 1-131, EB 1-126 or EB 1-130.

It will be appreciated by persons skilled in the art that pharmaceutically, and/or veterinarily, acceptable derivatives of the compounds of Formula I, such as salts and solvates, are also included within the scope of the invention. Salts which may be mentioned include: acid addition salts, for example, salts formed with inorganic acids such as hydrochloric, hydrobromic, sulfuric and phosphoric acid, with carboxylic acids or with organo-sulfonic acids; base addition salts; metal salts formed with bases, for example, the sodium and potassium salts.

Thus, the compounds of formula I may be counterbalanced by counter-anions. Exemplary counter-anions include, but are not limited to, halides (e.g. fluoride, chloride and bromide), sulfates (e.g. decylsulfate), nitrates, perchlorates, sulfonates (e.g. methane-sulfonate) and trifluoroacetate. Other suitable counter-anions will be well known to persons skilled in the art.

In one embodiment, the compound is a bromide salt.

It will be further appreciated by skilled persons that the compounds of Formula I may exhibit tautomerism. All tautomeric forms and mixtures thereof are included within the scope of the invention.

Compounds of Formula I may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

A second aspect of the invention provides a pharmaceutical formulation comprising a compound according to the first aspect of the invention and a pharmaceutically acceptable excipient, carrier or diluent.

The compounds may be formulated at various concentrations, depending on the efficacy of the particular compound being used. Preferably, the composition comprises the compound at a concentration of between 1 nM and 1 M, for example between 0.1 µM and 1 mM, 1 µM and 100 µM, between 5 µM and 50 µM, between 10 µM and 50 µM, between 20 µM and 40 µM and optionally about 30 µM. For ex vivo and in vitro applications, compositions may comprise a lower concentration of a modified osteopontin polypeptide, for example between 0.0025 µM and 1 µM.

The excipient, carrier or diluent will be selected with regard to the intended route of administration and standard pharmaceutical practice (for example, see Remington: The Science and Practice of Pharmacy, 19$^{th}$ edition, 1995, Ed. Alfonso Gennaro, Mack Publishing Company, Pennsylvania, USA, which is incorporated herein by reference).

By "pharmaceutically acceptable" is included that the excipient, carrier or diluent is non-toxic, sterile and pyrogen free.

Suitable pharmaceutical carriers are well known in the art of pharmacy. The carrier(s) must be "acceptable" in the sense of being compatible with the compound of the invention and not deleterious to the recipients thereof. Typically, the carriers will be water or saline which will be sterile and pyrogen free; however, other acceptable carriers may be used. Thus, "pharmaceutically acceptable carrier" and "pharmaceutically acceptable excipient" includes any compound(s) used in forming a part of the formulation that is intended to act merely as a carrier, i.e., not intended to have biological activity itself. The pharmaceutically acceptable carrier or excipient is generally safe, non-toxic, and neither biologically nor otherwise undesirable. A pharmaceutically acceptable carrier or excipient as used herein includes both one and more than one such carrier or excipient.

The excipient may be one or more of carbohydrates, polymers, lipids and minerals. Examples of carbohydrates include lactose, sucrose, mannitol, and cyclodextrines, which are added to the composition, e.g. for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylene-glycol/polyethylene oxide, polyethyleneoxide/polypropylene oxide copolymers, polyvinyl-lalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The term "diluent" is intended to mean an aqueous or non-aqueous solution with the purpose of diluting the peptide in the pharmaceutical preparation. The diluent may be one or more of saline, water, polyethylene glycol, propylene glycol, ethanol or oils (such as safflower oil, corn oil, peanut oil, cottonseed oil or sesame oil).

The diluent may also function as a buffer. The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The formulations according to the second aspect of the invention may conveniently be presented in unit dosage form and may be prepared by any of the methods well known in the art of pharmacy. Such methods include the step of bringing into association the active ingredient (i.e. a compound according to the first aspect of the invention) with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. It will be appreciated by those skilled in the art that the compounds for oral administration should preferably be formulated so as to be protected in the gut and to permit bioadsorption.

Preferred unit dosage formulations are those containing a daily dose or unit, daily sub-dose or an appropriate fraction thereof, of an active ingredient.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For treatment of diseases and conditions of the eye, the compound may be formulated in accordance with routine procedures as a pharmaceutical composition adapted for application to the eye. Thus, the pharmaceutical composition may be for topical ophthalmic use, for example aqueous eye drops, oily eye drops, eye ointments, eye lotions, ocuserts, hydrogel contact lenses, collagen shields and ophthalmic rods.

Topical compositions for the eye will typically have a pH in the range of 4.5 to 8.0. The ophthalmic compositions must also be formulated to have osmotic values that are compatible with the aqueous humor of the eye and ophthalmic tissues. Such osmotic values will generally be in the range of from about 200 to about 400 milliosmoles per kilogram of water ("mOsm/kg"), but will preferably be about 300 mOsm/kg.

In yet another embodiment, the TGase inhibitor compounds as described herein can be delivered in a controlled release system. For example, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989); the disclosures of which are incorporated by reference).

In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989); the disclosures of which are incorporated by reference).

It will be appreciated by persons skilled in the art that the compounds of the invention may comprise one or more additional active agents, such as anti-inflammatory agents, local anaesthetics and anti-biotic agents.

A third aspect of the invention provides a method of making a compound according to the first aspect of the invention comprising the following steps:
(a) synthesis of a p-nitrophenylcarbonate;
(b) piperazine alkylation of the p-nitrophenylcarbonate to produce a piperazine carboxylate;
(c) peptide coupling of the piperazine carboxylate; and
(d) carbamate deprotection of the product of step (c).

In one embodiment, the method further comprises step (e) of acrylamide derivatisation of the product of step (d).

In an alternative embodiment, the method further comprises step (e) of acetylation of the product of step (d).

In an alternative embodiment, the method further comprises step (e) of producing a dialkylsulfonium salt of the product of step (d).

In an alternative embodiment, the method further comprises step (e) of producing a vinyl sulfonamide of the product of step (d).

Further details of suitable synthesis routes for producing the compounds of the invention are provided in Example 1.

A fourth aspect of the invention provides a compound according to the first aspect of the invention for use in medicine.

A fifth aspect of the invention provides a compound according to the first aspect of the invention for use in the treatment or prevention of a disease or condition which is responsive to treatment with a transglutaminase inhibitor.

For example, the disease or condition may be responsive to treatment with an inhibitor of tissue transglutaminase (TG2).

In one embodiment, the disease or condition is responsive to treatment with an angiogenesis inhibitor. Thus, the compounds of the invention may be used to inhibit angiogenesis, especially pathological angiogenesis (i.e. the formulation of new vasculature associated with a disease or disorder; see Chung & Ferrera, 2011, *Ann. Rev. Cell Dev. Biol.* 27:563-584, the disclosures of which are incorporated by reference).

By "inhibiting angiogenesis" we mean that administration of the compound is capable of reducing, at least in part, the formation of new blood vessels in vivo. Thus, the compound may inhibit angiogenesis in vivo by at least 10% compared to the level of angiogenesis in the absence of the compound, for example by at least 20%, 30%, 40%, 50%, 60%, 70%, 80%, 90% or more. It will be appreciated that inhibition may require repeated (i.e. chronic) administration of the compound.

In a further embodiment, the disease or condition is selected from the group consisting of fibrosis (such as cystic fibrosis), scarring, neurodegenerative diseases (such as Alzheimer's disease, Huntington's disease and Parkinson's disease), autoimmune diseases (such as multiple sclerosis and coeliac disease), thrombosis, proliferative disorders (such as cancers), AIDS, psoriasis and inflammation (such as a chronic inflammatory disease).

For example, the disease or condition may be a fibrosis (such as cystic fibrosis).

Alternatively, the disease or condition may be a neurodegenerative disease (such as Alzheimer's disease, Huntington's disease or Parkinson's disease), In a further alternative embodiment, the disease or condition is an autoimmune disease (such as multiple sclerosis or coeliac disease).

In one embodiment, the disease or condition is associated with pathological angiogenesis. By "disease or disorder associated with pathological angiogenesis", we mean a disease or disorder in which abnormal or otherwise undesirable angiogenesis occurs, such that partial or complete inhibition of angiogenesis provides a beneficial effect to the patient (e.g. alleviates one or more symptoms and/or slows or prevents progression of the disease or disorder).

For example, the disease or condition may be selected from the group consisting of hemangiomas, psoriasis, Kaposi's sarcoma, ocular neovascularisation, rheumatoid arthritis, endometriosis, atherosclerosis and tumour growth and metastasis.

In one embodiment, the disease or condition may be a cancer.

For example, the cancer may be associated with solid tumours (such as prostate cancer, breast cancer, lung cancer, colorectal cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer, and sarcomas).

In a further embodiment, the disease or condition is of the eye, such as a disease or disorder of the retina and/or choroid.

Thus, the disease or condition may be a retinopathy.

For example, the disease or condition may be selected from the group consisting of diabetic retinopathy, age-related macular degeneration, retinopathy of prematurity, central retinal vein occlusion, sickle cell retinopathy, branch and central retinal vein occlusion and retinal trauma.

Alternatively, the disease or condition may be selected from the group consisting of chronic inflammation or infection (e.g. HSV infection of the ocular surface resulting in blood vessel formation), corneal scarring, wound repair, pterygium and neovascular glaucoma (i.e. growth of blood vessels on iris and into anterior chamber angle; robeosis iridis).

In a further embodiment, the disease or condition may be responsive to treatment with an inhibitor of factor XIII. For example, the disease or condition may be associated with the formation of fibrin clots.

A related, fifth aspect of the invention provides the use of a compound according to the first aspect of the invention in the preparation of a medicament for the treatment or prevention of a disease or condition which is responsive to treatment with an inhibitor of a transglutaminase (such as tissue transglutaminase or factor XIII).

Suitable diseases and conditions for which the compounds may be used are identified above in relation to the fourth aspect of the invention.

For example, the disease or condition may be selected from the group consisting of fibrosis (such as cystic fibrosis), scarring, neurodegenerative diseases (such as Alzheimer's disease, Huntington's disease and Parkinson's disease), autoimmune diseases (such as multiple sclerosis and coeliac disease), thrombosis, proliferative disorders (such as cancers), AIDS, psoriasis and inflammation (such as a chronic inflammatory disease).

A related, sixth aspect of the invention provides a method of treating a subject in need of treatment with a transglutaminase inhibitor comprising administering to said subject a compound according to the first aspect of the invention or a pharmaceutical formulation according to the second aspect of the invention.

It will be appreciated that the compound should be administered in a therapeutically effective amount to inhibit transglutaminase activity (at least in part). A 'therapeutically effective amount', or 'effective amount', or 'therapeutically effective', as used herein, refers to that amount which provides a therapeutic effect for a given condition and administration regimen (via an inhibition of transglutaminase activity). This is a predetermined quantity of the compound of the invention calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the subject. Alternatively, a therapeutically effective amount is sufficient to cause an improvement in a clinically significant condition in a subject. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

Suitable diseases and conditions for which the compounds may be used are identified above in relation to the fourth aspect of the invention.

Preferably, the compound according to the first aspect of the invention or a pharmaceutical formulation according to the second aspect of the invention is administered in an amount sufficient to inhibit, at least in part, tTGase-mediated protein modification (i.e. cross-linking). More preferably, the compound or formulation is administered in an amount sufficient to inhibit tTGase-mediated protein cross-linking by at least 10%, for example, at least 20%, 30%, 40%, 50%, 60%, 70%, 80%, 90% or 95%. Most preferably, the compound or formulation is administered in an amount sufficient to inhibit completely tTGase-mediated protein cross-linking.

TGase-mediated protein modification may be measured by methods known in the art. For example, detection of the isodipeptide ε(γ-glutamyl)lysine in body fluids can be used as an indirect measure of the frequency of crosslinking in diseases which involve this protein cross link. Hence, a reduction of the isodipeptide in the body fluid provides an indirect measure of reduced protein crosslinking (see Nemes et aL, 2002, *Minerva Biotechnology* 14, 183).

Alternatively, a tissue biopsy may be taken and analysed, for example by ion exchange or reversed phase HPLC after proteolytic digestion of the material (Griffin & Wilson, 1984, *Mol. Cell Biochem.* 58:37-49), or by staining biopsy sections and analysing by immunohistochemistry (Skill et al., 2001, 81:705-716).

In a further embodiment, the compound or formulation is administered in an amount sufficient to inhibit, at least in part, angiogenesis.

For example, the subject may have or be at risk of developing a disease or condition selected from the group consisting of fibrosis (such as cystic fibrosis), scarring, neurodegenerative diseases (such as Alzheimer's disease, Huntington's disease and Parkinson's disease), autoimmune diseases (such as multiple sclerosis and coeliac disease), thrombosis, proliferative disorders (such as cancers), AIDS, psoriasis and inflammation (such as a chronic inflammatory disease).

It will be appreciated by those skilled in the art that treatment may be prophylactic and/or therapeutic. For example, the compounds and formulations of the invention may be used to slow and/or to prevent the onset of a disease/disorder in the subject being treated. Alternatively, or in addition, the compounds and formulations of the invention may be used to reduce or eradicate the symptoms of a disease/disorder in the subject being treated.

It will be further appreciated by those skilled in the art that the compound or formulation of the first and second aspects of the invention, respectively, may be administered by any route known or developed in the art. For example, the compound or formulation may be administered by parenteral injection (e.g. intravenous, subcutaneous or intramuscular), orally or topically.

In one embodiment, the compound or formulation is administered systemically, for example intravenously. Alternatively, the compound or formulation is administered topically, e.g. at or near a target site where TGase-mediated protein modification is to be inhibited.

Treatment with a compound or formulation according to the invention may consist of a single dose or a plurality of doses over a period of time. Advantageously, the compound or formulation is administered repeatedly.

Compounds and formulations of the invention may also be administered by a surgically implanted device that releases the compound or formulation directly to the required site, for example in the vicinity of a solid tumour.

It will be appreciated by persons skilled in the art that the compounds of the invention may be used for the treatment of any mammal. Preferably, the subject is human. Alternatively, the subject may be a dog, cat, horse, or other domestic or farm mammalian animal.

A further aspect of the invention provides a method for preventing or treating rejection of a transplanted organ comprising contacting the organ with a compound according to the first aspect of the invention or a formulation according to the second aspect of the invention. Thus, the invention provides the use of a compound according to the first aspect of the invention in the preparation of a medicament for preventing or treating rejection of a transplanted organ.

In one embodiment, the organ is a heart, lung, kidney or liver.

Thus, the organ may be a kidney. Kidneys that are to be transplanted often show some upregulation of tissue transglutaminase and possibly other transglutaminases. Moreover, kidneys which are rejected after transplantation often exhibit excessive scarring and upregulation of transglutaminase activity and crosslinking (Abo-Zenah et al., 2001, *J. Am. Soc. Nephrol.* 12, 4454A). Such tissue degeneration and subsequent organ rejection may be prevented by treating the kidney (or other organ) with a transglutaminase inhibitor.

It will be appreciated that the compound or formulation may be delivered before, during and/or after transplantation of the organ. Thus, in one embodiment, the organ is treated prior to transplantation, for example by perfusing and/or bathing with a solution containing a compound according to the first aspect of the invention.

In an alternative embodiment, the organ is treated during and/or after transplantation into a patient. Advantageously, the compound or formulation is delivered at or near the site of the transplant, for example by local administration.

Preferred, non-limiting examples which embody certain aspects of the invention will now be described with reference to the following FIGURES.

FIG. 1 shows the effect of exemplary TGase inhibitor compounds of the invention on intracellular tissue transglutaminase (TG2) activity. Three of the test compounds comprised an acrylamide-based $R_3$ "warhead" group (1-155, 1-180 and 2-16) and three of the test compounds comprised a sulphonamide-based $R_3$ "warhead" group (1-159, 1-178 and 2-18).

EXAMPLES

Example 1—Synthesis of Exemplary Compounds of the Invention

Analytical Methodology

The infrared (IR) spectra were recorded on a Thermo Scientific Nicolet iS5 FT-IR spectrometer equipped with an ID5 Diamond ATR accessory. Signal intensities were abbreviated as follows: weak (w), medium (m) and strong(s).

$^1$H NMR and $^{13}$C NMR were recorded with Bruker Avance DPX250 (at 250.131 MHz and 62.895 MHz, respectively) in $CDCl_3$ and DMSO, using tetramethylsilane (TMS) as an internal standard. Chemical shifts are reported in parts per million (ppm) and the coupling constants are reported in units of Hertz [Hz]. Multiplicities were abbreviated as follows: singlet (s), doublet (d), triplet (t), quartet (q), pentuplet (p), sextet (sx), septet (sp), apparent singlet (as), apparent doublet (ad), apparent triplet (at)

Low-resolution mass spectra (MS) were recorded with a Waters—LCT Premier. High resolution mass spectra (HRMS) were recorded with a Thermo Fischer Scientific LTQ Orbitrap XL at EPSRC National Mass Spectrometry Centre, Swansea (UK).

Melting points were recorded using a Reichert-Jung Thermo Galen—Hot Stage Microscope equipped with a Pt 100/RTD temperature sensor.

Flash chromatography was performed on Merck 40-70 nM (230-400 mesh) silica gel under nitrogen pressure. Thin-layer chromatography (TLC) was carried out on Merck silica gel 60 F254 precoated plates. Visualization was made with ultraviolet light (λ=254/365 nm) and, if necessary, using an ethanolic solution of potassium permanganate.

Overview of Synthesis Route

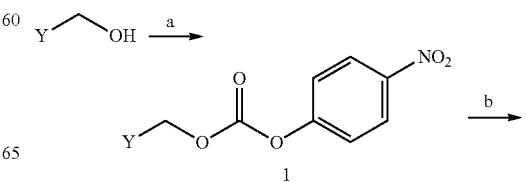

(a) General scheme for the synthesis of carbamate intermediates

-continued

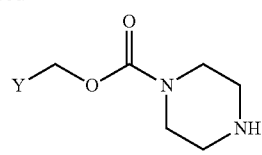

2 a) p-NO₂-phenylchloroformate, NMM/DCM/0° C., 2 h;
b) piperazine, TEA/DMF/0° C. to r.t, 12 h (b) General scheme for the synthesis of amine precursors

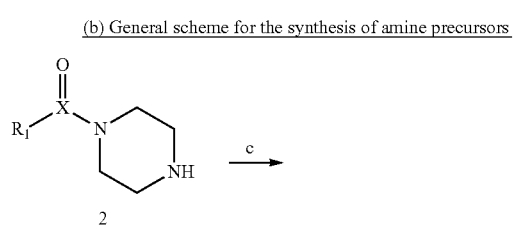

e)

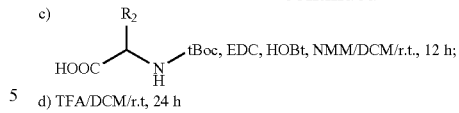

tBoc, EDC, HOBt, NMM/DCM/r.t., 12 h;

d) TFA/DCM/r.t, 24 h (c) General scheme for the synthesis of the final derivatives

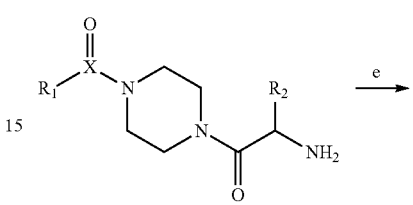

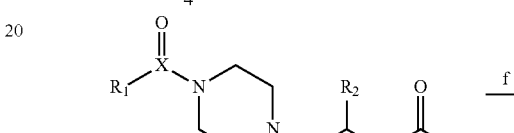

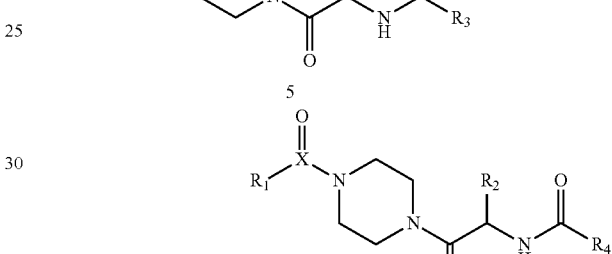

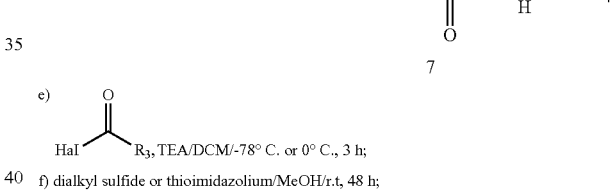

e)

Hal $\overset{O}{\underset{}{\|}}$ R₃, TEA/DCM/-78° C. or 0° C., 3 h;

f) dialkyl sulfide or thioimidazolium/MeOH/r.t, 48 h;

(d) Synthesis of the final derivatives

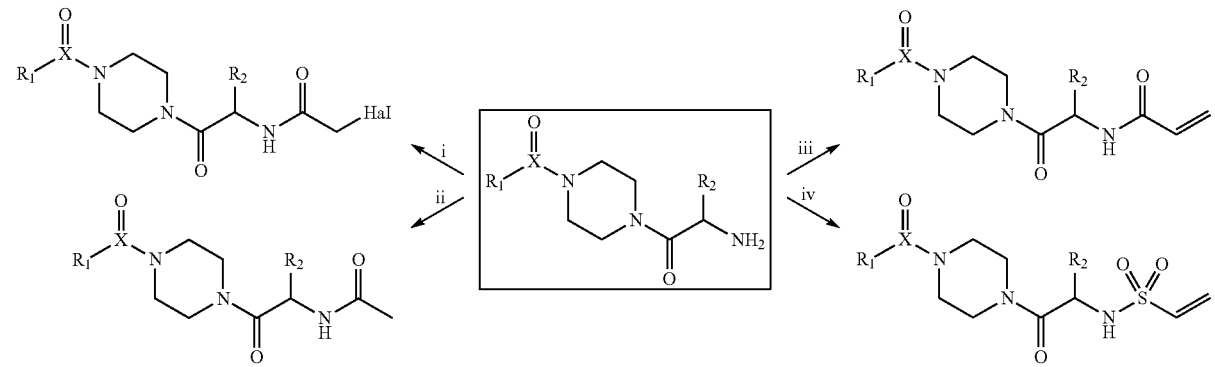

i) bromoacetyl bromide chloroacetyl chloride, TEA/DCM/-78° C. to r.t, 12 h;
ii) acetyl bromide, TEA/DCM/-78° C., 2 h;
iii) acryloyl chloride, TEA/ACN/0° C. to r.t, 3 h;
iv) 2-chloroethylsulfonyl chloride, TEA/DCM/-60° C. to 0° C., 4 h;

General Method for the Synthesis of the p-nitrophenylcarbonates (A)

Under nitrogen atmosphere, N-methylmorpholine (1.6 eq.) was added to a solution of the corresponding alcohols (1 eq., 3 mmol) in DCM (20 ml). The mixture was cooled to 0° C. and subsequently a solution of p-nitrophenyl chloroformate (1.5 eq.) in DCM (5 ml) was added slowly, and the mixture was vigorously stirred at 0° C. until the complete consumption of the starting material (usually 1-2 h). The reaction mixture was diluted with DCM (75 ml) and subsequently washed with sodium bicarbonate (aqueous satd. soln., 3×100 ml). The recovered organic layer was dried over magnesium sulfate and the solvent evaporated under vacuum.

(a) methyl 4-[(4-nitrophenoxy)carbonyloxymethyl]benzoate (1b)

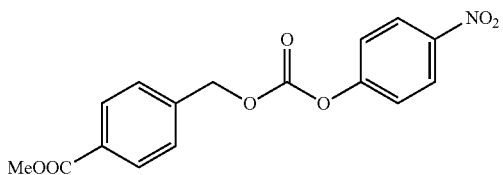 [SMILES: COC(=O)c1ccc(COC(=O)Oc2ccc([N+](=O)[O-])cc2)cc1]

The crude product obtained following the general protocol was washed with methanol, then with diethyl ether and further dried under reduced pressure to remove traces of solvents. $C_{16}H_{13}NO_7$; yield 88%; white solid; m.p. 95-96° C.; M=331.28 g/mol; IR (ATR): v=1763 (s), 1706 (s), 1527 (s), 1448 (m), 1430 (m), 1281 (m), 1208 (m-s), 980 (m), 853 (m-s), 753 (s) cm$^{-1}$; $^1$H NMR (250 MHz, CDCl$_3$) δ 8.28 (d, J=9.2 Hz, 2H), 8.08 (d, J=8.3 Hz, 2H), 7.51 (d, J=8.3 Hz, 2H), 7.38 (d, J=9.2 Hz, 2H), 5.35 (s, 2H), 3.93 (s, 3H); $^{13}$C NMR (63 MHz, CDCl$_3$) δ 166.7 ($C_q$), 155.5 ($C_q$), 152.5 ($C_q$), 145.6 ($C_q$), 139.2 ($C_q$), 130.8 ($C_q$), 130.2 (2CH), 128.2 (2CH), 125.5 (2CH), 121.9 (2CH), 70.2 (CH$_2$), 52.4 (CH$_3$); MS: m/z=354 [M+Na]$^+$;

(b) 2-naphthylmethyl (4-nitrophenyl) carbonate (1c)

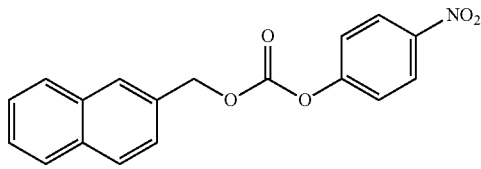 [SMILES: O=C(OCc1ccc2ccccc2c1)Oc1ccc([N+](=O)[O-])cc1]

The crude product obtained following the general protocol was washed with methanol, then with diethyl ether and further dried under reduced pressure to remove traces of solvents. $C_{18}H_{13}NO_5$; yield 67%; white solid; m.p. 151-152° C.; M=323.30 g/mol; IR (ATR): v=1748 (s), 1524 (m), 1351 (m), 1263 (s), 1214 (s), 953 (m), 859 (m), 750 (m) cm$^{-1}$; $^1$H NMR (250 MHz, CDCl$_3$) δ 8.31-8.24 (m, 2H), 7.92-7.84 (m, 4H), 7.56-7.50 (m, 3H), 7.42-7.36 (m, 2H), 5.47 (s, 2H); $^{13}$C NMR (63 MHz, CDCl$_3$) δ 155.7 ($C_q$), 152.6 ($C_q$), 145.5 ($C_q$), 133.6 ($C_q$), 133.2 ($C_q$), 131.7 ($C_q$), 128.9 (CH), 128.3 (CH), 128.3 (CH), 127.9 (CH), 126.9 (CH), 126.7 (CH), 126.0 (CH), 125.4 (2CH), 121.9 (2CH), 71.3 (CH$_2$); MS: m/z=346 [M+Na]$^+$;

(c) methyl 6-[(4-nitrophenoxy)carbonyloxymethyl]naphthalene-2-carboxylate (1d)

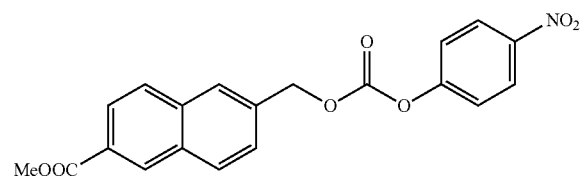 [SMILES: COC(=O)c1ccc2cc(COC(=O)Oc3ccc([N+](=O)[O-])cc3)ccc2c1]

The crude product obtained following the general protocol was used for the next steps without further purification. $C_{20}H_{15}NO_7$; white solid; yield 88%; M=381.34 g/mol; IR (ATR): v=1754 (s), 1715 (s), 1515 (s), 1384 (m), 1254 (m), 1208 (m-s), 853 (m-s), 750 (w) cm$^{-1}$; $^1$H NMR (250 MHz, CDCl$_3$) δ 8.63 (s, 1H), 8.31-8.25 (m, 2H), 8.11 (dd, J=8.6 Hz, J=1.6 Hz, 1H), 8.01 (d, J=8.5 Hz, 1H), 7.95 (as, 1H), 7.91 (d, J=8.7 Hz, 1H), 7.60 (dd, J=8.4 Hz, J=1.7 Hz, 1H), 7.43-7.36 (m, 2H), 5.48 (s, 2H), 4.00 (s, 3H); $^{13}$C NMR (63 MHz, CDCl$_3$) δ 167.2 ($C_q$), 155.6 ($C_q$), 152.6 ($C_q$), 145.6 ($C_q$), 135.4 ($C_q$), 134.3 ($C_q$), 132.6 ($C_q$), 131.0 (CH), 130.3 (CH), 128.5 (CH), 128.4 ($C_q$), 127.8 (CH), 126.6 (CH), 126.1 (CH), 125.5 (2CH), 121.9 (2CH), 70.9 (CH$_2$), 52.5 (CH$_3$); MS: m/z=404 [M+Na]$^+$;

(d) 1-adamantylmethyl (4-nitrophenyl) carbonate (1f)

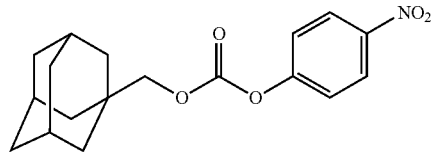 [SMILES: O=C(OCC12CC3CC(CC(C3)C1)C2)Oc1ccc([N+](=O)[O-])cc1]

The crude product obtained following the general protocol was washed with methanol, then with diethyl ether and further dried under reduced pressure to remove traces of solvents. $C_{18}H_{21}NO_5$; yield 82%; white solid; m.p. 102-103° C.; M=331.36 g/mol; IR (ATR): v=2913 (m), 2847 (m), 1748 (s), 1518 (s), 1342 (m-s), 1266 (m-s), 1217 (s), 856 (m), 762 (w), 729 (w) cm$^{-1}$; $^1$H NMR (250 MHz, CDCl$_3$) δ 8.31-8.25 (m, 2H), 7.42-7.36 (m, 2H), 3.89 (s, 2H), 2.03 (s, 3H), 1.79-1.70 (m, 6H), 1.61 (d, J=2.6 Hz, 6H); $^{13}$C NMR (63 MHz, CDCl$_3$) δ 155.9 ($C_q$), 152.9 ($C_q$), 145.4 ($C_q$), 125.4 (2CH), 121.9 (2CH), 79.1 (CH$_2$), 39.0 (3CH$_2$), 36.9 (3CH$_2$), 33.5 ($C_q$), 28.0 (3CH); MS: m/z=354 [M+Na]$^+$;

(e) 2-(1-adamantyl)ethyl(4-nitrophenyl) carbonate (1g)

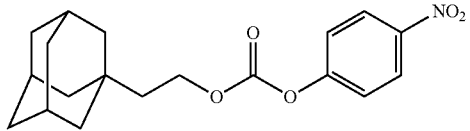 [SMILES: O=C(OCCC12CC3CC(CC(C3)C1)C2)Oc1ccc([N+](=O)[O-])cc1]

The crude product obtained following the general protocol was washed with methanol, then with diethyl ether and further dried under reduced pressure to remove traces of solvents. $C_{19}H_{23}NO_5$; yield 81%; white solid; m.p. 94-95° C.; M=345.39 g/mol; IR (ATR): v=2898 (m), 2841 (w), 1757 (s), 1527 (s), 1342 (s), 1260 (s), 1205 (s), 950 (m), 856 (s), 668 (m) cm$^{-1}$; $^1$H NMR (250 MHz, CDCl$_3$) δ 8.31-8.35 (m, 2H), 7.41-7.34 (m, 2H), 4.35 (t, J=7.5 Hz, 2H), 1.98 (as, 3H), 1.75-1.62 (m, 6H), 1.59-1.53 (m, 8H); $^{13}$C NMR (63 MHz, CDCl$_3$) δ 155.7 ($C_q$), 152.6 ($C_q$), 145.4 ($C_q$), 125.4 (2CH), 121.9 (2CH), 66.4 (CH$_2$), 42.5 (3CH$_2$), 42.3 (CH$_2$), 37.0 (3CH$_2$), 31.8 ($C_q$), 28.6 (3CH); MS: m/z=368 [M+Na]$^+$;

General Method for the Piperazine Alkylation Step (B)

Under inert atmosphere and at 0° C., the previously obtained carbonate (1 eq., 1.5 mmol) was added to a solution of piperazine (2 eq.) and TEA (5 eq.) in DMF (20 ml). The mixture was allowed to come back to room temperature and stirred vigorously overnight. After the complete consumption of the starting material, the mixture was diluted with ethyl acetate (100 ml) and washed with sodium chloride (aqueous satd. soln., 3×200 ml). The organic layer was dried over magnesium sulfate, filtered and the solvent evaporated under reduced pressure.

(a) (4-methoxycarbonylphenyl)methyl piperazine-1-carboxylate (2b)

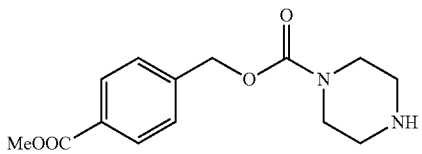 [SMILES: COC(=O)c1ccc(COC(=O)N2CCNCC2)cc1]

The crude product obtained following the general protocol was further purified by flash chromatography (eluent: DCM/MeOH 9/1) to conduct to the final derivative. $C_{14}H_{18}N_2O_4$; yield 64%; light yellow solid; m.p. 69-70° C.; M=278.30 g/mol; IR (ATR): v=3338 (w), 2950 (w), 1709 (s), 1687 (s), 1433 (s), 1423 (s), 1405 (s), 1275 (s), 1226 (s), 1129 (s), 1105 (s), 798 (m), 762 (s), 750 (s) cm$^{-1}$; $^1$H NMR (250 MHz, CDCl$_3$) δ 8.03 (d, J=8.3 Hz, 2H), 7.41 (d, J=8.1 Hz, 2H), 5.18 (s, 2H), 3.91 (s, 3H), 3.49 (t, J=5.1 Hz, 4H), 2.84 (t, J=4.7 Hz, 4H), 1.86 (s, 1H); $^{13}$C NMR (63 MHz, CDCl$_3$) δ 166.9 ($C_q$), 155.2 ($C_q$), 142.0 ($C_q$), 130.0 (2CH), 129.9 ($C_q$), 127.5 (2CH), 66.5 (CH$_2$), 52.3 (CH$_3$), 45.9 (2CH$_2$), 45.1 (2CH$_2$); MS: m/z=279 [M+]$^+$;

(b) 2-naphthylmethyl piperazine-1-carboxylate (2c)

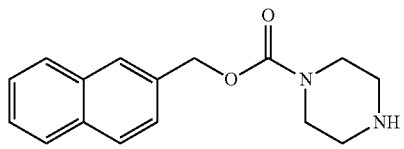 [SMILES: O=C(OCc1ccc2ccccc2c1)N1CCNCC1]

The crude product obtained following the general protocol was further purified by flash chromatography (eluent: DCM/MeOH 9/1) to conduct to the final derivative. $C_{16}H_{18}N_2O_2$; yield 92%; white solid; m.p. 44-45° C.; M=270.33 g/mol; IR (ATR): v=3259 (w), 2913 (w), 1681 (s), 1442 (m), 1417 (m), 1229 (s), 1129 (m), 1111 (m), 1084 (m), 744 (m) cm$^{-1}$; $^1$H NMR (250 MHz, CDCl$_3$) δ 7.85-7.81 (m, 4H), 7.51-7.44 (m, 3H), 5.29 (s, 2H), 3.49 (t, J=5.1 Hz, 4H), 2.82 (as, 4H), 2.25 (s, 1H); $^{13}$C NMR (63 MHz, CDCl$_3$) δ 155.4 ($C_q$), 134.2 ($C_q$), 133.3 ($C_q$), 133.2 ($C_q$), 128.4 (CH), 128.1 (CH), 127.8 (CH), 127.1 (CH), 126.3 (CH), 126.3 (CH), 125.9 (CH), 67.7 (CH$_2$), 45.8 (2CH$_2$), 44.8 (2CH$_2$); MS: m/z=271 [M+H]$^+$;

(c) (6-methoxycarbonyl-2-naphthyl)methyl piperazine-1-carboxylate (2d)

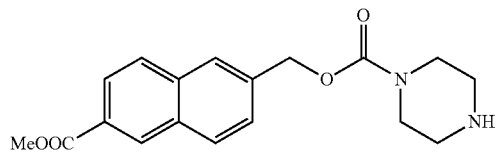 [SMILES: COC(=O)c1ccc2cc(COC(=O)N3CCNCC3)ccc2c1]

The crude product obtained following the general protocol was further purified by flash chromatography (eluent: DCM/MeOH 9/1) to conduct to the final derivative. $C_{18}H_{20}N_2O_4$; yield 85%; white solid; m.p. 94-95° C.; M=328.36 g/mol; IR (ATR): v=3320 (w), 2950 (w), 1712 (m), 1681 (s), 1433 (m), 1287 (m), 1226 (m), 1193 (m), 1120 (m), 1075 (m), 756 (m) cm$^{-1}$; $^1$H NMR (250 MHz, CDCl$_3$) δ 8.60 (s, 1H), 8.07 (dd, J=8.6 Hz, J=1.7 Hz, 1H), 7.95 (d, J=8.5 Hz, 1H), 7.88 (d, J=8.7 Hz, 1H), 7.84 (s, 1H), 7.53 (dd, J=8.5 Hz, J=1.6 Hz, 1H), 5.31 (s, 2H), 3.98 (s, 3H), 3.51 (t, J=5.1 Hz, 4H), 2.85 (at, J=4.6 Hz, 4H); $^{13}$C NMR (63 MHz, CDCl$_3$) δ 167.3 ($C_q$), 155.3 ($C_q$), 137.0 ($C_q$), 135.5 ($C_q$), 132.3 ($C_q$), 130.9 (CH), 129.9 (CH), 128.4 (CH), 127.8 ($C_q$), 126.6 (CH), 126.5 (CH), 125.8 (CH), 67.1 (CH$_2$), 52.4 (CH$_3$), 46.0 (2CH$_2$), 45.1 (2CH$_2$); MS: m/z=329 [M+H]$^+$ and 351 [M+Na]$^+$;

(d) 1-adamantylmethyl piperazine-1-carboxylate (2f)

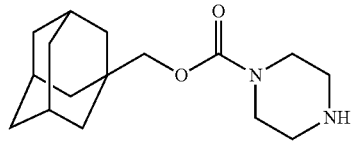 [SMILES: O=C(OCC12CC3CC(CC(C3)C1)C2)N1CCNCC1]

The crude product obtained following the general protocol was subsequently used without further purification. $C_{16}H_{26}N_2O_2$; yield 62%; light yellow solid; M=278.39 g/mol; IR (ATR): v=2883 (m-s), 2841 (m), 1678 (s), 1427 (s), 1232 (s), 1120 (m), 765 (m) cm$^{-1}$; $^1$H NMR (250 MHz, CDCl$_3$) δ 3.66 (s, 2H), 3.44 (t, J=5.1 Hz, 4H), 2.82 (t, J=5.1 Hz, 4H), 2.13 (s, 1H), 1.96 (as, 3H), 1.73-1.60 (m, 6H), 1.51 (d, J=2.5 Hz, 6H); $^{13}$C NMR (63 MHz, CDCl$_3$) δ 155.9 ($C_q$), 75.2 (CH$_2$), 46.0 (2CH$_2$), 44.9 (2CH$_2$), 39.5 (3CH$_2$), 37.1 (3CH$_2$), 33.6 ($C_q$), 28.2 (3CH); MS: m/z=279 [M+H]$^+$;

(e) 2-(1-adamantyl)ethyl piperazine-1-carboxylate (2g)

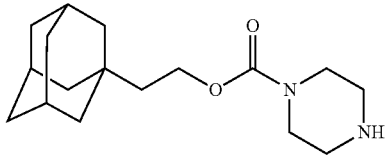 [SMILES: O=C(OCCC12CC3CC(CC(C3)C1)C2)N1CCNCC1]

The crude product obtained following the general protocol was further purified by flash chromatography (eluent: DCM/MeOH 95/5) to conduct to the final derivative. $C_{17}H_{28}N_2O_2$; yield 77%; light yellow oil becoming a light yellow solid on standing; m.p. 56-57° C.; M=292.42 g/mol; IR (ATR): v=2895 (s), 2837 (m), 1687 (s), 1436 (s), 1232 (s), 1120 (s), 1087 (m) cm$^{-1}$; $^1$H NMR (250 MHz, CDCl$_3$) δ 4.12 (t, J=7.3 Hz, 2H), 3.42 (t, J=5.0 Hz, 4H), 2.81 (t, J=5.0 Hz, 4H), 1.93 (as, 3H), 1.71-1.58 (m, 6H), 1.52-1.51 (m, 6H), 1.41 (t, J=7.3 Hz, 2H); $^{13}$C NMR (63 MHz, CDCl$_3$) δ 155.8 (C$_q$), 61.9 (CH$_2$), 46.0 (2CH$_2$), 44.9 (2CH$_2$), 43.0 (CH$_2$), 42.7 (3CH$_2$), 37.2 (3CH$_2$), 31.9 (C$_q$), 28.7 (3CH); MS: m/z=293 [M+H]$^+$;

(f) tert-butyl N-[2-[4-[[5-(dimethylamino)-1-naphthyl]sulfonyl]piperazin-1-yl]-2-oxo-ethyl]-carbamate (2 h)

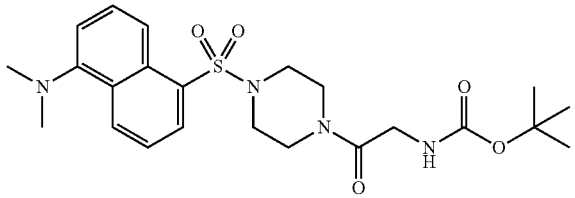 [SMILES: CN(C)c1cccc2c(S(=O)(=O)N3CCN(C(=O)CNC(=O)OC(C)(C)C)CC3)cccc12]

The coupling compound was obtained following the general protocol described before. The crude product was purified by flash-chromatography (DCM/MeOH 98/2) to give the titled derivative. $C_{23}H_{32}N_4O_5S$; yield 89%; light yellow solid; m.p. 176-177° C.; M=476.59 g/mol; IR (ATR): v=3287 (w), 2977 (w), 1703 (m), 1642 (s), 1339 (m), 1232 (m), 1160 (s), 1141 (s), 932 (m), 798 (s), 710 (m), 616 (m) cm$^{-1}$; $^1$H NMR (250 MHz, CDCl$_3$) δ 8.58 (d, J=8.5 Hz, 1H), 8.35 (d, J=8.7 Hz, 1H), 8.19 (dd, J=7.4 Hz, J=1.3 Hz, 1H), 7.54 (dd, J=8.6 Hz, J=7.5 Hz, 2H), 7.19 (d, J=7.0 Hz, 1H), 5.36 (as, 1H), 3.86 (d, J=4.5 Hz, 2H), 3.67-3.63 (m, 2H), 3.44-3.40 (m, 2H), 3.19-3.15 (m, 4H), 2.88 (s, 6H), 1.40 (s, 9H); $^{13}$C NMR (63 MHz, CDCl$_3$) δ 167.0 (C$_q$), 155.8 (C$_q$), 152.0 (C$_q$), 132.2 (C$_q$), 131.3 (CH), 131.0 (CH), 130.4 (C$_q$), 130.2 (C$_q$), 128.5 (CH), 123.3 (CH), 119.4 (CH), 115.5 (CH), 79.9 (C$_q$), 45.6 (CH$_2$), 45.5 (2CH$_3$), 45.4 (CH$_2$), 44.2 (CH$_2$), 42.2 (CH$_2$), 41.6 (CH$_2$), 28.4 (3CH$_3$); MS: m/z=499 [M+Na]$^+$;

General Method for the Peptide Coupling Step (C)

Under inert atmosphere and at room temperature, to a solution of the previously obtained piperazine (1.85 mmol, 1 eq.) in dichloromethane (DCM, 15 ml) were successively added: N-(3-Dimethylaminopropyl)-N'-ethylcarbodiimide (EDC, 1.85 mmol, 1 eq.), 1-hydroxybenzotriazole (0.37 mmol, 0.2 eq.), the corresponding Boc-protected aminoacid (1.85 mmol, 1 eq.) and N-methylmorpholine (5.55 mmol, 3 eq.). After 12 hours of stirring, the reaction mixture was diluted by addition of 75 ml of DCM and washed with citric acid (aq soln. 10%, 3×50 ml) and then with brine. The organic phase was subsequently dried over magnesium sulfate, filtered and the solvent evaporated under vacuum. The crude product was purified by flash-chromatography to give the desired coupling product.

(a) benzyl 4-[(2-(tert-butoxycarbonylamino)acetyl]piperazine-1-carboxylate (3a)

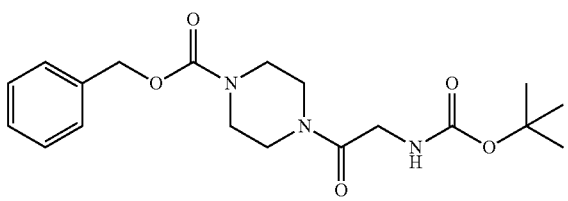 [SMILES: CC(C)(C)OC(=O)NCC(=O)N1CCN(C(=O)OCc2ccccc2)CC1]

The crude derivative obtained following the general protocol described before was purified by flash-chromatography (eluent: EtOAc/PE 5/5). $C_{19}H_{27}N_3O_5$; yield 95%; white solid; m.p. 66-67° C.; M=377.43 g/mol; IR (ATR): v=3329 (w), 2971 (w), 1691 (s), 1627 (m), 1527 (m), 1420 (m), 1223 (s), 1153 (m), 756 (m), 695 (m) cm$^{-1}$; $^1$H NMR (250 MHz, CDCl$_3$) δ 7.40-7.32 (m, 5H), 5.48 (as, 1H), 5.14 (s, 2H), 3.96 (d, J=4.4 Hz, 2H), 3.69-3.60 (m, 2H), 3.53-3.49 (m, 4H), 3.45-3.47 (m, 2H), 1.44 (s, 9H); $^{13}$C NMR (63 MHz, CDCl$_3$) δ 167.2 (C$_q$), 155.9 (C$_q$), 155.2 (C$_q$), 136.4 (C$_q$), 128.7 (2CH), 128.4 (CH), 128.2 (2CH), 79.9 (C$_q$), 67.7 (CH$_2$), 44.3 (CH$_2$), 43.7 (CH$_2$), 43.6 (CH$_2$), 42.4 (CH$_2$), 41.8 (CH$_2$), 28.5 (3CH$_3$); MS: m/z=400 [M+Na]$^+$;

(b) (4-methoxycarbonylphenyl)methyl 4-[2-(tert-butoxycarbonylamino)acetyl]piperazine-1-carboxylate (3b)

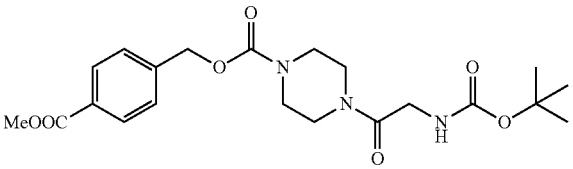 [SMILES: COC(=O)c1ccc(COC(=O)N2CCN(C(=O)CNC(=O)OC(C)(C)C)CC2)cc1]

The crude derivative obtained following the general protocol described before was purified by flash-chromatography (eluent: EtOAc/PE 5/5) $C_{21}H_{29}N_3O_7$; yield 80%; white solid; m.p. 90-91° C.; M=435.47 g/mol; IR (ATR): v=2977 (w), 1703 (s), 1651 (s), 1430 (m), 1278 (m), 1223 (m), 1160 (m), 1105 (m), 1017 (m), 756 (m) cm$^{-1}$; $^1$H NMR (250 MHz, CDCl$_3$) δ 8.04 (d, J=8.4 Hz, 2H), 7.41 (d, J=8.4 Hz, 2H), 5.47 (as, 1H), 5.20 (s, 2H), 3.97 (d, J=4.5 Hz, 2H), 3.92 (s, 3H), 3.70-3.62 (m, 2H), 3.56-3.50 (m, 4H), 3.41-3.37 (m, 2H), 1.44 (s, 9H); $^{13}$C NMR (63 MHz, CDCl$_3$) δ 167.3 (C$_q$), 166.8 (C$_q$), 154.9 (C$_q$), 141.4 (2C$_q$), 130.1 (C$_q$), 130.0 (2CH), 127.7 (2CH), 80.0 (C$_q$), 67.0 (CH$_2$), 52.3 (CH$_3$), 44.3 (CH$_2$), 43.7 (2CH$_2$), 42.4 (CH$_2$), 41.8 (CH$_2$), 28.5 (3CH$_3$); MS: m/z=458 [M+Na]$^+$;

(c) 2-naphthylmethyl 4-[2-(tert-butoxycarbonylamino)acetyl]piperazine-1-carboxylate (3c)

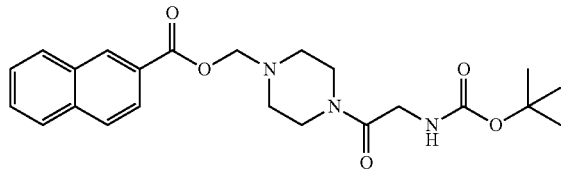 [SMILES: CC(C)(C)OC(=O)NCC(=O)N1CCN(COC(=O)c2ccc3ccccc3c2)CC1]

The crude derivative obtained following the general protocol described before was purified by flash-chromatography (eluent: EtOAc/PE 5/5). $C_{23}H_{29}N_3O_5$; yield 91%; white solid; m.p. 41-42° C.; M=427.49 g/mol; IR (ATR): v=3332 (w), 2971 (w), 1697 (s), 1645 (s), 1460 (m), 1427 (s), 1214 (s), 1160 (m), 1117 (w), 1017 (w), 747 (w) cm$^{-1}$; $^1$H NMR (250 MHz, CDCl$_3$) δ 7.87-7.82 (m, 4H), 7.53-7.45 (m, 3H), 5.48 (as, 1H), 5.31 (s, 2H), 3.96 (d, J=4.4 Hz, 2H), 3.69-3.61 (m, 2H), 3.56-3.50 (4H), 3.42-3.33 (m, 2H), 1.44 (s, 9H); $^{13}$C NMR (63 MHz, CDCl$_3$) δ 167.3 ($C_q$), 155.9 ($C_q$), 155.2 ($C_q$), 133.8 ($C_q$), 133.3 ($C_q$), 133.3 ($C_q$), 128.6 (CH), 128.1 (CH), 127.9 (CH), 127.5 (CH), 126.5 (CH), 126.5 (CH), 126.0 (CH), 79.9 ($C_q$), 67.9 (CH$_2$), 44.3 (CH$_2$), 43.7 (2CH$_2$), 42.4 (CH$_2$), 41.8 (CH$_2$), 28.5 (3CH$_3$); MS: m/z=450 [M+Na]$^+$;

(d) (6-methoxycarbonyl-2-naphthyl)methyl 4-[2-(tert-butoxycarbonylamino)acetyl]-piperazine-1-carboxylate (3d)

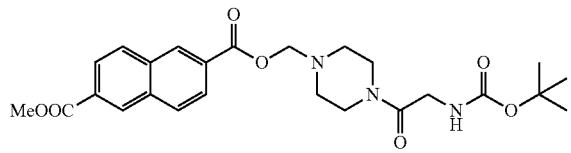 [SMILES: COC(=O)c1ccc2cc(C(=O)OCN3CCN(C(=O)CNC(=O)OC(C)(C)C)CC3)ccc2c1]

The crude derivative obtained following the general protocol described before was purified by flash-chromatography (eluent: DCM/MeOH 95/5). $C_{25}H_{31}N_3O_7$; yield 97%; white solid; m.p. 43-44° C.; M=485.53 g/mol; IR (ATR): v=3350 (w), 2974 (w), 1697 (s), 1651 (s), 1460 (m), 1423 (s), 1366 (m), 1284 (m), 1220 (m-s), 1163 (m), 762 (w) cm$^{-1}$; $^1$H NMR (250 MHz, CDCl$_3$) δ 8.60 (s, 1H), 8.08 (dd, J=8.6 Hz, J=1.6 Hz, 1H), 7.96 (d, J=8.5 Hz, 1H), 7.88 (d, J=1 Hz, 1H), 7.84 (s, 1H), 7.52 (dd, J=8.4 Hz, J=1.6 Hz, 1H), 5.47 (s, 1H), 5.33 (s, CH$_2$), 3.99-3.98 (m, 5H), 3.70-3.62 (m, 2H), 3.58-3.52 (m, 4H), 3.41-3.36 (m, 2H), 1.44 (s, 9H); $^{13}$C NMR (63 MHz, CDCl$_3$) δ 167.3 ($C_q$), 155.1 ($C_q$), 136.4 ($C_q$), 135. ($C_q$), 132.3 ($C_q$), 130.9 (CH), 130.0 (CH), 128.4 (CH), 128.0 ($C_q$), 127.0 (CH), 126.6 (CH), 125.9 (CH), 80.0 ($C_q$), 67.6 (CH$_2$), 52.4 (CH$_3$), 44.3 (CH$_2$), 43.8 (CH$_2$), 43.7 (CH$_2$), 42.4 (CH$_2$), 41.8 (CH$_2$), 28.5 (3CH$_3$); MS: m/z=508 [M+Na]$^+$;

(e) tert-butyl N-[2-[4-(adamantane-1-carbonyl)piperazin-1-yl]-2-oxo-ethyl]carbamate (3e)

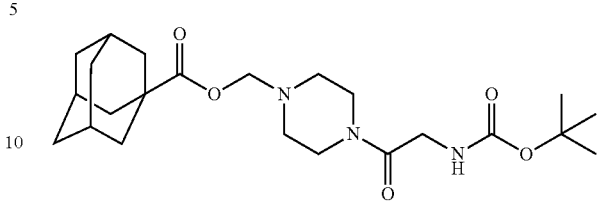

The crude derivative obtained following the general protocol described before was subsequently purified by flash chromatography (eluent: PE/EtOAc 5/5) to conduct to the desired derivative. $C_{22}H_{35}N_3O_4$; yield 78%; white solid; m.p. 187-188° C.; M=405.53 g/mol; IR (ATR): v=3423 (w), 2904 (m), 1712 (s), 1642 (s), 1615 (s), 1442 (m-s), 1399 (m), 1153 (m), 1008 (m) cm$^{-1}$; $^1$H NMR (250 MHz, DMSO) δ 6.75 (t, J=5.7 Hz, 1H), 3.78 (d, J=5.8 Hz, 2H), 3.65-3.49 (m, 4H), 3.47-3.36 (m, 4H), 1.97 (as, 3H), 1.90 (as, 6H), 1.73-1.63 (m, 6H), 1.38 (s, 9H); $^{13}$C NMR (63 MHz, DMSO) δ 174.6 ($C_q$), 167.6 ($C_q$), 155.8 ($C_q$), 77.9 ($C_q$), 44.6 (2CH$_2$), 44.1 (CH$_2$), 41.7 (2CH$_2$), 40.9 ($C_q$), 28.4 (3CH$_2$), 36.0 (3CH$_2$), 28.2 (3CH), 27.9 (3CH$_3$); MS: m/z=428 [M+Na]$^+$;

(f) 1-adamantylmethyl 4-[2-(tert-butoxycarbonylamino)acetyl]perazine-1-carboxylate (3f)

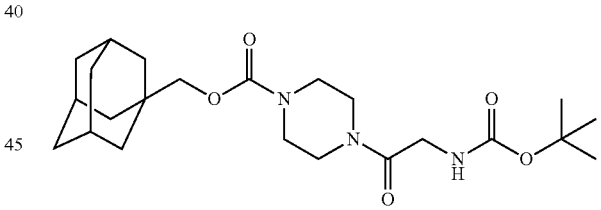

The crude derivative obtained following the general protocol described before was subsequently purified by flash chromatography (eluent: PE/EtOAc 5/5). $C_{23}H_{37}N_3O_5$; yield 78%; white solid; m.p. 156-157° C.; M=435.56 g/mol; IR (ATR): v=3405 (w), 2907 (m), 1712 (s), 1678 (s), 1639 (s), 1475 (m-s), 1430 (s), 1229 (m-s), 1163 (m-s) cm$^{-1}$; $^1$H NMR (250 MHz, CDCl$_3$) δ 5.48 (as, 1H), 3.97 (d, J=4.4 Hz, 2H), 3.71 (s, 2H), 3.65-3.59 (m, 2H), 3.53-3.47 (m, 4H), 3.40-3.37 (m, 2H), 1.99 (as, 3H), 1.76-1.62 (m, 6H), 1.53 (d, J=2.5 Hz, 6H), 1.45 (s, 9H); $^{13}$C NMR (63 MHz, CDCl$_3$) δ 167.3 ($C_q$), 155.9 ($C_q$), 155.7 ($C_q$), 79.9 ($C_q$), 75.6 (CH$_2$), 44.3 (CH$_2$), 43.7 (CH$_2$), 43.6 (CH$_2$), 42.4 (CH$_2$), 41.9 (CH$_2$), 39.5 (3CH$_2$), 37.1 (3CH$_2$), 33.6 ($C_q$), 28.5 (3CH$_3$), 28.1 (3CH); MS: m/z=458 [M+Na]$^+$;

(g) 2-(1-adamantyl)ethyl 4-[2-(tert-butoxycarbonylamino)acetyl]perazine-1-carboxylate (3g)

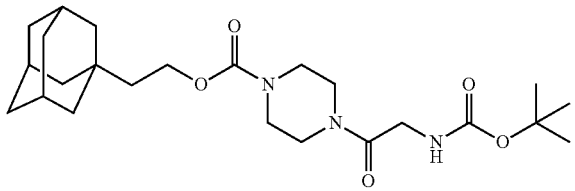 [SMILES: CC(C)(C)OC(=O)NCC(=O)N1CCN(C(=O)OCCC23CC4CC(CC(C4)C2)C3)CC1]

The crude derivative obtained following the general protocol described before was subsequently purified by flash chromatography (eluent: PE/EtOAc 5/5). $C_{24}H_{39}N_3O_5$; yield 78%; white solid; m.p. 167-168° C.; M=449.58 g/mol; IR (ATR): v=3362 (w), 2898 (m), 2844 (w), 1706 (m-s), 1687 (m-s), 1645 (s), 1463 (m), 1427 (m-s), 1217 (s), 1156 (m), 1123 (m) cm$^{-1}$; $^1$H NMR (250 MHz, CDCl$_3$) δ 5.48 (as, 1H), 4.14 (t, J=7.3 Hz, 2H), 3.95 (d, J=4.4 Hz, 2H), 3.62-3.58 (m, 2H), 3.47-3.41 (m, 4H), 3.37-3.34 (m, 2H), 1.93 (as, 3H), 1.72-1.58 (m, 6H), 1.51 (d, J=2.5 Hz, 6H), 1.43-1.39 (m, 11H); $^{13}$C NMR (63 MHz, CDCl$_3$) δ 167.2 ($C_q$), 155.9 ($C_q$), 155.5 ($C_q$), 79.9 ($C_q$), 62.5 (CH$_2$), 44.3 (CH$_2$), 43.6 (CH$_2$), 43.5 (CH$_2$), 42.9 (CH$_2$), 42.7 (3CH$_2$), 42.4 (CH$_2$), 41.9 (CH$_2$), 37.1 (3CH$_2$), 31.9 ($C_q$), 28.7 (3CH), 28.5 (3CH$_3$); MS: m/z=472 [M+Na]$^+$;

(h) benzyl 4-[(2R)-2-(tert-butoxycarbonylamino)propanoyl]piperazine-1-carboxylate (3i)

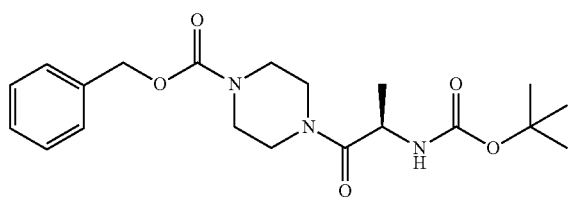 [SMILES: C[C@@H](NC(=O)OC(C)(C)C)C(=O)N1CCN(C(=O)OCc2ccccc2)CC1]

The crude derivative obtained following the general protocol described before was subsequently used without any further purification. $C_{20}H_{29}N_3O_5$; colorless viscous oil; yield 90%; M=391.46 g/mol; IR (ATR): v=2980 (w), 1700 (s), 1645 (s), 1423 (m), 1217 (m), 1160 (m), 1014 (m), 765 (w), 695 (w) cm$^{-1}$; $^1$H NMR (250 MHz, CDCl$_3$) δ 7.39-7.32 (m, 5H), 5.49 (d, J=8.1 Hz, 1H), 5.15 (s, 2H), 4.60 (p, J=7.1 Hz, 1H), 3.74-3.39 (m, 8H), 1.43 (s, 9H), 1.29 (d, J=6.9 Hz, 3H); $^{13}$C NMR (63 MHz, CDCl$_3$) δ 171.6 ($C_q$), 155.2 (2$C_q$), 136.4 ($C_q$), 128.7 (2CH), 128.4 (CH), 128.2 (2CH), 79.9 ($C_q$), 67.7 (CH$_2$), 46.2 (CH), 45.3 (CH$_2$), 44.0 (CH$_2$), 43.7 (CH$_2$), 42.0 (CH$_2$), 28.5 (3CH$_3$), 19.3 (CH$_3$); MS: m/z=414 [M+Na]$^+$;

(i) benzyl 4-[(2S)-2-(tert-butoxycarbonylamino)propanoyl]perazine-1-carboxylate (3j)

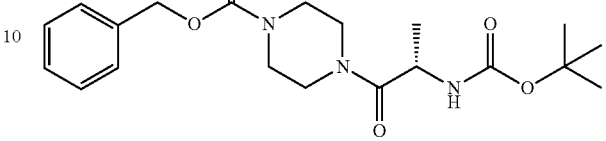

The crude derivative obtained following the general protocol described before was subsequently used without any further purification. $C_{20}H_{29}N_3O_5$; colorless viscous oil; yield 90%; M=391.46 g/mol; IR (ATR): v=2974 (w), 1694 (s), 1639 (s), 1433 (m), 1220 (m), 1163 (m), 1014 (m), 762 (w), 698 (w) cm$^{-1}$; $^1$H NMR (250 MHz, CDCl$_3$) δ 7.40-7.30 (m, 5H), 5.47 (d, J=7.9 Hz, 1H), 5.15 (s, 2H), 4.60 (p, J=7.1 Hz, 1H), 3.76-3.39 (m, 8H), 1.43 (s, 9H), 1.29 (d, J=6.9 Hz, 3H); $^{13}$C NMR (63 MHz, CDCl$_3$) δ 184.8 ($C_q$), 171.6 ($C_q$), 155.2 (2$C_q$), 136.4 ($C_q$), 128.7 (2CH), 128.4 (CH), 128.2 (2CH), 79.9 ($C_q$), 67.7 (CH$_2$), 46.2 (CH), 45.3 (CH$_2$), 44.0 (CH$_2$), 43.7 (CH$_2$), 42.0 (CH$_2$), 28.5 (3CH$_3$), 19.5 (CH$_3$); MS: m/z=414 [M+Na]$^+$;

(j) benzyl 4-[(2R)-2-(tert-butoxycarbonylamino)-3-phenyl-propanoyl]piperazine-1-carboxylate (3k)

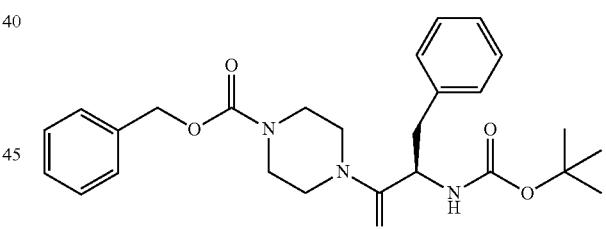

The crude derivative obtained following the general protocol described before was subsequently used without any further purification. $C_{26}H_{33}N_3O_5$; colorless viscous oil; yield 97%; M=467.56 g/mol; IR (ATR): v=3314 (w), 2968 (w), 1700 (s), 1636 (s), 1423 (m), 1220 (m-s), 1163 (m-s), 1011 (w-m), 750 (w), 698 (m) cm$^{-1}$; $^1$H NMR (250 MHz, CDCl$_3$) δ 7.41-7.17 (m, 10H), 5.41 (d, J=8.6 Hz, 1H), 5.10 (s, 2H), 4.85-4.75 (m, 1H), 3.60-3.14 (m, 6H), 3.06-2.87 (m, 3H), 2.66-2.57 (m, 1H), 1.42 (s, 9H); $^{13}$C NMR (63 MHz, CDCl$_3$) δ 170.6 ($C_q$), 155.2 ($C_q$), 155.1 ($C_q$), 136.5 ($C_q$), 136.4 ($C_q$), 129.7 (2CH), 128.8 (2CH), 128.7 (2CH), 128.4 (CH), 128.2 (2CH), 127.3 (CH), 80.1 ($C_q$), 67.6 (CH$_2$), 51.1 (CH), 45.4 (CH$_2$), 43.4 (CH$_2$), 43.4 (CH$_2$), 41.8 (CH$_2$), 40.6 (CH$_2$), 28.5 (3CH$_3$); MS: m/z=490 [M+Na]$^+$;

(k) benzyl 4-[(2S)-2-(tert-butoxycarbonylamino)-3-phenyl-propanoyl]perazine-1-carboxylate (3l)

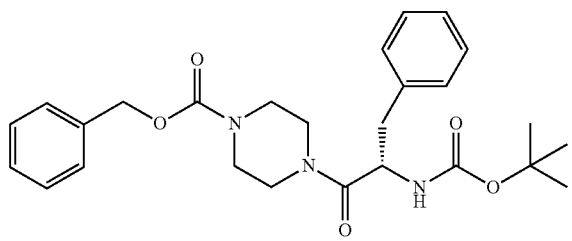 [SMILES: CC(C)(C)OC(=O)N[C@@H](Cc1ccccc1)C(=O)N1CCN(C(=O)OCc2ccccc2)CC1]

The crude derivative obtained following the general protocol described before was subsequently used without any further purification. $C_{26}H_{33}N_3O_5$; colorless viscous oil; yield 97%; M=467.56 g/mol; IR (ATR): v=2971 (w), 1700 (s), 1633 (s), 1420 (m), 1220 (s), 1163 (s), 1011 (m), 695 (s) cm$^{-1}$; $^1$H NMR (250 MHz, CDCl$_3$) δ 7.41-7.17 (m, 10H), 5.41 (d, J=8.5 Hz, 1H), 5.10 (s, 2H), 4.85-4.75 (m, 1H), 3.60-3.38 (m, 3H), 3.33-3.14 (m, 3H), 3.06-2.87 (m, 3H), 2.67-2.57 (m, 1H), 1.42 (s, 9H); $^{13}$C NMR (63 MHz, CDCl$_3$) δ 170.6 ($C_q$), 155.2 ($C_q$), 155.1 ($C_q$), 136.5 ($C_q$), 136.4 ($C_q$), 129.7 (2CH), 128.8 (2CH), 128.7 (2CH), 128.4 (CH), 128.2 (2CH), 127.3 (CH), 80.1 ($C_q$), 67.6 (CH$_2$), 51.1 (CH), 45.4 (CH$_2$), 43.4 (2CH$_2$), 41.8 (CH$_2$), 40.6 (CH$_2$), 28.5 (3CH$_3$); MS: m/z=490 [M+Na]$^+$;

General Protocol for the Carbamate Deprotection Step (D)

The previously obtained carbamate (1.2 mmol) was dissolved in DCM (15 ml) and reacted with an excess of trifluoroacetic acid (9.6 mmol, 8 eq.) at room temperature, until the complete consumption of the starting material (generally 3 h). At the end of the reaction, the mixture was diluted with DCM (35 ml) and washed with hydrogen chloride (aq. soln. 0.5 M, 3×50 ml). The pH of the combined aqueous layers was adjusted to 9-10 by addition of potassium carbonate (satd. soln.), then extracted with DCM (3×75 ml). The combined organic layers were dried over magnesium sulfate and the solvent evaporated under reduced pressure. The obtained amine was used further without any other purification.

(a) benzyl 4-(2-aminoacetyl)piperazine-1-carboxylate (4a)

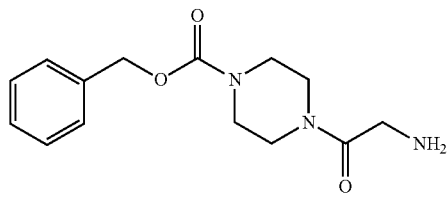 [SMILES: NCC(=O)N1CCN(C(=O)OCc2ccccc2)CC1]

$C_{14}H_{19}N_3O_3$; yield 82%; white solid; m.p. 52-53° C.; M=277.32 g/mol; IR (ATR): v=3526 (w), 2901 (w), 1678 (s), 1642 (s), 1420 (m-s), 1363 (w), 1281 (w), 1229 (s), 1123 (m-s) cm$^{-1}$; $^1$H NMR (250 MHz, CDCl$_3$) δ 7.38-7.32 (m, 5H), 5.14 (s, 2H), 3.70-3.58 (m, 2H), 3.52-3.50 (m, 4H), 3.47 (s, 2H), 3.43-3.30 (m, 2H), 1.80 (s, 2H); $^{13}$C NMR (63 MHz, CDCl$_3$) δ 171.5 ($C_q$), 155.2 ($C_q$), 136.4 ($C_q$), 128.6 (2CH), 128.3 (CH), 128.1 (2CH), 67.6 (CH$_2$), 44.1 (CH$_2$), 43.7 (2CH$_2$), 43.4 (CH$_2$), 41.8 (CH$_2$); MS: m/z=278 [M+H]$^+$;

(b) (4-methoxycarbonylphenyl)methyl 4-(2-aminoacetyl)piperazine-1-carboxylate (4b)

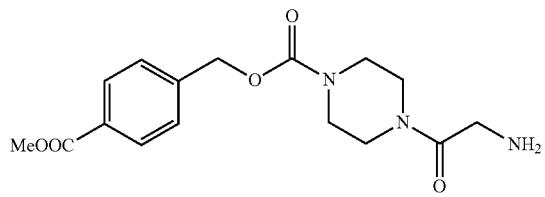 [SMILES: COC(=O)c1ccc(COC(=O)N2CCN(C(=O)CN)CC2)cc1]

$C_{16}H_{21}N_3O_3$; yield 88%; light-yellow solid; m.p. 94-95° C.; M=335.36 g/mol; IR (ATR): v=3520 (w), 3350 (w), 2904 (w), 1715 (s), 1691 (s), 1624 (m-s), 1448 (m-s), 1430 (s), 1275 (s), 1226 (s), 1111 (s), 1065 (m), 759 (s) cm$^{-1}$; $^1$H NMR (250 MHz, CDCl$_3$) δ 8.03 (d, J=8.3 Hz, 2H), 7.41 (d, J=8.3 Hz, 2H), 5.20 (s, 2H), 3.92 (s, 3H), 3.69-3.59 (m, 2H), 3.54-3.52 (m, 4H), 3.47 (s, 2H), 3.40-3.33 (m, 2H), 1.62 (s, 2H); $^{13}$C NMR (63 MHz, CDCl$_3$) δ 171.6 ($C_q$), 166.8 ($C_q$), 155.0 ($C_q$), 141.5 ($C_q$), 130.1 ($C_q$), 130.0 (2CH), 127.7 (2CH), 66.9 (CH$_2$), 52.3 (CH$_3$), 44.1 (CH$_2$), 43.8 (2CH$_2$), 43.5 (CH$_2$), 41.8 (CH$_2$); MS: m/z=336 [M+H]$^+$;

(c) 2-naphthylmethyl 4-(2-aminoacetyl)piperazine-1-carboxylate (4c)

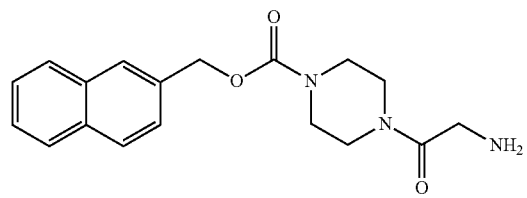 [SMILES: NCC(=O)N1CCN(C(=O)OCc2ccc3ccccc3c2)CC1]

$C_{18}H_{21}N_3O_3$; yield 61%; white solid; m.p. 109-110° C.; M=327.38 g/mol; IR (ATR): v=3526 (w), 3350 (w), 2907 (w), 1691 (s), 1618 (s), 1445 (m), 1433 (s), 1281 (m-s), 1220 (s), 804 (s), 735 (m) cm$^{-1}$; $^1$H NMR (250 MHz, CDCl$_3$) δ 7.86-7.82 (m, 4H), 7.53-7.45 (m, 3H), 5.31 (s, 2H), 3.70-3.58 (m, 2H), 3.57-3.50 (m, 4H), 3.46 (s, 2H), 3.43-3.30 (m, 2H), 1.64 (s, 2H); $^{13}$C NMR (63 MHz, CDCl$_3$) δ 171.6 ($C_q$), 133.8 ($C_q$), 133.3 ($C_q$), 128.6 (CH), 128.1 (CH), 127.9 (CH), 127.4 (CH), 126.5 (CH), 126.5 (CH), 126.0 (CH), 67.9 (CH$_2$), 44.1 (CH$_2$), 43.8 (2CH$_2$), 43.5 (CH$_2$), 41.9 (CH$_2$); MS: m/z=328 [M+H]$^+$;

(d) (6-methoxycarbonyl-2-naphthyl)methyl 4-(2-aminoacetyl)piperazine-1-carboxylate (4d)

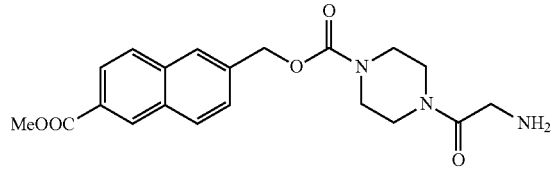 [SMILES: COC(=O)c1ccc2cc(COC(=O)N3CCN(C(=O)CN)CC3)ccc2c1]

$C_{20}H_{23}N_3O_5$; yield 79%; light yellow solid; m.p. 91-92° C.; M=385.41 g/mol; IR (ATR): v=2953 (w), 1718 (m), 1687 (s), 1639 (m), 1423 (m), 1281 (m), 1226 (m), 1196 (m), 1126 (m), 1075 (w), 759 (w-m) cm$^{-1}$; $^1$H NMR (250 MHz, CDCl$_3$) δ 8.60 (s, 1H), 8.08 (dd, J=8.6 Hz, J=1.7 Hz, 1H), 7.96 (d, J=8.5 Hz, 1H), 7.88 (d, J=8.7 Hz, 1H), 7.84 (s, 1H), 7.53 (dd, J=8.5 Hz, J=1.6 Hz, 1H), 5.33 (s, 2H), 3.99 (s, 3H), 3.69-3.63 (m, 2H), 3.57-3.54 (m, 4H), 3.47 (s, 2H), 3.40-3.34 (m, 2H), 1.60 (s, 2H); $^{13}$C NMR (63 MHz, CDCl$_3$) δ 171.7 ($C_q$), 167.3 ($C_q$), 155.1 ($C_q$), 136.5 ($C_q$), 135.5 ($C_q$), 132.3 ($C_q$), 130.9 (CH), 130.0 (CH), 128.4 (CH), 128.0 ($C_q$), 126.9 (CH), 126.6 (CH), 125.9 (CH), 67.5 (CH$_2$), 52.4 (CH$_3$), 44.1 (CH$_2$), 43.8 (2CH$_2$), 43.5 (CH$_2$), 41.9 (CH$_2$); MS: m/z=386 [M+H]$^+$;

(e) 1-[4-(adamantane-1-carbonyl)piperazin-1-yl]-2-amino-ethanone (4e)

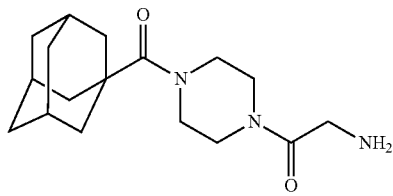 [SMILES: NCC(=O)N1CCN(C(=O)C23CC4CC(CC(C4)C2)C3)CC1]

$C_{17}H_{27}N_3O_2$; yield 47%; white solid; m.p. 231-132° C.; M=305.42 g/mol; IR (ATR): v=2904 (m), 2844 (w), 1697 (w), 1606 (s), 1414 (m), 1226 (m), 1005 (m-s) cm$^{-1}$; $^1$H NMR (250 MHz, CDCl$_3$) δ 3.70-3.62 (m, 6H), 3.47 (s, 2H), 3.38-3.34 (m, 2H), 2.04 (as, 3H), 1.98-1.97 (m, 6H), 1.77-1.66 (m, 6H), 1.60 (s, 2H); $^{13}$C NMR (63 MHz, CDCl$_3$) δ 176.2 ($C_q$), 171.7 ($C_q$), 45.6 (CH$_2$), 44.8 (CH$_2$), 44.4 (CH$_2$), 43.5 (CH$_2$), 42.3 (CH$_2$), 41.9 ($C_q$), 39.2 (3CH$_2$), 36.7 (3CH$_2$), 28.5 (3CH); MS: m/z=306 [M+H]$^+$;

(f) 1-adamantylmethyl 4-(2-aminoacetyl)piperazine-1-carboxylate (4f)

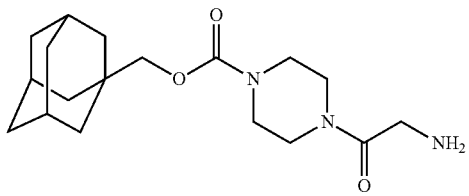 [SMILES: NCC(=O)N1CCN(C(=O)OCC23CC4CC(CC(C4)C2)C3)CC1]

$C_{18}H_{29}N_3O_3$; yield 60%; colorless viscous oil; M=335.44 g/mol; IR (ATR): v=3384 (w), 2901 (m-s), 2847 (m), 1694 (s), 1627 (s), 1457 (m), 1423 (s), 1223 (s) cm$^{-1}$; $^1$H NMR (250 MHz, CDCl$_3$) δ 3.70 (s, 2H), 3.66-3.59 (m, 2H), 3.53-3.48 (m, 6H), 3.41-3.35 (m, 2H), 2.04 (as, 3H), 1.76-1.61 (m, 8H), 1.53 (d, J=2.5 Hz, 6H); $^{13}$C NMR (63 MHz, CDCl$_3$) δ 171.5 ($C_q$), 155.7 ($C_q$), 75.6 (CH$_2$), 44.1 (CH$_2$), 43.6 (2CH$_2$), 43.4 (CH$_2$), 41.9 (CH$_2$), 39.5 (3CH$_2$), 37.1 (3CH$_2$), 33.6 ($C_q$), 28.1 (3CH); MS: m/z=336 [M+H]$^+$;

(g) 2-(1-adamantyl)ethyl 4-(2-aminoacetyl)piperazine-1-carboxylate (4g)

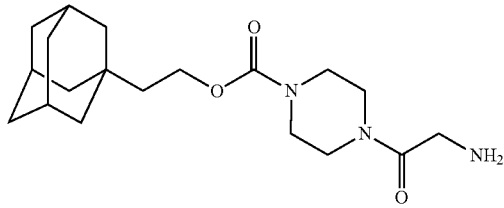 [SMILES: NCC(=O)N1CCN(C(=O)OCCC23CC4CC(CC(C4)C2)C3)CC1]

$C_{19}H_{31}N_3O_3$; yield 72%; light yellow viscous oil becoming light yellow solid on standing; m.p. 58-59° C.; M=349.47 g/mol; IR (ATR): v=3375 (m), 2892 (s), 2844 (m), 1697 (s), 1639 (s), 1448 (m), 1417 (s), 1375 (m), 1220 (s), 1123 (m) cm$^{-1}$; $^1$H NMR (250 MHz, CDCl$_3$) δ 4.15 (t, J=7.2 Hz, 2H), 3.67-3.59 (m, 2H), 3.54-3.48 (m, 6H), 3.37-3.33 (m, 2H), 1.93 (as, 3H), 1.72-1.58 (m, 6H), 1.51 (d, J=2.5 Hz, 6H), 1.42 (t, J=7.3 Hz, 2H); $^{13}$C NMR (63 MHz, CDCl$_3$) δ 171.1 ($C_q$), 155.5 ($C_q$), 62.4 (CH$_2$), 44.2 (CH$_2$), 43.6 (2CH$_2$), 43.2 (CH$_2$), 42.9 (CH$_2$), 42.7 (3CH$_2$), 41.9 (CH$_2$), 37.1 (3CH$_2$), 31.9 ($C_q$), 28.7 (3CH); MS: m/z=350 [M+H]$^+$;

(h) 2-amino-1-[4-[[5-(dimethylamino)-1-naphthyl]sulfonyl]piperazin-1-yl]ethanone (4 h)

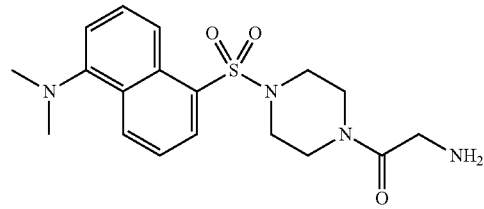 [SMILES: CN(C)c1cccc2c(S(=O)(=O)N3CCN(C(=O)CN)CC3)cccc12]

$C_{18}H_{24}N_4O_3S$; yield 95%; yellow solid; m.p. 82-83° C.; M=376.47 g/mol; IR (ATR): v=3441 (w), 2932 (w), 1654 (m-s), 1636 (m-s), 1451 (m), 1342 (m), 1323 (m), 1156 (s), 1144 (s), 941 (m-s), 896 (m), 789 (s), 707 (s), 619 (m) cm$^{-1}$; $^1$H NMR (250 MHz, CDCl$_3$) δ 8.58 (d, J=8.5 Hz, 1H), 8.36 (d, J=8.7 Hz, 1H), 8.19 (dd, J=7.4 Hz, J=1.2 Hz, 1H), 7.53 (dd, J=8.5 Hz, J=7.6 Hz, 2H), 7.18 (d, J=7.5 Hz, 1H), 3.72-3.57 (m, 2H), 3.50-3.31 (m, 4H), 3.23-3.10 (m, 4H), 2.88 (s, 6H); $^{13}$C NMR (63 MHz, CDCl$_3$) δ 171.2 ($C_q$), 152.0 ($C_q$), 132.2 ($C_q$), 131.2 (CH), 130.9 (CH), 130.4 ($C_q$), 130.2 ($C_q$), 128.4 (CH), 123.3 (CH), 119.4 (CH), 115.5 (CH), 45.6 (CH$_2$), 45.5 (2CH$_3$), 45.5 (CH$_2$), 44.0 (CH$_2$), 43.2 (CH$_2$), 41.6 (CH$_2$); MS: m/z=377 [M+H]$^+$;

(i) benzyl 4-[(2R)-2-aminopropanoyl]piperazine-1-carboxylate (4i)

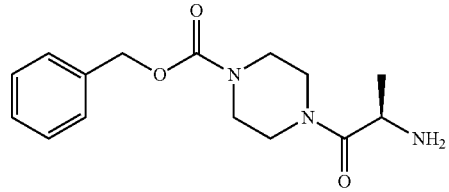 [SMILES: C[C@@H](N)C(=O)N1CCN(C(=O)OCc2ccccc2)CC1]

$C_{15}H_{21}N_3O_3$; colorless viscous oil; yield 41%; M=291.35 g/mol; IR (ATR): v=3372 (w), 2922 (w), 1694 (s), 1639 (s), 1466 (w), 1417 (m-s), 1223 (s), 1117 (m), 1072 (m), 1020 (m), 729 (m), 698 (m) cm$^{-1}$; $^1$H NMR (250 MHz, CDCl$_3$) δ 7.38-7.31 (m, 5H), 5.15 (s, 2H), 3.90-3.36 (m, 9H), 1.83 (s, 2H), 1.25 (d, J=6.7 Hz, 3H); $^{13}$C NMR (63 MHz, CDCl$_3$) δ 174.9 (C$_q$), 155.2 (C$_q$), 136.4 (C$_q$), 128.7 (2CH), 128.4 (CH), 128.2 (2CH), 67.7 (CH$_2$), 47.1 (CH), 45.0 (CH$_2$), 44.0 (CH$_2$), 43.8 (CH$_2$), 42.0 (CH$_2$), 21.7 (CH$_3$); MS: m/z=292 [M+H]$^+$;

(j) benzyl 4-[(2S)-2-aminopropanoyl]piperazine-1-carboxylate (4j)

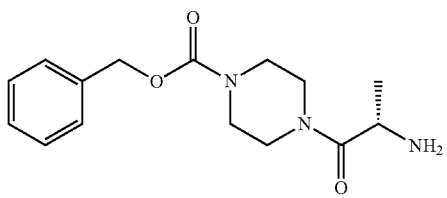 [SMILES: C[C@H](N)C(=O)N1CCN(C(=O)OCc2ccccc2)CC1]

$C_{15}H_{21}N_3O_3$; colorless viscous oil becoming white solid on standing; m.p.: 53-54° C.; yield 35%; M=291.35 g/mol; IR (ATR): v=2965 (w), 1697 (s), 1633 (s), 1420 (s), 1366 (m), 1223 (s), 1129 (m-s), 984 (m), 886 (m), 732 (m) cm$^{-1}$; $^1$H NMR (250 MHz, CDCl$_3$) δ 7.40-7.31 (m, 5H), 5.14 (s, 2H), 3.85-3.36 (m, 9H), 1.81 (s, 2H), 1.25 (d, J=6.8 Hz, 3H); $^{13}$C NMR (63 MHz, CDCl$_3$) δ 174.9 (C$_q$), 155.2 (C$_q$), 136.4 (C$_q$), 128.7 (2CH), 128.4 (CH), 128.2 (2CH), 67.7 (CH$_2$), 47.1 (CH), 45.0 (CH$_2$), 44.0 (CH$_2$), 43.8 (CH$_2$), 41.9 (CH$_2$), 21.8 (CH$_3$); MS: m/z=292 [M+H]$^+$;

(k) benzyl 4-[(2R)-2-amino-3-phenyl-propanoyl]piperazine-1-carboxylate (4k)

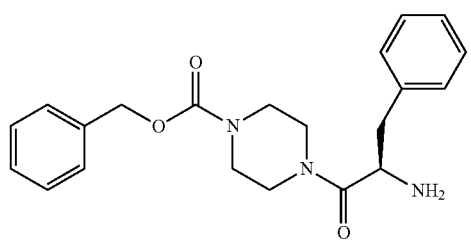 [SMILES: N[C@H](Cc1ccccc1)C(=O)N1CCN(C(=O)OCc2ccccc2)CC1]

$C_{21}H_{25}N_3O_3$; light yellow viscous oil; yield 64%; M=367.44 g/mol; IR (ATR): v=3365 (w), 2913 (w), 1697 (s), 1633 (s), 1427 (m), 1223 (s), 1117 (w), 747 (m), 695 (m-s); $^1$H NMR (250 MHz, CDCl$_3$) δ 7.41-7.16 (m, 10H), 5.10 (s, 2H), 3.94 (as, 1H), 3.66-3.19 (m, 6H), 3.05-2.97 (m, 1H), 2.94-2.81 (m, 2H), 2.76-2.68 (m, 1H), 1.89 (broad s, 2H); MS: m/z=368 [M+H]$^+$;

(l) benzyl 4-[(2S)-2-amino-3-phenyl-propanoyl]perazine-1-carboxylate (4l)

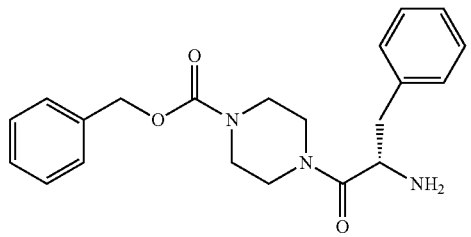 [SMILES: N[C@@H](Cc1ccccc1)C(=O)N1CCN(C(=O)OCc2ccccc2)CC1]

$C_{21}H_{25}N_3O_3$; light yellow viscous oil; yield 46%; M=367.44 g/mol; IR (ATR): v=3372 (w), 2919 (w), 1694 (s), 1636 (s), 1423 (s), 1226 (s), 1114 (m), 741 (m), 692 (s) cm$^{-1}$; $^1$H NMR (250 MHz, CDCl$_3$) δ 7.41-7.16 (m, 10H), 5.11 (CH$_2$), 3.69-2.83 (m, 10H), 2.74-2.67 (m, 1H), 1.76 (broad s, 2H); MS: m/z=368 [M+H]$^+$;

(m) Synthesis of tert-butyl 4-(2-aminoacetyl)piperazine-1-carboxylate (4m)

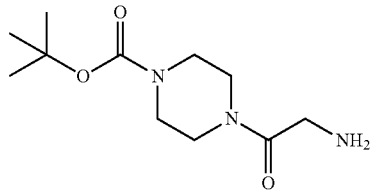 [SMILES: CC(C)(C)OC(=O)N1CCN(C(=O)CN)CC1]

4-(2-bromoacetyl)piperazine-1-carboxylate (9.77 mmol, 1 eq.) in methanol (26 ml) at 0° C. The reaction vial was sealed and the mixture stirred vigorously overnight at room temperature. The solvent was subsequently evaporated, the residue dissolved in hydrogen chloride (aqueous soln., 0.1 N, 100 ml) and extracted with ethyl acetate (3×100 ml). The pH of the recovered aqueous layer was adjusted to 10 by addition of sodium hydroxide (aqueous soln., 1N), then the organics extracted with ethyl acetate (3×100 ml). The combined organic layers were dried over magnesium sulfate, filtered and the solvent evaporated under vacuum to give a light yellow crude product. Further trituration in diethyl ether conducted to the desired amine as a white solid used for the next step without additional purification. $C_{11}H_{21}N_3O_3$; yield 58%; white solid; m.p. 159-160° C.; M=243.30 g/mol; IR (ATR): v=2974 (w), 1675 (s), 1627 (s), 1417 (m), 1360 (m), 1235 (m), 1172 (m), 1123 (m), 990 (m), 759 (m) cm$^{-1}$; $^1$H NMR (250 MHz, CDCl$_3$) δ 3.71-3.41 (m, 10H), 1.46 (s, 9H); $^{13}$C NMR (63 MHz, CDCl$_3$) δ 169.5 (C$_q$), 154.6 (C$_q$), 80.5 (C$_q$), 50.4 (CH$_2$), 44.6 (2CH$_2$), 41.7 (2CH$_2$); HRMS: calcd. for $C_{11}H_{21}N_3O_3$ 244.1661, found. 244.1657.

Synthesis of the Acrylamide Derivatives (E)

Triethylamine (1.25 mmol, 5 eq.) was added to a solution of the previously obtained amine (0.25 mmol, 1 eq.) in acetonitrile (5 ml). The mixture was cooled to 0° C. and acryloyl chloride (0.63 mmol, 2.5 eq.) was subsequently added under nitrogen. After 3 h of stirring at 0° C., the reaction mixture was diluted with ethyl acetate (100 ml) and washed with sodium bicarbonate (satd. aq. soln., 3×50 ml). The recovered organic phase was dried over magnesium sulfate and then the solvent evaporated under reduced pressure to give the crude product.

(a) benzyl 4-[2-(prop-2-enoylamino)acetyl]piperazine-1-carboxylate (5a)

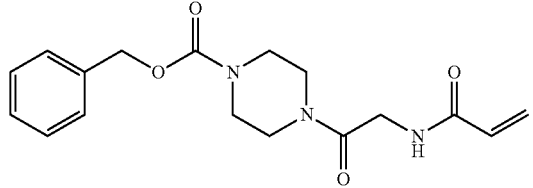 [SMILES: C=CC(=O)NCC(=O)N1CCN(C(=O)OCc2ccccc2)CC1]

The crude derivative obtained following the general protocol described before was subsequently purified by flash chromatography (eluent: DCM/MeOH 96/4). $C_{17}H_{21}N_3O_4$; yield 56%; colorless viscous oil; M=331.37 g/mol; IR (ATR): ν=3004 (w), 1691 (s), 1636 (s), 1420 (s), 1223 (s), 744 (s) cm$^{-1}$; $^1$H NMR (250 MHz, CDCl$_3$) δ 7.42-7.32 (m, 5H), 6.73 (as, 1H), 6.32 (dd, J=17.0 Hz, J=1.9 Hz, 1H), 6.18 (dd, J=17.0 Hz, J=9.8 Hz, 1H), 5.68 (dd, J=9.8 Hz, J=1.9 Hz, 1H), 5.15 (s, 2H), 4.15 (d, J=4.0 Hz, 2H), 3.70-3.62 (m, 2H), 3.57-3.50 (m, 4H), 3.43-3.36 (m, 2H); $^{13}$C NMR (63 MHz, CDCl$_3$) δ 166.8 ($C_q$), 165.5 ($C_q$), 155.2 ($C_q$), 136.3 ($C_q$), 130.4 (CH), 128.7 (2CH), 128.4 (CH), 128.2 (2CH), 127.1 (CH$_2$), 67.8 (CH$_2$), 44.4 (CH$_2$), 43.7 (CH$_2$), 43.6 (CH$_2$), 41.9 (CH$_2$), 41.4 (CH$_2$); MS: m/z=354 [M+Na]$^+$; HRMS: calcd. for $C_{17}H_{22}O_4N_3$ 332.1605, found 332.1610 (1.6 ppm).

(b) (4-methoxycarbonylphenyl)methyl 4-[2-(prop-2-enoylamino)acetyl]piperazine-1-carboxylate (5b)

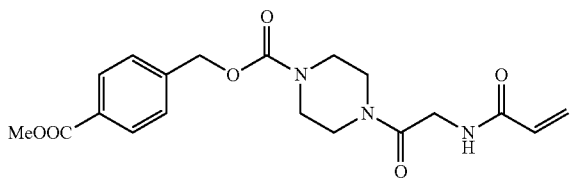 [SMILES: C=CC(=O)NCC(=O)N1CCN(C(=O)OCc2ccc(C(=O)OC)cc2)CC1]

The crude derivative obtained following the general protocol described before was subsequently purified by flash chromatography (eluent: DCM/MeOH 97/3). $C_{19}H_{23}N_3O_6$; yield 60%; white solid; m.p. 159-160° C.; M=389.40 g/mol; IR (ATR): ν=3284 (w), 2898 (w), 1703 (s), 1648 (s), 1427 (s), 1278 (m), 1214 (m), 1105 (m), 759 (m) cm$^{-1}$; $^1$H NMR (250 MHz, CDCl$_3$) δ 8.04 (d, J=8.4 Hz, 2H), 7.42 (d, J=8.4 Hz, 2H), 6.68 (as, 1H), 6.33 (dd, J=17.0 Hz, J=1.9 Hz, 1H), 6.18 (dd, J=17.0 Hz, 9.9 Hz, 1H), 5.69 (dd, J=9.8 Hz, J=1.9 Hz, 1H), 5.21 (s, 2H), 4.15 (d, J=4.1 Hz, 2H), 3.92 (s, 3H), 3.68-3.63 (m, 2H), 3.59-3.52 (m, 4H), 3.49-3.39 (m, 2H); $^{13}$C NMR (63 MHz, CDCl$_3$) δ 166.8 ($C_q$), 165.5 ($C_q$), 154.9 ($C_q$), 141.4 ($C_q$), 130.4 (CH), 130.2 ($C_q$), 130.0 (2CH), 127.7 (2CH), 127.0 (CH$_2$), 67.0 (CH$_2$), 52.3 (CH$_3$), 44.3 (CH$_2$), 43.8 (CH$_2$), 43.7 (CH$_2$), 41.9 (CH$_2$), 41.4 (CH$_2$); MS: m/z=412 [M+Na]$^+$; HRMS: calcd. for $C_{19}H_{24}O_6N_3$ 390.1660, found 390.1663 (0.9 ppm).

(c) 2-naphthylmethyl 4-[2-(prop-2-enoylamino)acetyl]piperazine-1-carboxylate (5c)

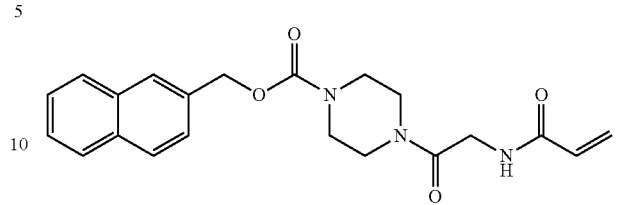

The crude derivative obtained following the general protocol described before was subsequently purified by flash chromatography (eluent: EtOAc). $C_{21}H_{23}N_3O_4$; yield 59%; white solid; m.p. 125-126° C.; M=381.43 g/mol; IR (ATR): ν=3332 (w), 2925 (w), 1703 (s), 1663 (m), 1642 (s), 1621 (s), 1460 (m), 1436 (m), 1417 (m), 1220 (s), 817 (w), 750 (w) cm$^{-1}$; $^1$H NMR (250 MHz, CDCl$_3$) δ 7.86-7.82 (m, 4H), 7.53-7.54 (m, 3H), 6.71 (as, 1H), 6.31 (dd, J=17.0 Hz, J=2.0 Hz, 1H), 6.18 (dd, J=17.0 Hz, J=9.7 Hz, 1H), 5.67 (dd, J=9.7 Hz, J=2.0 Hz, 1H), 5.32 (s, 2H), 4.14 (d, J=4.0 Hz, 2H), 3.65-3.42 (m, 8H); $^{13}$C NMR (63 MHz, CDCl$_3$) δ 166.7 ($C_q$), 165.5 ($C_q$), 155.2 ($C_q$), 133.7 ($C_q$), 133.3 ($C_q$), 133.3 ($C_q$), 130.4 (CH), 128.6 (CH), 128.1 (CH), 127.9 (CH), 127.5 (CH), 127.1 (CH$_2$), 126.5 (CH), 126.5 (CH), 126.0 (CH), 68.0 (CH$_2$), 44.4 (CH$_2$), 43.8 (CH$_2$), 43.6 (CH$_2$), 41.9 (CH$_2$), 41.4 (CH$_2$); MS: m/z=404 [M+Na]$^+$; HRMS: calcd. for $C_{21}H_{24}O_4N_3$ 382.1761, found 382.1765 (1.0 ppm).

(d) (6-methoxycarbonyl-2-naphthyl)methyl 4-[2-(prop-2-enoylamino)acetyl]piperazine-1-carboxylate (5d)

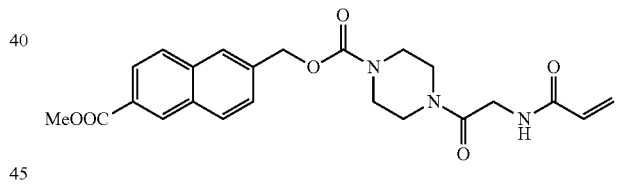

The crude derivative obtained following the general protocol described before was subsequently purified by flash chromatography (eluent: EtOAc). $C_{23}H_{25}N_3O_6$; yield 71%; white solid; m.p. 159-160° C.; M=439.46 g/mol; IR (ATR): ν=3338 (w), 2938 (w), 1697 (s), 1666 (s), 1648 (s), 1618 (s), 1430 (s), 1290 (s), 1217 (m), 1123 (m), 804 (s) cm$^{-1}$; $^1$H NMR (250 MHz, CDCl$_3$) δ 8.60 (s, 1H), 8.08 (dd, J=8.6 Hz, J=1.7 Hz, 1H), 7.96 (d, J=8.5 Hz, 1H), 7.88 (d, J=8.7 Hz, 1H), 7.85 (s, 1H), 7.53 (dd, J=8.5 Hz, J=1.6 Hz, 1H), 6.70 (as, 1H), 6.32 (dd, J=17.0 Hz, J=1.9 Hz, 1H), 6.18 (dd, J=17.0 Hz, J=9.8 Hz, 1H), 5.68 (dd, J=9.8 Hz, J=1.9 Hz, 1H), 5.33 (s, 2H), 4.15 (d, J=4.1 Hz, 2H), 3.98 (s, 3H), 3.68-3.64 (m, 2H), 3.60-3.53 (m, 4H), 3.50-3.38 (m, 2H); $^{13}$C NMR (63 MHz, CDCl$_3$) δ 167.2 ($C_q$), 166.8 ($C_q$), 165.5 ($C_q$), 155.1 ($C_q$), 136.4 ($C_q$), 135.5 ($C_q$), 132.2 ($C_q$), 130.9 (CH), 130.4 (CH), 130.0 (CH), 128.4 (CH), 128.0 ($C_q$), 127.1 (CH$_2$), 127.0 (CH), 126.6 (CH), 125.9 (CH), 67.6 (CH$_2$), 52.4 (CH$_3$), 44.3 (CH$_2$), 43.8 (CH$_2$), 43.7 (CH$_2$), 41.9 (CH$_2$), 41.4 (CH$_2$); MS: m/z=462 [M+Na]$^+$; HRMS: calcd. for $C_{23}H_{26}O_6N_3$ 440.1816. found 440.1814 (0.5 ppm).

(e) N-[2-[4-(adamantane-1-carbonyl)piperazin-1-yl]-2-oxo-ethyl]prop-2-enamide (5e)

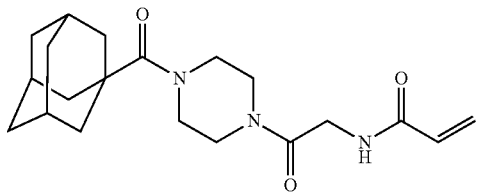 [SMILES: C=CC(=O)NCC(=O)N1CCN(C(=O)C23CC4CC(CC(C4)C2)C3)CC1]

The crude derivative obtained following the general protocol described before was subsequently purified by flash chromatography (eluent: EtOAc).C$_{20}$H$_{29}$N$_3$O$_3$; yield 41%; white solid; m.p. 195-196° C.; M=359.46 g/mol; IR (ATR): v=3311 (w), 2910 (m), 1675 (m-s), 1642 (m), 1599 (s), 1557 (m), 1417 (m), 1223 (s), 1008 (m-s), 947 (m) cm$^{-1}$; $^1$H NMR (250 MHz, CDCl$_3$) δ 6.68 (as, 1H), 6.32 (dd, J=17.0 Hz, J=1.9 Hz, 1H), 6.18 (dd, J=17.0 Hz, J=9.9 Hz, 1H), 5.69 (dd, J=9.8 Hz, J=1.9 Hz, 1H), 4.15 (d, J=4.1 Hz, 2H), 3.75-3.71 (m, 4H), 3.66-3.63 (m, 2H), 3.45-3.41 (m, 2H), 2.06 (as, 3H), 1.99-1.98 (m, 6H), 1.79-1.68 (m, 6H); $^{13}$C NMR (63 MHz, CDCl$_3$) δ 176.3 (C$_q$), 166.8 (C$_q$), 165.5 (C$_q$), 130.5 (CH), 127.1 (CH$_2$), 45.3 (CH$_2$), 44.9 (CH$_2$), 44.7 (CH$_2$), 42.4 (CH$_2$), 42.0 (C$_q$), 41.4 (CH$_2$), 39.2 (3CH$_2$), 36.7 (3CH$_2$), 28.5 (3CH); MS: m/z=382 [M+Na]$^+$; HRMS: calcd. for C$_{20}$H$_{30}$O$_3$N$_3$ 360.2282. found 360.2287 (1.5 ppm).

(f) 1-adamantylmethyl 4-[2-(prop-2-enoylamino)acetyl]perazine-1-carboxylate (5f)

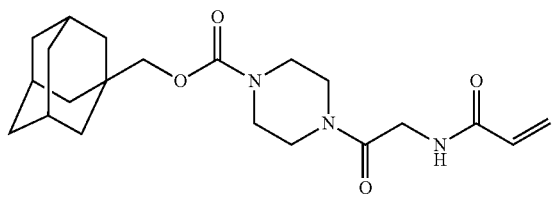 [SMILES: C=CC(=O)NCC(=O)N1CCN(C(=O)OCC23CC4CC(CC(C4)C2)C3)CC1]

The crude derivative obtained following the general protocol described before was subsequently purified by flash chromatography (eluent: EtOAc). C$_{21}$H$_{31}$N$_3$O$_4$; yield 48%; white solid; m.p. 176-177° C.; M=389.49 g/mol; IR (ATR): v=3335 (w), 2892 (m), 2844 (w), 1687 (s), 1672 (m), 1621 (s), 1469 (m), 1420 (s), 1251 (m), 1223 (s) cm$^{-1}$; $^1$H NMR (250 MHz, CDCl$_3$) δ 6.70 (as, 1H), 6.32 (dd, J=17.0 Hz, J=1.9 Hz, 1H), 6.18 (dd, J=17.0 Hz, J=9.8 Hz, 1H), 5.68 (dd, J=9.8 Hz, J=1.9 Hz, 1H), 4.16 (d, J=4.1 Hz, 2H), 3.71 (s, 2H), 3.68-3.62 (m, 2H), 3.56-3.49 (m, 4H), 3.46-3.42 (m, 2H), 1.99 (as, 3H), 1.77-1.62 (m, 6H), 1.53 (d, J=2.5 Hz, 6H); $^{13}$C NMR (63 MHz, CDCl$_3$) δ 166.8 (C$_q$), 165.5 (C$_q$), 155.7 (C$_q$), 130.5 (CH), 127.1 (CH$_2$), 75.7 (CH$_2$), 44.4 (CH$_2$), 43.7 (CH$_2$), 43.5 (CH$_2$), 42.0 (CH$_2$), 41.5 (CH$_2$), 39.5 (3CH$_2$), 37.1 (3CH$_2$), 33.6 (C$_q$), 28.1 (3CH); MS: m/z=412 [M+Na]$^+$; HRMS: calcd. for C$_{21}$H$_{32}$O$_4$N$_3$ 390.2387, found 390.2391 (0.9 ppm).

(g) 2-(1-adamantyl)ethyl 4-[2-(prop-2-enoylamino)acetyl]piperazine-1-carboxylate (5g)

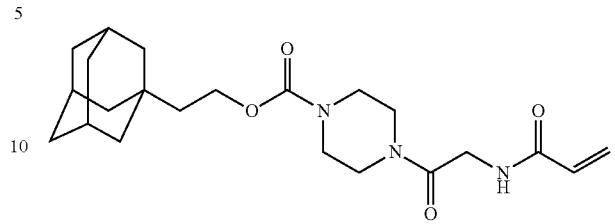

The crude derivative obtained following the general protocol described before was subsequently purified by flash chromatography (eluent: EtOAc). C$_{22}$H$_{33}$N$_3$O$_4$; yield 54%; white solid; m.p. 155-156° C.; M=403.52 g/mol; IR (ATR): v=3317 (w), 2901 (m-s), 2847 (w), 1684 (s), 1624 (s), 1469 (m), 1427 (s), 1223 (s) cm$^{-1}$; $^1$H NMR (250 MHz, CDCl$_3$) δ 6.73 (as, 1H), 6.32 (dd, J=17.0 Hz, J=1.9 Hz, 1H), 6.18 (dd, J=17.0 Hz, J=9.8 Hz, 1H), 5.68 (dd, J=9.8 Hz, J=1.9 Hz, 1H), 4.19-4.13 (m, 4H), 3.65-3.61 (m, 2H), 3.50-3.46 (m, 4H), 3.43-3.39 (m, 2H), 1.94 (as, 3H), 1.73-1.59 (m, 6H), 1.52 (d, J=2.4 Hz, 6H), 1.43 (t, J=7.3 Hz, 2H); $^{13}$C NMR (63 MHz, CDCl$_3$) δ 166.7 (C$_q$), 165.5 (C$_q$), 155.5 (C$_q$), 130.5 (CH), 127.0 (CH$_2$), 62.5 (CH$_2$), 44.4 (CH$_2$), 43.6 (CH$_2$), 43.5 (CH$_2$), 42.9 (CH$_2$), 42.7 (3CH$_2$), 42.0 (CH$_2$), 41.4 (CH$_2$), 37.1 (3CH$_2$), 31.9 (C$_q$), 28.7 (3CH); MS: m/z=426 [M+Na]$^+$; HRMS: calcd. for C$_{22}$H$_{34}$O$_4$N$_3$ 404.2544, found 404.2547 (0.8 ppm).

(h) N-[2-[4-[[5-(dimethylamino)-1-naphthyl]sulfonyl]piperazin-1-yl]-2-oxo-ethyl]prop-2-enamide (5h)

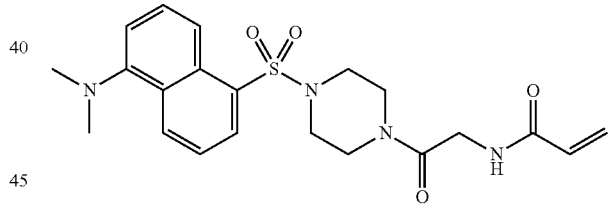

The crude derivative obtained following the general protocol described before was subsequently purified by flash chromatography (eluent: EtOAc). C$_{18}$H$_{24}$N$_4$O$_3$S; yield 39%; light yellow solid; m.p. 185-186° C.; M=430.52 g/mol; IR (ATR): v=2935 (w), 1651 (s), 1454 (m), 1436 (m), 1311 (m), 1141 (s), 941 (s), 789 (s), 704 (m) cm$^{-1}$; $^1$H NMR (250 MHz, CDCl$_3$) δ 8.59 (d, J=8.5 Hz, 1H), 8.35 (d, J=8.7 Hz, 1H), 8.21 (dd, J=7.4 Hz, J=1.2 Hz, 1H), 7.55 (dd, J=8.5 Hz, J=7.5 Hz, 2H), 7.19 (d, J=7.5 Hz, 1H), 6.58 (as, 1H), 6.28 (dd, J=17.0 Hz, J=1.8 Hz, 1H), 6.13 (dd, J=17.0 Hz, J=9.9 Hz, 1H), 5.65 (dd, J=9.9 Hz, J=1.8 Hz, 1H), 4.05 (d, J=4.1 Hz, 2H), 3.68 (t, J=5.1 Hz, 2H), 3.47 (t, J=5.0 Hz, 2H), 3.21 (dt, J=9.8 Hz, J=4.7 Hz, 4H), 2.89 (s, 6H); $^{13}$C NMR (63 MHz, CDCl$_3$) δ 166.5 (C$_q$), 165.4 (C$_q$), 152.1 (C$_q$), 132.2 (C$_q$), 131.4 (CH), 131.0 (CH), 130.4 (C$_q$), 130.3 (CH), 130.3 (C$_q$), 128.5 (CH), 127.1 (CH$_2$), 123.3 (CH), 119.3 (CH), 115.6 (CH), 45.6 (CH$_2$), 45.6 (2CH$_2$), 45.4 (CH$_2$), 44.3 (CH$_2$), 41.8 (CH$_2$), 41.3 (CH$_2$); MS: m/z=453 [M+Na]$^+$; HRMS: calcd. for C$_{21}$H$_{27}$O$_4$N$_4$S, 431.1748. found 431.1751 (0.8 ppm).

(i) benzyl 4-[(2R)-2-(prop-2-enoylamino)propanoyl]piperazine-1-carboxylate (5i)

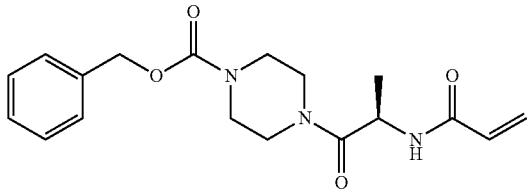 [SMILES: C=CC(=O)N[C@H](C)C(=O)N1CCN(C(=O)OCc2ccccc2)CC1]

The crude derivative obtained following the general protocol described before was subsequently purified by flash chromatography (eluent: EtOAc). $C_{18}H_{23}N_3O_4$; colorless viscous oil; yield 73%; M=345.39 g/mol; IR (ATR): ν=3290 (w), 2929 (w), 1697 (s), 1621 (s), 1423 (s), 1220 (s), 1020 (m), 759 (m), 695 (m) cm$^{-1}$; $^1$H NMR (250 MHz, CDCl$_3$) δ 7.41-7.32 (m, 5H), 6.71 (d, J=7.1 Hz, 1H), 6.30 (dd, J=17.0 Hz, J=1.7 Hz, 1H), 6.12 (dd, J=17.0 Hz, J=10.0 Hz, 1H), 5.66 (dd, J=10.0 Hz, J=1.7 Hz, 1H), 5.15 (s, 2H), 4.96 (p, J=6.9 Hz, 1H), 3.79-3.40 (m, 8H), 1.36 (d, J=6.8 Hz, 3H); $^{13}$C NMR (63 MHz, CDCl$_3$) δ 171.2 ($C_q$), 164.7 ($C_q$), 155.2 ($C_q$), 136.4 ($C_q$), 130.7 (CH), 128.7 (2CH), 128.4 (CH), 128.2 (2CH), 127.0 (CH$_2$), 67.7 (CH$_2$), 45.4 (CH$_2$), 45.3 (CH), 44.0 (CH$_2$), 43.7 (CH$_2$), 42.1 (CH$_2$), 19.2 (CH$_3$); MS: m/z=368 [M+Na]$^+$; HRMS: calcd. for $C_{18}H_{24}O_4N_3$ 346.1761, found 346.1767 (1.6 ppm).

(j) benzyl 4-[(2S)-2-(prop-2-enoylamino)propanoyl]perazine-1-carboxylate (5j)

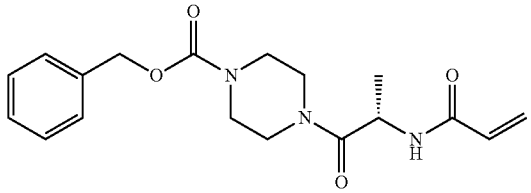 [SMILES: C=CC(=O)N[C@@H](C)C(=O)N1CCN(C(=O)OCc2ccccc2)CC1]

The crude derivative obtained following the general protocol described before was subsequently purified by flash chromatography (eluent: EtOAc). $C_{18}H_{23}N_3O_4$; white solid; m.p. 121-122° C.; yield 72%; M=345.39 g/mol; IR (ATR): ν=3271 (w), 2929 (w), 1697 (s), 1624 (s), 1423 (s), 1223 (s), 1117 (w-m), 1011 (m), 759 (m), 695 (m) cm$^{-1}$; $^1$H NMR (250 MHz, CDCl$_3$) δ 7.40-7.35 (m, 5H), 6.71 (d, J=7.1 Hz, 1H), 6.29 (dd, J=17.0 Hz, J=1.6 Hz, 1H), 6.12 (dd, J=17.0 Hz, J=10.0 Hz, 1H), 5.66 (dd, J=10.0 Hz, J=1.6 Hz, 1H), 5.15 (d, 2H), 4.96 (p, J=7.0 Hz, 1H), 3.81-3.40 (m, 8H), 1.35 (d, J=6.8 Hz, 3H); $^{13}$C NMR (63 MHz, CDCl$_3$) δ 171.1 ($C_q$), 164.6 ($C_q$), 155.1 ($C_q$), 136.3 ($C_q$), 130.7 (CH), 128.7 (2CH), 128.4 (CH), 128.2 (2CH), 127.0 (CH$_2$), 67.7 (CH$_2$), 45.3 (CH$_2$), 45.2 (CH), 43.9 (CH$_2$), 43.6 (CH$_2$), 42.0 (CH$_2$), 19.2 (CH$_3$); MS: m/z=368 [M+Na]$^+$; HRMS: calcd. for $C_{18}H_{24}O_4N_3$ 346.1761, found 346.1767 (1.6 ppm).

(k) benzyl 4-[(2R)-3-phenyl-2-(prop-2-enoylamino)propanoyl]piperazine-1-carboxylate (5k)

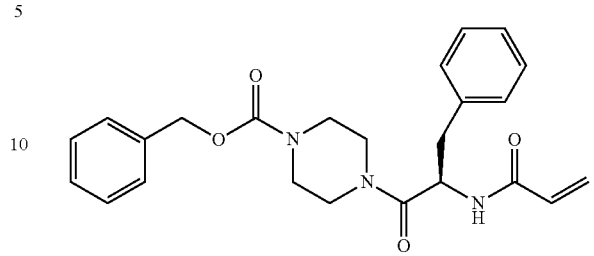

The crude derivative obtained following the general protocol described before was subsequently purified by flash chromatography (eluent: EtOAc). $C_{24}H_{27}N_3O_4$; colorless viscous oil; yield 79%; M=421.49 g/mol; IR (ATR): ν=3284 (w), 2929 (w), 1700 (s), 1621 (s), 1423 (s), 1220 (s), 729 (m), 692 (m) cm$^{-1}$; $^1$H NMR (250 MHz, CDCl$_3$) δ 7.41-7.18 (m, 10H), 6.77 (d, J=8.0 Hz, 1H), 6.31 (dd, J=17.0 Hz, J=1.6 Hz, 1H), 6.12 (dd, J=17.0 Hz, J=10.1 Hz, 1H), 5.67 (dd, J=10.1 Hz, J=1.6 Hz, 1H), 5.20 (td, J=9.0 Hz, J=5.3 Hz, 1H), 5.10 (s, 2H), 3.59-2.92 (m, 9H), 2.68-2.58 (m, 1H); $^{13}$C NMR (63 MHz, CDCl$_3$) δ 170.2 ($C_q$), 164.9 ($C_q$), 155.0 ($C_q$), 136.4 ($C_q$), 136.0 ($C_q$), 130.5 (CH), 129.6 (2CH), 128.8 (2CH), 128.7 (2CH), 128.3 (CH), 128.1 (2CH), 127.5 (CH), 127.3 (CH$_2$), 67.6 (CH$_2$), 49.9 (CH), 45.4 (CH$_2$), 43.3 (2CH$_2$), 41.8 (CH$_2$), 40.1 (CH$_2$); MS: m/z=444 [M+Na]$^+$; HRMS: calcd. for $C_{24}H_{28}O_4N_3$ 422.2074, found 422.2077 (0.6 ppm).

(l) benzyl 4-[(2S)-3-phenyl-2-(prop-2-enoylamino)propanoyl]piperazine-1-carboxylate (5f)

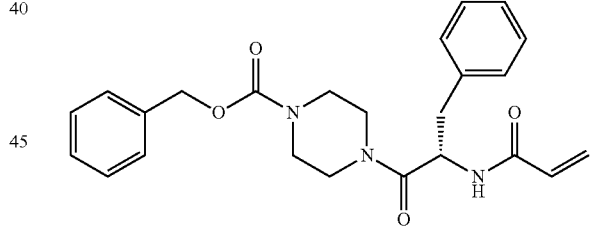

The crude derivative obtained following the general protocol described before was subsequently purified by flash chromatography (eluent: EtOAc). $C_{24}H_{27}N_3O_4$; colorless viscous oil; yield 65%; M=421.49 g/mol; IR (ATR): ν=3287 (w), 2925 (w), 1697 (s), 1621 (s), 1423 (s), 1220 (s), 1123 (w), 729 (m), 695 (m) cm$^{-1}$; $^1$H NMR (250 MHz, CDCl$_3$) δ 7.41-7.18 (m, 10H), 6.77 (d, J=8.0 Hz, 1H), 6.31 (dd, J=17.0 Hz, J=1.6 Hz, 1H), 6.12 (dd, J=17.0 Hz, J=10.1 Hz, 1H), 5.67 (dd, J=10.1 Hz, J=1.6 Hz, 1H), 5.23 (td, J=9.0 Hz, J=5.3 Hz, 1H), 5.10 (s, 2H), 3.64-2.92 (m, 9H), 2.68-2.58 (m, 1H); $^{13}$C NMR (63 MHz, CDCl$_3$) δ 170.2 ($C_q$), 164.9 ($C_q$), 155.0 ($C_q$), 136.4 ($C_q$), 136.0 ($C_q$), 130.5 (CH), 129.6 (2CH), 128.8 (2CH), 128.7 (2CH), 128.3 (CH), 128.1 (2CH), 127.5 (CH), 127.3 (CH$_2$), 67.6 (CH$_2$), 49.9 (CH), 45.4 (CH$_2$), 43.3 (2CH$_2$), 41.8 (CH$_2$), 40.1 (CH$_2$); MS: m/z=444 [M+Na]$^+$; HRMS: calcd. for $C_{24}H_{28}O_4N_3$ 422.2074, found 422.2077 (0.6 ppm).

General Method for the Acetylation Step (F)

Under inert atmosphere and at −78° C., the corresponding acetylation reagent, bromoacetyl bromide or chloroacetyl chloride, (1.65 mmol, 1.1 eq.) was slowly added to a solution of the corresponding amine (1.5 mmol, 1 eq.) and TEA (7.5 mmol, 5 eq.) in DCM (15 ml). The reaction mixture was stirred at −78° C. for 3 h, diluted with DCM (75 ml) and washed with hydrogen chloride (aq. soln. 0.2 M, 3×50 ml). The recovered organic layer was dried over magnesium sulfate and the solvent was evaporated under vacuum to give the crude product.

(a) benzyl 4-[2-[(2-bromoacetyl)amino]acetyl]perazine-1-carboxylate (6a)

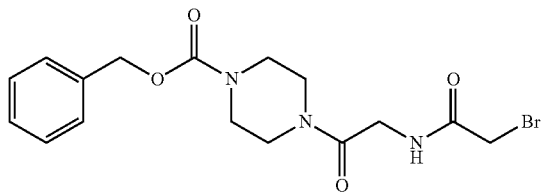 [SMILES: O=C(CBr)NCC(=O)N1CCN(C(=O)OCc2ccccc2)CC1]

The crude derivative obtained using the general protocol described previously was further triturated in diethyl ether to give the desired acetylated compound as a solid. $C_{16}H_{20}BrN_3O_4$; yield 84%; white solid; m.p. 132-133° C.; M=398.25 g/mol; IR (ATR): v=3344 (w), 2904 (w), 1681 (s), 1621 (s), 1478 (m), 1423 (s), 1263 (m-s), 1223 (s), 750 (m) cm$^{-1}$; $^1$H NMR (250 MHz, CDCl$_3$) δ 7.51 (as, 1H), 7.38-7.32 (m, 5H), 5.15 (s, 2H), 4.08 (d, J=4.1 Hz, 2H), 3.89 (s, 2H), 3.70-3.62 (m, 2H), 3.57-3.48 (m, 4H), 3.46-3.32 (m, 2H); $^{13}$C NMR (63 MHz, CDCl$_3$) δ 166.1 ($C_q$), 165.8 ($C_q$), 155.1 ($C_q$), 136.3 ($C_q$), 128.7 (2CH), 128.4 (CH), 128.2 (2CH), 67.8 (CH$_2$), 44.3 (CH$_2$), 43.7 (CH$_2$), 43.6 (CH$_2$), 42.0 (CH$_2$), 41.9 (CH$_2$), 28.6 (CH$_2$); MS: m/z=420 [M+Na]$^+$ for $^{79}$Br and 422 [M+Na] for $^{81}$Br; HRMS: calcd. for $C_{16}H_{21}O_4N_3Br$, 398.0710. found 398.0713 (0.8 ppm).

(b) (4-methoxycarbonylphenyl)methyl 4-[2-[(2-bromoacetyl)amino]acetyl]perazine-1-carboxylate (6b)

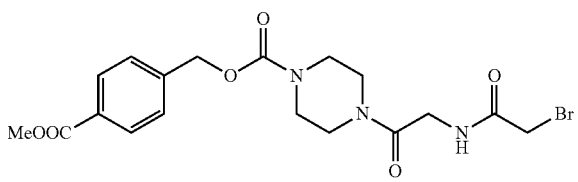 [SMILES: COC(=O)c1ccc(COC(=O)N2CCN(C(=O)CNC(=O)CBr)CC2)cc1]

The crude derivative obtained using the general protocol described previously was further triturated in diethyl ether to give the desired acetylated compound as a solid. $C_{18}H_{22}BrN_3O_6$; yield 95%; light beige solid, m.p. 134-135° C.; M=456.29 g/mol; IR (ATR): v=3284 (m), 2898 (w), 1715 (m), 1697 (s), 1675 (m), 1642 (s), 1433 (m), 1278 (m), 1223 (s), 1102 (m), 1026 (m), 759 (s) cm$^{-1}$; $^1$H NMR (250 MHz, CDCl$_3$) δ 8.04 (d, J=8.4 Hz, 2H), 7.51 (as, 1H), 7.41 (d, J=8.4 Hz, 2H), 5.20 (s, 2H), 4.09 (d, J=4.1 Hz, 2H), 3.92 (s, 3H), 3.90 (s, 2H), 3.68-3.62 (m, 2H), 3.59-3.52 (m, 4H), 3.46-3.36 (m, 2H); $^{13}$C NMR (63 MHz, CDCl$_3$) δ 166.2 ($C_q$), 165.9 ($C_q$), 154.9 ($C_q$), 141.3 ($C_q$), 130.2 ($C_q$), 130.1 (2CH), 127.8 (2CH), 67.0 (CH$_2$), 52.3 (CH$_3$), 44.3 (CH$_2$), 43.8 (CH$_2$), 43.7 (CH$_2$), 41.9 (2CH$_2$), 28.6 (CH$_2$); MS: m/z=480 [M+Na]$^+$; HRMS: calcd. for $C_{18}H_{23}O_6N_3Br$, 456.0765. found 456.0768 (0.7 ppm).

(c) 2-naphthylmethyl 4-[2-[(2-bromoacetyl)amino]acetyl]perazine-1-carboxylate (6c)

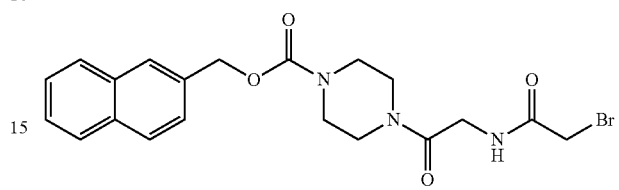

The crude derivative obtained using the general protocol described previously was further triturated in diethyl ether to give the desired acetylated compound as a solid. $C_{20}H_{22}BrN_3O_4$; yield 77%; light beige solid; m.p. 133-134° C.; M=448.31 g/mol; IR (ATR): v=3338 (w), 2922 (w), 1687 (s), 1621 (s), 1478 (w), 1423 (s), 1217 (s), 826 (w), 765 (m) cm$^{-1}$; $^1$H NMR (250 MHz, CDCl$_3$) δ 7.87-7.83 (m, 4H), 7.52-7.45 (m, 4H), 5.31 (s, 2H), 4.08 (d, J=4.0 Hz, 2H), 3.90 (s, 2H), 3.66-3.40 (m, 8H); $^{13}$C NMR (63 MHz, CDCl$_3$) δ 166.1 ($C_q$), 165.8 ($C_q$), 155.2 ($C_q$), 133.7 ($C_q$), 133.3 (2$C_q$), 128.6 (CH), 128.1 (CH), 127.9 (CH), 127.5 (CH), 126.5 (CH), 126.5 (CH), 126.0 (CH), 68.0 (CH$_2$), 44.3 (CH$_2$), 43.7 (CH$_2$), 43.6 (CH$_2$), 42.0 (CH$_2$), 41.9 (CH$_2$), 28.6 (CH$_2$); MS: m/z=472 [M+Na]$^+$; HRMS: calcd. for $C_{20}H_{23}O_4N_3Br$, 448.0866. found 448.0867 (0.1 ppm).

(d) (6-methoxycarbonyl-2-naphthyl)methyl 4-[2-[(2-bromoacetyl)amino]acetyl]perazine-1-carboxylate (6d)

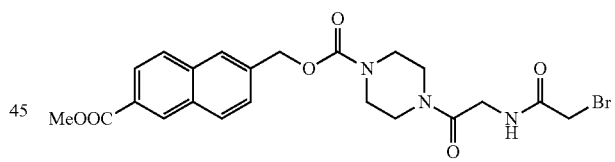

The crude derivative obtained using the general protocol described previously was further triturated in diethyl ether to give the desired acetylated compound as a solid. $C_{22}H_{24}BrN_3O_6$; yield 80%; white solid; m.p. 136-137° C.; M=506.35 g/mol; IR (ATR): v=3326 (w), 2916 (w), 1706 (s), 1621 (s), 1423 (s), 1214 (m), 1202 (m), 814 (m) cm$^{-1}$; $^1$H NMR (250 MHz, CDCl$_3$) δ 8.61 (s, 1H), 8.08 (dd, J=8.6 Hz, J=1.6 Hz, 1H), 7.96 (d, J=8.5 Hz, 1H), 7.88 (d, J=8.7 Hz, 1H), 7.85 (s, 1H), 7.53 (dd, J=8.5 Hz, 1H), 7.53-7.47 (m, 1H), 5.33 (s, 2H), 4.09 (d, J=4.1 Hz, 2H), 3.98 (s, 3H), 3.90 (s, 2H), 3.69-3.65 (m, 2H), 3.60-3.54 (m, 4H), 3.43-3.36 (m, 2H); $^{13}$C NMR (63 MHz, CDCl$_3$) δ 167.2 ($C_q$), 166.1 ($C_q$), 165.9 ($C_q$), 155.1 ($C_q$), 136.4 ($C_q$), 135.5 ($C_q$), 132.3 ($C_q$), 130.9 (CH), 130.0 (CH), 128.4 (CH), 128.0 ($C_q$), 127.0 (CH), 126.6 (CH), 125.9 (CH), 67.6 (CH$_2$), 52.4 (CH$_3$), 44.3 (CH$_2$), 43.7 (CH$_2$), 43.7 (CH$_2$), 42.0 (CH$_2$), 41.9 (CH$_2$), 28.6 (CH$_2$); MS: m/z=528 [M+Na]$^+$ for $^{79}$Br and 530 [M+Na]$^-$ for $^{81}$Br; HRMS: calcd. for $C_{22}H_{25}O_6N_3Br$, 506.0921. found 506.0918 (0.6 ppm).

(e) 2-N-[2-[4-(adamantane-1-carbonyl)piperazin-1-yl]-2-oxo-ethyl]-2-bromo-acetamide (6e)

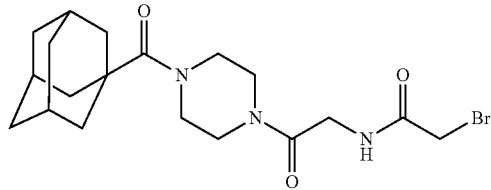 [SMILES: O=C(CBr)NCC(=O)N1CCN(C(=O)C23CC4CC(CC(C4)C2)C3)CC1]

The crude derivative obtained using the general protocol described previously was further triturated in diethyl ether to give the desired acetylated compound as a solid. $C_{19}H_{28}BrN_3O_3$; yield 86%; white solid; m.p. 203-204° C.; M=426.35 g/mol; IR (ATR): v=3305 (m-s), 2932 (m-s), 1681 (s), 1645 (s), 1590 (s), 1563 (m), 1420 (s), 1223 (s), 1205 (m-s), 1014 (s) cm$^{-1}$; $^1$H NMR (250 MHz, CDCl$_3$) δ 7.50 (as, 1H), 4.09 (d, J=4.1 Hz, 2H), 3.90 (s, 2H), 3.74-3.70 (m, 4H), 3.66-3.63 (m, 2H), 3.43-3.39 (m, 2H), 2.06 (as, 3H), 1.99-1.97 (m, 6H), 1.79-1.67 (m, 6H); $^{13}$C NMR (63 MHz, CDCl$_3$) δ 176.3 ($C_q$), 166.2 ($C_q$), 165.8 ($C_q$), 45.4 (CH$_2$), 44.8 (CH$_2$), 44.7 (CH$_2$), 42.4 (CH$_2$), 41.9 (CH$_2$), 41.9 ($C_q$), 39.2 (3CH$_2$), 36.7 (3CH$_2$), 28.6 (CH$_2$), 28.5 (3CH); MS: m/z=448 [M+Na]$^+$ for $^{79}$Br and 450 [M+Na] for $^{81}$Br; HRMS: calcd. for $C_{19}H_{29}O_3N_3Br$, 426.1387. found 426.1389 (0.5 ppm).

(f) 1-adamantylmethyl 4-[2-[(2-bromoacetyl)amino]acetyl]perazine-1-carboxylate (6f)

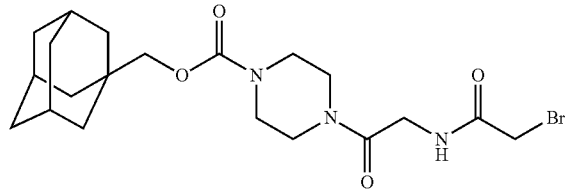 [SMILES: O=C(CBr)NCC(=O)N1CCN(C(=O)OCC23CC4CC(CC(C4)C2)C3)CC1]

The crude derivative obtained using the general protocol described previously was further triturated in diethyl ether to give the desired acetylated compound as a solid. $C_{20}H_{30}BrN_3O_4$; yield 76%; light beige solid; m.p. 210-211° C.; M=456.37 g/mol; IR (ATR): v=3335 (w), 2898 (m-s), 2847 (w), 1678 (s), 1621 (s), 1466 (m), 1430 (m), 1247 (m), 1220 (s), 1205 (m) cm$^{-1}$; $^1$H NMR (250 MHz, CDCl$_3$) δ 7.52 (s, 1H), 4.09 (d, J=4.0 Hz, 2H), 3.90 (s, 2H), 3.71 (s, 2H), 3.68-3.64 (m, 2H), 3.56-3.50 (m, 4H), 3.45-3.41 (m, 2H), 1.99 (as, 3H), 1.76-1.61 (m, 6H), 1.53 (d, J=2.9 Hz, 6H); $^{13}$C NMR (63 MHz, CDCl$_3$) δ 166.2 ($C_q$), 165.8 ($C_q$), 155.6 ($C_q$), 75.7 (CH$_2$), 44.4 (CH$_2$), 43.7 (CH$_2$), 43.5 (CH$_2$), 42.0 (CH$_2$), 42.0 (CH$_2$), 39.5 (3CH$_2$), 37.1 (3CH$_2$), 33.6 ($C_q$), 28.6 (CH$_2$), 28.1 (3CH); MS: m/z=480 [M+Na]$^+$; HRMS: calcd. for $C_{20}H_{31}O_4N_3Br$, 456.1492. found 456.1491 (0.3 ppm).

(g) 2-(1-adamantyl)ethyl 4-[2-[(2-bromoacetyl)amino]acetyl]perazine-1-carboxylate (6g)

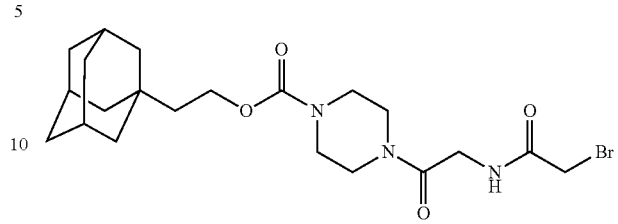

The crude derivative obtained using the general protocol described previously was further triturated in diethyl ether to give the desired acetylated compound as a solid. $C_{21}H_{32}BrN_3O_4$; yield 39%; light beige solid; m.p. 111-112° C.; M=470.40 g/mol; IR (ATR): v=3335 (w), 2895 (m-s), 2844 (m), 1700 (s), 1612 (s), 1427 (s), 1284 (w), 1226 (s) cm$^{-1}$; $^1$H NMR (250 MHz, CDCl$_3$) δ 7.51 (as, 1H), 4.16 (t, J=7.3 Hz, 2H), 4.09 (d, J=4.0 Hz, 2H), 3.90 (s, 2H), 3.66-3.59 (m, 2H), 3.57-3.45 (m, 4H), 3.41-3.34 (m, 2H), 1.95 (as, 3H), 1.73-1.59 (m, 6H), 1.52 (as, 6H), 1.43 (t, J=7.3 Hz, 2H); $^{13}$C NMR (63 MHz, CDCl$_3$) δ 166.1 ($C_q$), 165.8 ($C_q$), 155.5 ($C_q$), 62.6 (CH$_2$), 44.4 (CH$_2$), 43.6 (CH$_2$), 43.5 (CH$_2$), 42.9 (CH$_2$), 42.7 (3CH$_2$), 42.1 (CH$_2$), 42.0 (CH$_2$), 37.1 (3CH$_2$), 31.9 ($C_q$), 28.7 (3CH), 28.6 (CH$_2$); MS: m/z=494 [M+Na]$^+$; HRMS: calcd. for $C_{21}H_{33}O_4N_3Br$, 470.1649. found 470.1646 (0.6 ppm).

(h) 22-bromo-N-[2-[4-[[5-(dimethylamino)-1-naphthyl]sulfonyl]piperazin-1-yl]-2-oxo-ethyl]-acetamide (6h)

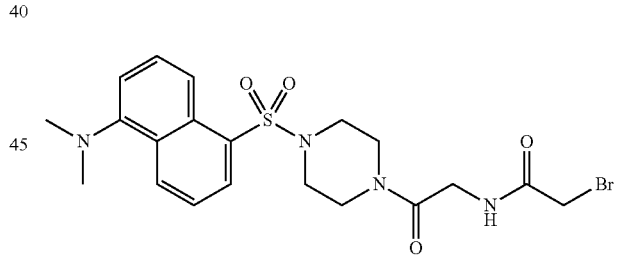

The crude compound obtained after the aqueous work-up (sodium bicarbonate satd. soln./DCM extraction) was triturated in diethyl ether to conduct to the desired derivative. $C_{20}H_{25}BrN_4O_4S$; yield 79%; yellow solid; m.p. 173-174° C.; M=497.41 g/mol; IR (ATR): v=3381 (w), 2925 (w), 1651 (s), 1451 (m), 1339 (m), 1144 (s), 941 (s), 792 (s), 707 (s) cm$^{-1}$; $^1$H NMR (250 MHz, CDCl$_3$) δ 8.64 (d, J=8.1 Hz, 1H), 8.38 (d, J=8.6 Hz, 1H), 8.21 (dd, J=7.4 Hz, J=1.2 Hz, 1H), 7.60-7.53 (m, 2H), 7.39 (as, 1H), 7.22 (d, J=7.4 Hz, 1H), 3.99 (d, J=4.1 Hz, 2H), 3.85 (s, 2H), 3.70-3.66 (m, 2H), 3.47-3.43 (m, 2H), 3.21 (dd, J=10.1 Hz, J=5.2 Hz, 4H), 2.92 (s, 6H); $^{13}$C NMR (63 MHz, CDCl$_3$) δ 165.9 ($C_q$), 165.9 ($C_q$), 132.1 ($C_q$), 131.2 (CH), 131.0 (CH), 130.3 ($C_q$), 129.9 ($C_q$), 128.4 (CH), 123.5 (CH), 119.7 (CH), 115.7 (CH), 45.6 (2CH$_3$), 45.5 (CH$_2$), 45.3 (CH$_2$), 44.2 (CH$_2$), 41.7 (2CH$_2$), 28.5 (CH$_2$);

(i) benzyl 4-[(2R)-2-[(2-bromoacetyl)amino]pro-panoyl]piperazine-1-carboxylate (6i)

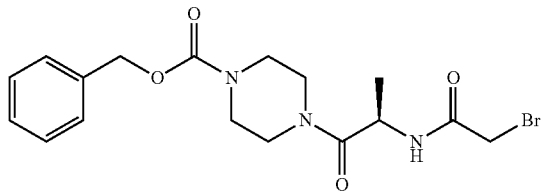 [SMILES: C[C@@H](NC(=O)CBr)C(=O)N1CCN(C(=O)OCc2ccccc2)CC1]

The crude derivative obtained using the general protocol described previously was further triturated in diethyl ether to give the desired acetylated compound as a solid. $C_{17}H_{22}BrN_3O_4$; light beige solid; m.p. 104-105° C.; yield 78%; M=412.28 g/mol; IR (ATR): v=3302 (m), 2929 (w), 1700 (s), 1678 (s), 1615 (s), 1475 (m), 1427 (s), 1257 (m), 1226 (s), 1120 (m), 741 (m) cm$^{-1}$; $^1$H NMR (250 MHz, CDCl$_3$) δ 7.53 (d, J=6.9 Hz, 1H), 7.40-7.30 (m, 5H), 5.15 (s, 2H), 4.83 (p, J=6.9 Hz, 1H), 3.85 (ad, J=1.3 Hz, 2H), 3.70-3.35 (m, 8H), 1.35 (d, J=6.8 Hz, 3H); $^{13}$C NMR (63 MHz, CDCl$_3$) δ 170.5 ($C_q$), 165.0 ($C_q$), 155.1 ($C_q$), 136.3 ($C_q$), 128.7 (2CH), 128.4 (CH), 128.2 (2CH), 67.7 (CH$_2$), 46.1 (CH), 45.3 (CH$_2$), 43.9 (CH$_2$), 43.6 (CH$_2$), 42.1 (CH$_2$), 28.8 (CH$_2$), 18.9 (CH$_3$); MS: m/z=434 [M+Na] for $^{79}$Br and 436 [M+Na]$^+$ for $^{81}$Br; HRMS: calcd. for $C_{17}H_{23}O_4N_3Br$, 412.0866. found 412.0870 (0.9 ppm).

(j) benzyl 4-[(2S)-2-[(2-bromoacetyl)amino]pro-panoyl]piperazine-1-carboxylate (6j)

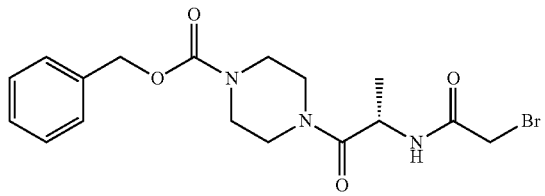 [SMILES: C[C@H](NC(=O)CBr)C(=O)N1CCN(C(=O)OCc2ccccc2)CC1]

The crude derivative obtained using the general protocol described previously was further triturated in diethyl ether to give the desired acetylated compound as a solid. $C_{17}H_{22}BrN_3O_4$; light beige solid; m.p. 104-105° C.; yield 83%; M=412.28 g/mol; IR (ATR): v=3305 (m), 2929 (w), 1697 (s), 1675 (s), 1612 (s), 1484 (m), 1427 (s), 1254 (m), 1226 (s), 1120 (m), 741 (m) cm$^{-1}$; $^1$H NMR (250 MHz, CDCl$_3$) δ 7.55 (d, J=4.7 Hz, 1H), 7.47-7.28 (m, 5H), 5.14 (s, 2H), 4.92-4.74 (m, 1H), 3.85 (s, 2H), 3.79-3.33 (m, 8H), 1.34 (m, J=6.1 Hz, 3H); $^{13}$C NMR (63 MHz, CDCl$_3$) δ 170.5 ($C_q$), 165.0 ($C_q$), 155.1 ($C_q$), 136.3 ($C_q$), 128.7 (2CH), 128.4 (CH), 128.2 (2CH), 67.7 (CH$_2$), 46.0 (CH), 45.3 (CH$_2$), 43.9 (CH$_2$), 43.6 (CH$_2$), 42.1 (CH$_2$), 28.8 (CH$_2$), 18.9 (CH$_3$); MS: m/z=434 [M+Na]$^+$ for $^{79}$Br and 436 [M+Na]$^+$ for $^{81}$Br; HRMS: calcd. for $C_{17}H_{23}O_4N_3Br$, 412.0866. found 412.0871 (1.1 ppm).

(k) benzyl 4-[(2R)-2-[(2-bromoacetyl)amino]-3-phenyl-propanoyl]perazine-1-carboxylate (6k)

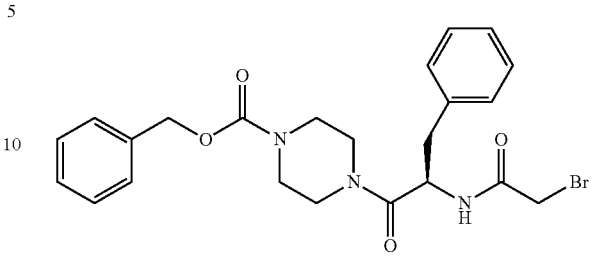

The crude derivative obtained using the protocol described previously was subsequently used without any further purification. $C_{23}H_{26}BrN_3O_4$; colorless viscous oil; yield 85%; M=488.37 g/mol; IR (ATR): v=3293 (w), 3026 (w), 1694 (s), 1621 (s), 1420 (s), 1226 (s), 1120 (w), 750 (w), 732 (w), 695 (m-s) cm$^{-1}$; $^1$H NMR (250 MHz, CDCl$_3$) δ 7.46 (d, J=8.0 Hz, 1H), 7.41-7.17 (m, 10H), 5.14-5.05 (m, 3H), 3.85 (s, 2H), 3.66-3.39 (m, 3H), 3.34-3.15 (m, 3H), 3.11-2.88 (m, 3H), 2.70-2.60 (m, 1H); $^{13}$C NMR (63 MHz, CDCl$_3$) δ 169.8 ($C_q$), 165.5 ($C_q$), 155.0 ($C_q$), 136.3 ($C_q$), 135.6 ($C_q$), 129.7 (2CH), 128.9 (2CH), 128.7 (2CH), 128.4 (CH), 128.2 (2CH), 127.7 (CH), 67.7 (CH$_2$), 50.6 (CH), 45.5 (CH$_2$), 43.3 (2CH$_2$), 42.0 (CH$_2$), 39.9 (CH$_2$), 28.7 (CH$_2$); MS: m/z=510 [M+Na] for $^{79}$Br and 512 [M+Na] for $^{81}$Br; HRMS: calcd. for $C_{23}H_{27}O_4N_3Br$, 488.1179. found 488.1178 (0.3 ppm).

(l) benzyl 4-[(2S)-2-[(2-bromoacetyl)amino]-3-phenyl-propanoyl]piperazine-1-carboxylate (6l)

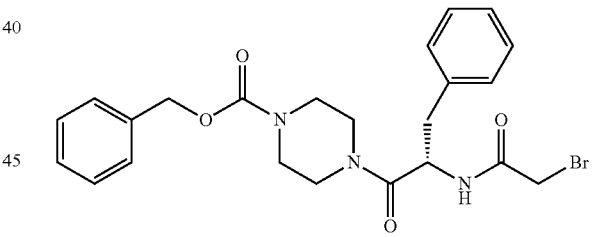

The crude derivative obtained using the general protocol described previously was subsequently used without any further purification. $C_{23}H_{26}BrN_3O_4$; colorless viscous oil; yield 98%; M=488.37 g/mol; IR (ATR): v=3274 (w), 3032 (w), 1697 (s), 1624 (s), 1427 (s), 1223 (s), 1117 (m), 750 (m), 695 (s) cm$^{-1}$; $^1$H NMR (250 MHz, CDCl$_3$) δ 7.41-7.17 (m, 11H), 5.14-5.05 (m, 3H), 3.85 (s, 2H), 3.62-3.40 (m, 3H), 3.34-3.18 (m, 3H), 3.11-2.88 (m, 3H), 2.72-2.62 (m, 1H); $^{13}$C NMR (63 MHz, CDCl$_3$) δ 169.6 ($C_q$), 165.3 ($C_q$), 155.0 ($C_q$), 136.3 ($C_q$), 135.6 ($C_q$), 129.7 (2CH), 128.9 (2CH), 128.7 (2CH), 128.4 (CH), 128.2 (2CH), 127.6 (CH), 67.6 (CH$_2$), 50.6 (CH), 45.5 (CH$_2$), 43.3 (2CH$_2$), 42.0 (CH$_2$), 39.9 (CH$_2$), 28.7 (CH$_2$); MS: m/z=510 [M+Na]$^+$ for $^{79}$Br and 512 [M+Na]$^+$ for $^{81}$Br; HRMS: calcd. for $C_{23}H_{27}O_4N_3Br$, 488.1179. found 488.1178 (0.3 ppm).

(m) tert-butyl 4-[2-[(2-bromoacetyl)amino]acetyl]piperazine-1-carboxylate (6m)

(o) N-[2-[4-(adamantane-1-carbonyl)piperazin-1-yl]-2-oxo-ethyl]-2-chloro-acetamide (6o)

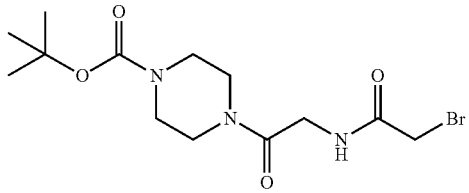 [SMILES: CC(C)(C)OC(=O)N1CCN(C(=O)CNC(=O)CBr)CC1]

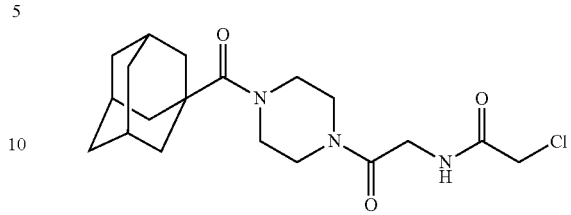

The crude derivative obtained using the general protocol described previously was further triturated in diethyl ether to give the desired acetylated compound as a solid. $C_{13}H_{22}BrN_3O_4$; yield 42%; white solid; m.p. 148-149° C.; M=364.24 g/mol; IR (ATR): v=3323 (w), 2968 (w), 1687 (m), 1615 (s), 1405 (m), 1247 (m), 1223 (m), 1156 (s), 1123 (m), 1023 (m), 859 (w) cm$^{-1}$; $^1$H NMR (250 MHz, CDCl$_3$) δ 7.52 (as, 1H), 4.09 (d, J=4.0 Hz, 2H), 3.90 (s, 2H), 3.65-3.61 (m, 2H), 3.49-3.42 (m, 4H), 3.40-3.36 (m, 2H), 1.47 (s, 9H); $^{13}$C NMR (63 MHz, CDCl$_3$) δ 166.1 ($C_q$), 165.8 ($C_q$), 154.5 ($C_q$), 80.7 ($C_q$), 44.4 (2CH$_2$), 42.1 (2CH$_2$), 41.9 (CH$_2$), 28.6 (CH$_2$), 28.5 (3CH$_3$); MS: m/z=386 [M+Na]$^+$ for $^{79}$Br and MS: m/z=388 [M+Na]$^+$ for $^{81}$Br; HRMS: calcd. for $C_{13}H_{23}O_4N_3Br$, 364.0866. found 364.0872 (1.5 ppm).

The crude material obtained following the general procedure was purified by flash chromatography using ethyl acetate as eluent. $C_{19}H_{28}ClN_3O_3$; yield 36%; white solid; m.p. 201-202° C.; M=381.90 g/mol; IR (ATR): v=3305 (m), 2904 (m), 1687 (s), 1648 (s), 1599 (s), 1560 (m), 1451 (m), 1414 (m-s), 1223 (s), 1011 (s) cm$^{-1}$; $^1$H NMR (250 MHz, CDCl$_3$) δ 7.60 (as, 1H), 4.11 (d, J=4.2 Hz, 2H), 4.08 (s, 2H), 3.74-3.70 (m, 4H), 3.67-3.63 (m, 2H), 3.43-3.39 (m, 2H), 2.06 (as, 3H), 1.99 (d, J=2.6 Hz, 6H), 1.79-1.68 (m, 6H); $^{13}$C NMR (63 MHz, CDCl$_3$) δ 176.3 ($C_q$), 166.3 ($C_q$), 166.2 ($C_q$), 45.4 (CH$_2$), 44.8 (CH$_2$), 44.7 (CH$_2$), 42.5 (CH$_2$), 42.4 (CH$_2$), 41.9 ($C_q$), 41.6 (CH$_2$), 39.2 (3CH$_2$), 36.7 (3CH$_2$), 28.5 (3CH); MS: m/z=404 [M+Na]$^+$; HRMS: calcd. for $C_{19}H_{29}O_3N_3Cl$ 382.1892, found 382.1896 (1.1 ppm).

(n) (6-methoxycarbonyl-2-naphthyl)methyl 4-[2-[(2-chloroacetyl)amino]acetyl]piperazine-1-carboxylate (6n)

(p) 2-chloro-N-[2-[4-[[5-(dimethylamino)-1-naphthyl]sulfonyl]piperazin-1-yl]-2-oxo-ethyl]-acetamide (6p)

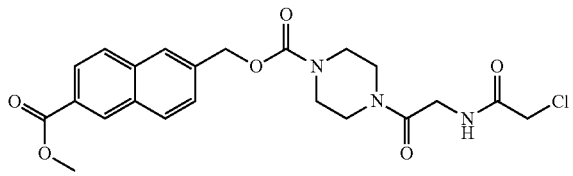 [SMILES: COC(=O)c1ccc2cc(COC(=O)N3CCN(C(=O)CNC(=O)CCl)CC3)ccc2c1]

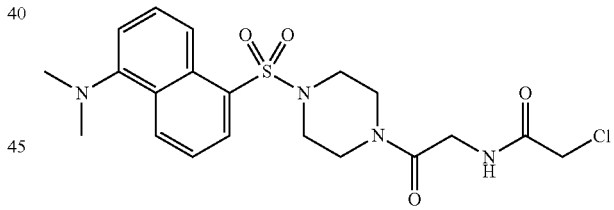

The crude derivative obtained using the general protocol described previously was further purified by flash chromatography (eluent: EtOAc). $C_{22}H_{24}ClN_3O_6$; yield 96%; white solid; m.p. 56-57° C.; M=461.90 g/mol; IR (ATR): v=2950 (w), 1697 (s), 1642 (s), 1430 (m-s), 1284 (m), 1223 (m-s), 753 (w) cm$^{-1}$; $^1$H NMR (250 MHz, CDCl$_3$) δ 8.61 (s, 1H), 8.09 (dd, J=8.6 Hz, J=1.7 Hz, 1H), 7.96 (d, J=8.5 Hz, 1H), 7.88 (d, J=8.7 Hz, 1H), 7.85 (s, 1H), 7.60 (as, 1H), 7.53 (dd, J=8.5 Hz, J=1.6 Hz, 1H), 5.33 (s, 2H), 4.10 (d, J=4.2 Hz, 2H), 4.08 (s, 2H), 3.99 (s, 3H), 3.69-3.65 (m, 2H), 3.60-3.54 (m, 4H), 3.44-3.41 (m, 2H); $^{13}$C NMR (63 MHz, CDCl$_3$) δ 167.2 ($C_q$), 166.3 ($C_q$), 166.1 ($C_q$), 155.1 ($C_q$), 136.4 ($C_q$), 135.4 ($C_q$), 132.3 ($C_q$), 130.9 (CH), 130.0 (CH), 128.4 (CH), 128.0 ($C_q$), 127.0 (CH), 126.6 (CH), 125.9 (CH), 67.6 (CH$_2$), 52.4 (CH$_3$), 44.3 (CH$_2$), 43.7 (CH$_2$), 43.6 (CH$_2$), 42.5 (CH$_2$), 42.0 (CH$_2$), 41.6 (CH$_2$); MS: m/z=484 [M+Na]$^+$; HRMS: calcd. for $C_{22}H_{24}O_6N_3ClNa$ 484.1246. found 484.1246 (0.0 ppm).

The crude material obtained following the general protocol mentioned above was further purified by flash-chromatography (eluent: AcOEt) to conduct to the titled compound. $C_{20}H_{25}ClN_4O_4S$; yield 80%; yellow-green solid; m.p. 68-69° C.; M=452.95 g/mol; IR (ATR): v=3314 (w), 2938 (w), 1648 (s), 1454 (m), 1436 (m), 1141 (s), 938 (m-s), 786 (s) cm$^{-1}$; $^1$H NMR (250 MHz, CDCl$_3$) δ 8.59 (d, J=8.5 Hz, 1H), 8.35 (d, J=8.7 Hz, J=1H), 8.20 (dd, J=7.4 Hz, J=1.3 Hz, 1H), 7.56 (d, J=7.4 Hz, 1H), 7.53 (d, J=7.5 Hz, 1H), 7.49 (as, 1H), 7.19 (d, J=7.5 Hz, 1H), 4.02 (s, 2H), 4.00 (d, J=4.2 Hz, 2H), 3.70-3.66 (m, 2H), 3.47-3.43 (m, 2H), 3.24-3.18 (m, 4H), 2.89 (s, 6H); $^{13}$C NMR (63 MHz, CDCl$_3$) δ 166.2 ($C_q$), 165.9 ($C_q$), 152.1 ($C_q$), 132.1 ($C_q$), 131.4 (CH), 131.0 (CH), 130.4 ($C_q$), 130.2 ($C_q$), 128.5 (CH), 123.3 (CH), 119.3 (CH), 115.6 (CH), 45.5 (2CH$_3$), 45.5 (CH$_2$), 45.4 (CH$_2$), 44.3 (CH$_2$), 42.4 (CH$_2$), 41.8 (CH$_2$), 41.4 (CH$_2$); MS: m/z=475 [M+Na]$^+$; HRMS: calcd. for $C_{20}H_{26}O_4N_4SCl$ 453.1358. found 453.1358 (0.0 ppm).

(q) tert-butyl 4-(2-bromoacetyl)piperazine-1-carboxylate (6q)

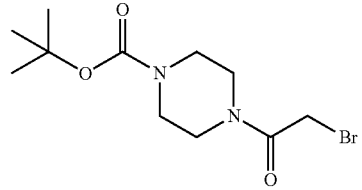 [SMILES: CC(C)(C)OC(=O)N1CCN(C(=O)CBr)CC1]

Under inert atmosphere and at −78° C., bromoacetyl bromide (53.7 mmol, 1 eq.) was slowly added to a solution of Boc-piperazine (53.7 mmol, 1 eq.) and TEA (59.1 mmol, 1.1 eq.) in DCM (150 ml). The reaction mixture was stirred at −78° C. for 3 h, diluted with DCM (75 ml) and washed with water. The recovered organic layer was dried over magnesium sulfate and the solvent was evaporated under vacuum. The obtained crude product was further triturated with diethyl ether, filtered and dried under vacuum to conduct to the desired acetylated compound. $C_{11}H_{19}BrN_2O_3$; yield 78%; white solid; m.p. 243-244° C.; M=307.18 g/mol; IR (KBr): ν=2965 (m), 1689 (s), 1632 (s), 1417 (s), 1246 (s), 1167 (s), 1023 (m); cm$^{-1}$; $^1$H NMR (250 MHz, CDCl$_3$) δ 3.87 (s, 2H), 3.61-3.57 (m, 2H), 3.55-3.47 (m, 4H), 3.46-3.41 (m, 2H), 1.46 (s, 9H); $^{13}$C NMR (63 MHz, CDCl$_3$) δ 165.5 ($C_q$), 154.5 ($C_q$), 80.5 ($C_q$), 46.6 (2CH$_2$), 40.9 (2CH$_2$), 28.4 (3CH$_3$), 25.7 (CH$_2$);

(r) benzyl 4-(2-acetamidoacetyl)piperazine-1-carboxylate (6r)

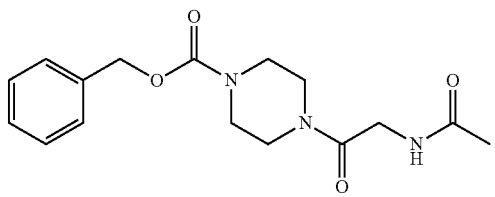 [SMILES: CC(=O)NCC(=O)N1CCN(C(=O)OCc2ccccc2)CC1]

Under inert atmosphere and at −78° C., acetyl bromide (1.1 eq.) was slowly added to a solution of the corresponding amine (0.36 mmol, 1 eq.) and TEA (1.5 eq.) in DCM (5 ml). The reaction mixture was stirred at −78° C. for 2 h, diluted with DCM (50 ml) and subsequently washed with hydrogen chloride (aq. soln. 0.1 M, 3×50 ml). The recovered organic layer was dried over magnesium sulfate and the solvent was evaporated under vacuum to give the crude product further triturated in diethyl ether to conduct to the desired acetylated derivative. $C_{16}H_{21}N_3O_4$; yield 90%; white solid; m.p. 134-135° C.; M=319.36 g/mol; IR (ATR): ν=3356 (m), 2919 (s), 1681 (m), 1657 (s), 1636 (s), 1563 (m), 1420 (m), 1229 (s), 1120 (m), 1068 (m), 1023 (m) cm$^{-1}$; $^1$H NMR (250 MHz, CDCl$_3$) δ 7.39-7.33 (m, 5H), 6.56 (as, 1H), 5.15 (s, 2H), 4.06 (d, J=3.8 Hz, 2H), 3.64-3.59 (m, 2H), 3.56-3.50 (m, 4H), 3.45-3.40 (m, 2H), 2.05 (s, 3H); $^{13}$C NMR (63 MHz, CDCl$_3$) δ 170.3 ($C_q$), 166.9 ($C_q$), 155.2 ($C_q$), 136.4 ($C_q$), 128.8 (2CH), 128.5 (CH), 128.3 (2CH), 67.8 (CH$_2$), 44.3 (CH$_2$), 43.7 (CH$_2$), 43.6 (CH$_2$), 41.9 (CH$_2$), 41.5 (CH$_2$), 23.2 (CH$_3$); MS: m/z=342 [M+Na]; HRMS: calcd. for $C_{16}H_{22}O_4N_3$ 320.1605, found 320.1608 (1.0 ppm).

Preparation of the Dimethylsulfonium Salts (G)

Dimethyl sulfide (2.5 mmol, 10 eq.) was added to a solution of the previously obtained bromo-acetylated compounds (0.25 mmol, 1 eq.) in methanol (5 ml). The reaction vessel was sealed and the mixture vigorously stirred for 48 h at room temperature. The solvent was evaporated, the residue was dissolved in water (15 ml) and washed with ethyl acetate (3×20 ml). The recovered aqueous layer was freeze-dried to give the final dimethylsulfonium bromide salts as solids.

(a) [2-[[2-(4-benzyloxycarbonylpiperazin-1-yl)-2-oxo-ethyl]amino]-2-oxo-ethyl]-dimethyl-sulfonium bromide (7a)

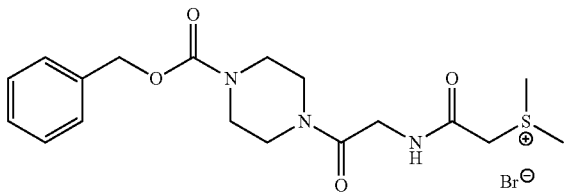 [SMILES: C[S+](C)CC(=O)NCC(=O)N1CCN(C(=O)OCc2ccccc2)CC1 ; [Br-]]

$C_{18}H_{26}BrN_3O_4S$; yield 83%; white solid/hygroscopic; M=460.39 g/mol; IR (ATR): ν=2919 (w), 1681 (s), 1642 (s), 1427 (m), 1223 (s), 1123 (w), 1020 (w), 762 (w), 695 (w) cm$^{-1}$; $^1$H NMR (250 MHz, DMSO$_3$) δ 7.38-7.32 (m, 5H), 5.10 (s, 2H), 4.47 (s, 2H), 4.08 (d, J=5.4 Hz, 2H), 3.53-3.40 (m, 8H), 2.94 (s, 6H); $^{13}$C NMR (63 MHz, DMSO$_3$) δ 166.2 ($C_q$), 163.2 ($C_q$), 154.4 ($C_q$), 136.7 ($C_q$), 128.4 (2CH), 127.9 (CH), 127.6 (2CH), 66.4 (CH$_2$), 46.4 (CH$_2$), 43.7 (CH$_2$), 43.4 (CH$_2$), 43.1 (CH$_2$), 41.1 (CH$_2$), 41.0 (CH$_2$), 24.5 (2CH$_3$); MS: m/z=380 [M−Br]$^+$; HRMS: calcd. for $C_{18}H_{26}O_4N_3S$, 380.1639. found 380.1638 (0.1 ppm).

(b) [2-[[2-[4-[(4-methoxycarbonylphenyl)methoxycarbonyl]piperazin-1-yl]-2-oxo-ethyl]-amino]-2-oxo-ethyl]-dimethyl-sulfonium bromide (7b)

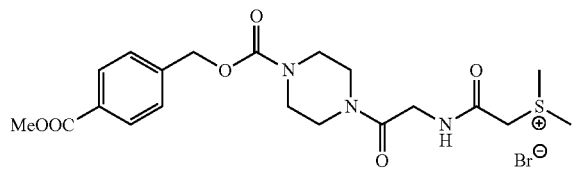 [SMILES: COC(=O)c1ccc(COC(=O)N2CCN(C(=O)CNC(=O)C[S+](C)C)CC2)cc1 ; [Br-]]

$C_{20}H_{28}BrN_3O_6S$; yield 94%; light beige solid/hygroscopic; M=518.42 g/mol; IR (ATR): ν=3211 (w), 2913 (w), 1694 (s), 1645 (s), 1423 (m-s), 1407 (m), 1278 (m-s), 1220 (m-s), 1102 (m), 1017 (m), 753 (m) cm$^{-1}$; $^1$H NMR (250 MHz, DMSO) δ 8.90 (t, J=5.4 Hz, 1H), 7.96 (d, J=8.4 Hz, 2H), 7.51 (d, J=8.4 Hz, 2H), 5.19 (s, 2H), 4.48 (s, 2H), 4.09 (d, J=5.4 Hz, 2H), 3.85 (s, 3H), 3.86-3.38 (m, 8H), 2.94 (s, 6H); $^{13}$C NMR (63 MHz, DMSO) δ 166.3 ($C_q$), 166.0 ($C_q$), 163.2 ($C_q$), 154.2 ($C_q$), 142.3 ($C_q$), 129.3 (2CH), 129.0 ($C_q$), 127.4 (2CH), 65.7 (CH$_2$), 52.2. (CH$_3$), 46.4 (CH$_2$), 43.7 (CH$_2$), 43.4 (CH$_2$), 43.2 (CH$_2$), 41.1 (CH$_2$), 41.0 (CH$_2$), 24.5 (2CH$_3$); MS: m/z=438 [M+]$^+$; HRMS: calcd. for $C_{20}H_{28}O_6N_3S$, 438.1693. found 438.1693 (0.1 ppm).

(c) dimethyl-[2-[[2-[4-(2-naphthylmethoxycarbonyl)piperazin-1-yl]-2-oxo-ethyl]amino]-2-oxo-ethyl]sulfonium bromide (7c)

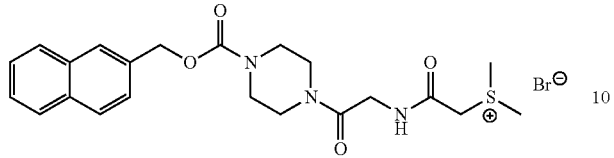

$C_{22}H_{28}BrN_3O_4S$; yield 47%; light beige solid/hydroscopic; M=510.44 g/mol; IR (ATR): ν=2910 (w), 1678 (s), 1639 (s), 1463 (m), 1427 (s), 1223 (s), 817 (w), 747 (m) cm$^{-1}$; $^1$H NMR (250 MHz, CDCl$_3$) δ 8.88 (t, J=4.9 Hz, 1H), 7.86-7.80 (m, 4H), 7.51-7.43 (m, 3H), 5.29 (s, 2H), 5.05 (s, 2H), 4.12 (d, J=5.3 Hz, 2H), 3.61-3.41 (m, 8H), 3.32 (s, 6H); $^{13}$C NMR (63 MHz, CDCl$_3$) δ 166.3 (C$_q$), 163.3 (C$_q$), 154.5 (C$_q$), 134.3 (C$_q$), 132.7 (C$_q$), 132.6 (C$_q$), 128.1 (CH), 127.8 (CH), 127.6 (CH), 126.5 (CH), 126.4 (CH), 126.3 (CH), 125.8 (CH), 66.6 (CH$_2$), 46.5 (CH$_2$), 43.8 (CH$_2$), 43.4 (CH$_2$), 43.2 (CH$_2$), 41.2 (CH$_2$), 41.1 (CH$_2$), 24.6 (2CH$_3$); MS: m/z=430 [M-Br]$^+$; HRMS: calcd. for $C_{22}H_{28}O_4N_3S$, 430.1795. found 430.1793 (0.5 ppm).

(d) [2-[[2-[4-[(6-methoxycarbonyl-2-naphthyl)methoxycarbonyl]piperazin-1-yl]-2-oxo-ethyl]amino]-2-oxo-ethyl]-dimethyl-sulfonium bromide (7d)

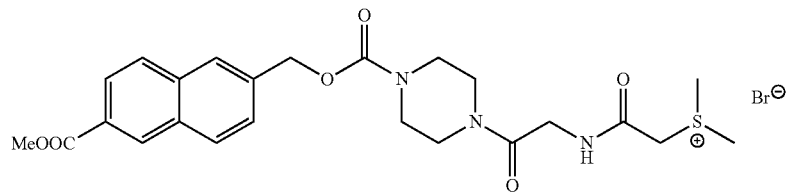 [SMILES: COC(=O)c1ccc2cc(COC(=O)N3CCN(C(=O)CNC(=O)C[S+](C)C)CC3)ccc2c1 ; [Br-]]

$C_{24}H_{30}BrN_3O_6S$; yield 81%; white solid; m.p. 125-126° C.; M=568.48 g/mol; IR (ATR): ν=3320 (w), 2980 (w), 1712 (m), 1675 (m), 1639 (s), 1433 (m), 1287 (m), 1232 (s), 1199 (m), 1126 (m), 759 (w) cm$^{-1}$; $^1$H NMR (250 MHz, DMSO) δ 8.88 (t, J=5.4 Hz, 1H), 8.65 (s, 1H), 8.16 (d, J=8.6 Hz, 1H), 8.08-7.99 (m, 3H), 7.62 (dd, J=8.5 Hz, J=1.6 Hz, 1H), 5.30 (s, 2H), 4.43 (s, 2H), 4.10 (d, J=5.4 Hz, 2H), 3.92 (s, 3H), 3.56-3.40 (m, 8H), 2.91 (s, 6H); $^{13}$C NMR (63 MHz, DMSO) δ 166.3 (C$_q$), 166.3 (C$_q$), 163.2 (C$_q$), 154.3 (C$_q$), 137.3 (C$_q$), 134.9 (C$_q$), 131.6 (C$_q$), 130.4 (CH), 129.7 (CH), 128.5 (CH), 127.1 (C$_q$), 126.5 (CH), 125.9 (CH), 125.2 (CH), 66.3 (CH$_2$), 52.3 (CH$_3$), 46.5 (CH$_2$), 43.7 (CH$_2$), 43.4 (CH$_2$), 43.3 (CH$_2$), 41.1 (CH$_2$), 41.1 (CH$_2$), 24.6 (2CH$_3$); MS: m/z=488 [M]$^+$; HRMS: calcd. for $C_{24}H_{30}O_6N_3S$, 488.1850. found 488.1841 (1.8 ppm).

(e) [2-[[2-[4-(adamantane-1-carbonyl)piperazin-1-yl]-2-oxo-ethyl]amino]-2-oxo-ethyl]-dimethyl-sulfonium bromide (7e)

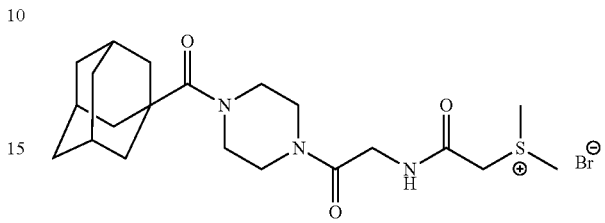

$C_{21}H_{34}BrN_3O_3S$; yield 98%; white solid; m.p. 157-158° C.; M=488.48 g/mol; IR (ATR): ν=3417 (w), 2901 (m-s), 2844 (w), 1645 (s), 1612 (s), 1445 (w), 1408 (m), 1241 (m), 1214 (m), 1008 (s) cm$^{-1}$; $^1$H NMR (250 MHz, DMSO) δ 8.87 (t, J=5.3 Hz, 1H), 4.42 (s, 2H), 4.08 (d, J=5.3 Hz, 2H), 3.65-3.54 (m, 4H), 3.48-3.38 (m, 4H), 2.90 (s, 6H), 1.98 (as, 3H), 1.92-1.86 (m, 6H), 1.74-1.62 (m, 6H); $^{13}$C NMR (63 MHz, DMSO) δ 174.6 (C$_q$), 166.2 (C$_q$), 163.2 (C$_q$), 46.5 (CH$_2$), 44.5 (2CH$_2$), 44.2 (CH$_2$), 41.7 (CH$_2$), 41.0 (CH$_2$), 40.9 (C$_q$), 38.4 (3CH$_2$), 36.0 (3CH$_2$), 27.9 (3CH), 24.6 (2CH$_3$); MS: m/z=408 [M-Br]$^+$; HRMS: calcd. for $C_{21}H_{34}O_3N_3S$, 408.2315. found 408.2317 (0.4 ppm).

(f) [2-[[2-[4-(1-adamantylmethoxycarbonyl)piperazin-1-yl]-2-oxo-ethyl]amino]-2-oxo-ethyl]-dimethyl-sulfonium bromide (7f)

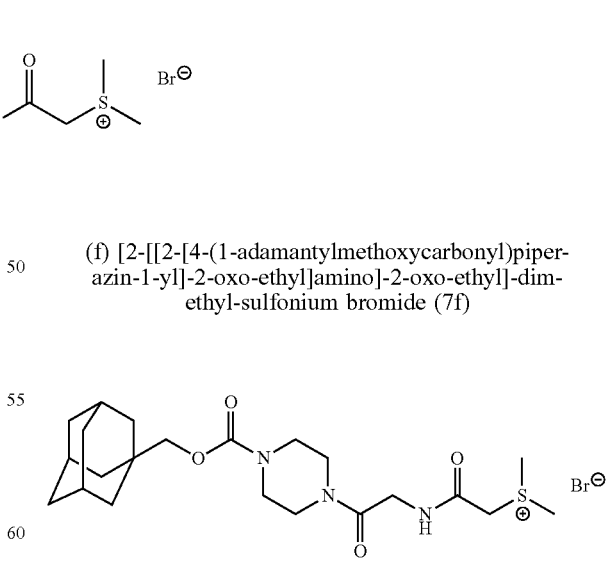

$C_{22}H_{36}BrN_3O_4S$; yield 67%; light beige solid/hygroscopic; M=518.51 g/mol; IR (ATR): ν=3414 (w), 2895 (s), 2844 (m), 1669 (s), 1642 (s), 1466 (m-s), 1423 (s), 1220 (s) cm$^{-1}$; $^1$H NMR (250 MHz, DMSO) δ 8.89 (t, J=5.3 Hz, 1H), 4.46 (s, 2H), 4.08 (d, J=5.4 Hz, 2H), 3.62 (s, 2H), 3.54-3.40

(m, 8H), 2.93 (s, 6H), 1.94 (as, 3H), 1.71-1.58 (m, 6H), 1.50 (as, 6H); $^{13}$C NMR (63 MHz, DMSO) δ 166.3 ($C_q$), 163.2 ($C_q$), 154.8 ($C_q$), 74.3 ($CH_2$), 46.4 ($CH_2$), 43.7 ($CH_2$), 43.3 ($CH_2$), 43.0 ($CH_2$), 41.1 ($CH_2$), 41.0 ($CH_2$), 38.7 ($3CH_2$), 36.4 ($3CH_2$), 33.1 ($C_q$), 27.4 (3CH), 24.6 ($2CH_3$); MS: m/z=438 [M–Br]$^+$; HRMS: calcd. for $C_{22}H_{36}O_4N_3S$, 438.2421. found 438.2419 (0.5 ppm).

(g) [2-[[2-[4-[2-(1-adamantyl)ethoxycarbonyl]piperazin-1-yl]-2-oxo-ethyl]amino]-2-oxo-ethyl]-dimethyl-sulfonium bromide (7g)

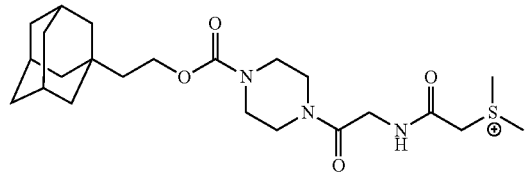

$C_{23}H_{38}BrN_3O_4S$; yield 75%; light beige solid/hygroscopic; M=532.53 g/mol; IR (ATR): ν=2895 (m-s), 2847 (w), 1684 (s), 1423 (s), 1226 (s), 1020 (w) cm$^{-1}$; $^1$H NMR (250 MHz, DMSO) δ 8.89 (t, J=5.3 Hz, 1H), 4.47 (s, 2H), 4.09-4.03 (m, 4H), 3.50-3.38 (m, 8H), 2.93 (s, 6H), 1.91 (as, 3H), 1.69-1.57 (m, 6H), 1.49 (as, 6H), 1.37 (t, J=7.3, 2H); $^{13}$C NMR (63 MHz, DMSO) δ 166.2 ($C_q$), 163.2 ($C_q$), 154.6 ($C_q$), 61.2 ($CH_2$), 46.4 ($CH_2$), 43.7 ($CH_2$), 43.3 ($CH_2$), 43.0 ($CH_2$), 42.4 ($CH_2$), 41.9 ($3CH_2$), 41.1 ($CH_2$), 41.0 ($CH_2$), 36.5 ($3CH_2$), 31.3 ($C_q$), 27.9 (3CH), 24.6 ($2CH_3$); MS: m/z=452 [M–Br]$^+$; HRMS: calcd. for $C_{23}H_{38}O_4N_3S$, 452.2578. found 452.2575 (0.6 ppm).

(h) [2-[[2-[4-[[5-(dimethylamino)-1-naphthyl]sulfonyl]piperazin-1-yl]-2-oxo-ethyl]amino]-2-oxo-ethyl]-dimethyl-sulfonium bromide (7h)

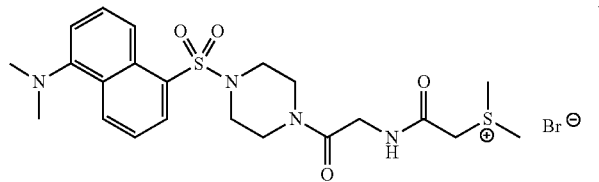

$C_{22}H_{31}BrN_4O_4S_2$; yield 76%; light yellow solid; m.p. 98-99° C.; M=559.54 g/mol; IR (ATR): ν=3475 (m), 2992 (w), 1672 (s), 1648 (s), 1345 (s), 1153 (s), 1144 (s), 935 (s), 795 (s), 713 (s) cm$^{-1}$; $^1$H NMR (250 MHz, DMSO) δ 8.79 (t, J=5.4 Hz, 1H), 8.54 (d, J=8.5 Hz, 1H), 8.30 (d, J=8.7 Hz, 1H), 8.14 (dd, J=7.4 Hz, J=1.1 Hz, 1H), 7.68 (dd, J=8.5 Hz, J=7.4 Hz, 1H), 7.63 (dd, J=8.5 Hz, J=7.7 Hz, 1H), 7.28 (d, J=7.3 Hz, 1H), 4.38 (s, 2H), 4.01 (d, J=5.3 Hz, 2H), 3.55-3.43 (m, 4H), 3.18-3.05 (m, 4H), 2.87 (s, 6H), 2.83 (s, 6H); $^{13}$C NMR (63 MHz, DMSO) δ 166.2 ($C_q$), 163.2 ($C_q$), 151.5 ($C_q$), 132.4 ($C_q$), 130.5 (CH), 130.2 (CH), 129.6 ($C_q$), 129.2 ($C_q$), 128.3 (CH), 123.8 (CH), 118.9 (CH), 115.4 (CH), 46.5 ($CH_2$), 45.3 ($CH_2$), 45.2 ($CH_2$), 45.1 ($2CH_3$), 43.7 ($CH_2$), 41.0 ($CH_2$), 40.9 ($CH_2$), 24.5 ($2CH_3$); MS: m/z=479 [M]$^+$; HRMS: calcd. for $C_{22}H_{31}O_4N_4S_2$ 479.1781, found 479.1779 (0.5 ppm).

(i) [2-[[(1S)-2-(4-benzyloxycarbonylpiperazin-1-yl)-1-methyl-2-oxo-ethyl]amino]-2-oxo-ethyl]-dimethyl-sulfonium bromide (7j)

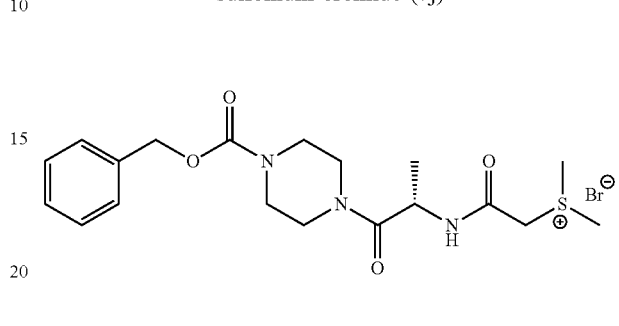

$C_{19}H_{28}BrN_3O_4S$; light beige solid/hygroscopic; yield 78%; M=474.41 g/mol; IR (ATR): ν=2986 (w), 1694 (s), 1636 (s), 1420 (s), 1220 (s), 1020 (m), 759 (m), 698 (m) cm$^{-1}$; $^1$H NMR (250 MHz, DMSO) δ 9.07 (d, J=7.3 Hz, 1H), 7.39-7.32 (m, 5H), 5.10 (s, 2H), 4.78 (p, J=6.6 Hz, 1H), 4.40 (s, 2H), 3.51-3.46 (m, 8H), 2.90 (s, 3H), 2.89 (s, 3H), 1.21 (d, J=6.9 Hz, 3H); $^{13}$C NMR (63 MHz, DMSO) δ 169.8 ($C_q$), 162.4 ($C_q$), 154.4 ($C_q$), 136.7 ($C_q$), 128.4 (2CH), 127.9 (CH), 127.7 (2CH), 66.4 ($CH_2$), 46.6 ($CH_2$), 45.3 (CH), 44.5 ($CH_2$), 43.6 ($CH_2$), 43.2 ($CH_2$), 41.3 ($CH_2$), 24.7 ($CH_3$), 24.6 ($CH_3$), 17.6 ($CH_3$); MS: m/z=394 [M–Br]$^+$; HRMS: calcd. for $C_{19}H_{28}O_4N_3S$, 394.1795. found 394.1800 (1.3 ppm).

(j) [2-[[2-(4-tert-butoxycarbonylpiperazin-1-yl)-2-oxo-ethyl]amino]-2-oxo-ethyl]-dimethyl-sulfonium bromide (7m)

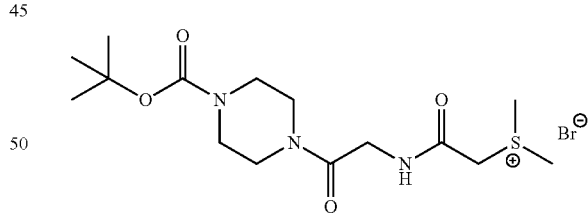

$C_{15}H_{28}BrN_3O_4S$; light yellow solid/hygroscopic; yield 48%; M=426.37 g/mol; IR (ATR): ν=3429 (w), 2974 (w), 1672 (s), 1645 (s), 1408 (s), 1460 (w), 1363 (m), 1232 (m), 1163 (m-s), 1107 (w) cm$^{-1}$; $^1$H NMR (250 MHz, DMSO) δ 8.87 (t, J=5.4 Hz, 1H), 4.43 (s, 2H), 4.08 (d, J=5.4 Hz, 2H), 3.45-3.32 (m, 8H), 2.91 (s, 6H), 1.41 (s, 9H); $^{13}$C NMR (63 MHz, DMSO) δ 166.2 ($C_q$), 163.2 ($C_q$), 153.8 ($C_q$), 79.2 ($C_q$), 46.5 ($2CH_2$), 43.8 ($CH_2$), 41.2 ($CH_2$), 41.0 ($2CH_2$), 28.0 ($3CH_3$), 24.6 ($2CH_3$); MS: m/z=346 [M]$^+$; HRMS: calcd. for $C_{15}H_{28}O_4N_3S$, 346.1795. found 346.1797 (0.6 ppm).

(k) benzyl 4-[2-[[2-(1,3,4,5-tetramethylimidazol-1-ium-2-yl)sulfanylacetyl]amino]-acetyl]-piperazine-1-carboxylate bromide (7s)

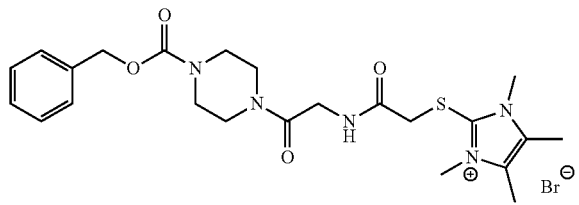 [SMILES: Cc1c(C)[n+](C)c(SCC(=O)NCC(=O)N2CCN(C(=O)OCc3ccccc3)CC2)n1C ; [Br-]]

$C_{23}H_{32}BrN_5O_4S$; light beige solid/hygroscopic; yield 79%; M=554.50 g/mol; IR (ATR): v=3402 (w), 3192 (w), 2922 (w), 1696 (s), 1645 (s), 1423 (s), 1226 (s), 1026 (w) cm$^{-1}$; $^1$H NMR (250 MHz, DMSO) δ 8.35 (t, J=5.3 Hz, 1H), 7.38-7.32 (m, 5H), 5.10 (s, 2H), 3.96 (d, J=5.4 Hz, 2H), 3.77 (s, 6H), 3.68 (s, 2H), 3.50-3.39 (m, 8H), 2.29 (s, 6H); $^{13}$C NMR (63 MHz, DMSO) δ 167.0 ($C_q$), 166.6 ($C_q$), 154.4 ($C_q$), 136.7 ($C_q$), 135.9 ($C_q$), 129.2 ($C_q$), 128.4 (2CH), 127.9 (CH), 127.6 (2CH), 66.4 (CH$_2$), 43.7 (CH$_2$), 43.3 (CH$_2$), 43.1 (CH$_2$), 41.0 (CH$_2$), 40.7 (CH$_2$), 36.8 (CH$_2$), 33.5 (2CH$_3$), 8.8 (2CH$_3$); MS: m/z=474 [M]$^+$; HRMS: calcd. for $C_{23}H_{32}O_4N_5S$, 474.2170. found 474.2161 (1.8 ppm).

General Method for the Preparation of Vinyl Sulfonamides (H)

Under inert atmosphere, triethylamine (1.1 eq.) was added at −60° C. to a solution of 2-chloroethyl-sulfonyl chloride (0.3 mmol, 1 eq.) in DCM (6 mL). The mixture was stirred at −60° C. for 2 h before adding the corresponding amine (1.1 eq.) and triethylamine (1.1 eq.), then the reaction was stirred for two additional hours at 0° C. The reaction was quenched by addition of HCl (aq. soln., 0.1 N, 20 mL) and extracted with DCM (3×20 mL). The recovered organic layers were dried over magnesium sulfate and the solvent evaporated under reduced pressure. The crude material was further purified by flash-chromatography (eluent: ethyle acetate) to conduct to the desired vinyl sulfonamide.

(a) benzyl 4-[2-(vinylsulfonylamino)acetyl]piperazine-1-carboxylate (8a)

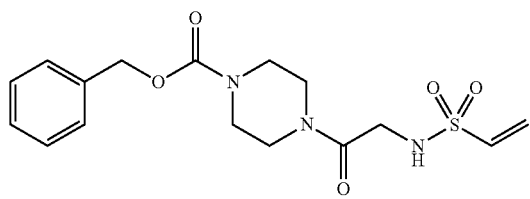 [SMILES: C=CS(=O)(=O)NCC(=O)N1CCN(C(=O)OCc2ccccc2)CC1]

$C_{16}H_{21}N_3O_5S$; yield 53%; colorless viscous oil becoming whitish solid on standing; m.p. 66-67° C.; M=367.42 g/mol; IR (ATR): v=3220 (w), 2865 (w), 1694 (s), 1648 (s), 1423 (m), 1326 (w), 1223 (s), 1141 (m), 1123 (m), 762 (m), 729 (m), 695 (m) cm$^{-1}$; $^1$H NMR (250 MHz, CDCl$_3$) δ 7.41-7.30 (m, 5H), 6.51 (dd, J=16.5 Hz, J=9.8 Hz, 1H), 6.25 (d, J=16.5 Hz, 1H), 5.95 (d, J=9.8 Hz, 1H), 5.44 (t, J=4.2 Hz, 1H), 5.15 (s, 2H), 3.84 (d, J=4.4 Hz, 2H), 3.68-3.62 (m, 2H), 3.57-3.50 (m, 4H), 3.41-3.28 (m, 2H); $^{13}$C NMR (63 MHz, CDCl$_3$) δ 165.9 ($C_q$), 155.1 ($C_q$), 136.3 ($C_q$), 135.5 (CH), 128.8 (2CH), 128.5 (CH), 128.3 (2CH), 127.2 (CH$_2$), 67.8 (CH$_2$), 44.3 (CH$_2$), 43.9 (CH$_2$), 43.7 (CH$_2$), 43.6 (CH$_2$), 42.2 (CH$_2$); MS: m/z=390 [M+Na]$^+$; HRMS: calcd. for $C_{16}H_{22}O_5N_3S$, 368.1275. found 368.1280 (1.4 ppm).

(b) N-[2-[4-(adamantane-1-carbonyl)piperazin-1-yl]-2-oxo-ethyl]ethenesulfonamide (8e)

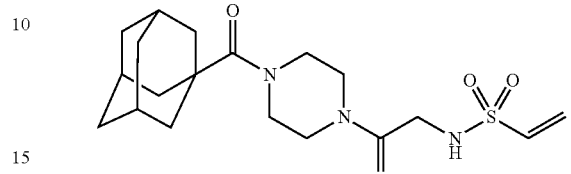

$C_{19}H_{29}N_3O_4S$; yield 49%; white solid; m.p. 159-160° C.; M=395.52 g/mol; IR (ATR): v=3232 (w), 2895 (m), 2850 (w), 1645 (m-s), 1612 (m-s), 1402 (m-s), 1320 (m), 1232 (m-s), 1153 (s), 1011 (m-s), 984 (m), 738 (m) cm$^{-1}$; $^1$H NMR (250 MHz, DMSO) δ 7.35 (t, J=5.5 Hz, 1H), 6.71 (dd, J=16.6 Hz, J=10.0 Hz, 1H), 6.03 (d, J=16.6 Hz, 1H), 5.94 (d, J=10.0 Hz, 1H), 3.82 (d, J=5.6 Hz, 2H), 3.57-3.46 (m, 4H), 3.42-3.38 (m, 4H), 1.97 (as, 3H), 1.89 (s, 6H), 1.73-1.62 (m, 6H); $^{13}$C NMR (63 MHz, DMSO) δ 174.6 ($C_q$), 166.4 ($C_q$), 137.0 (CH), 125.1 (CH$_2$), 44.5 (2CH$_2$), 44.3 (CH$_2$), 43.7 (CH$_2$), 41.7 (CH$_2$), 40.9 ($C_q$), 38.4 (3CH$_2$), 36.0 (3CH$_2$), 27.9 (3CH); HRMS: calcd. for $C_{19}H_{30}O_4N_3S$, 396.1952. found 396.1954 (0.6 ppm).

Example 2—Inhibition of Tissue Transglutaminase (TG2) Activity

Methodology

TG transamidation activity and the affect of inhibitors on activity was measured by biotin X-cadaverine incorporation into N,N'-dimethylcasein. After coating 96 well plates with 100 μl of 10 mg/ml N,N'-dimethylcasein in 50 mM Tris-Cl, pH8 at 4° C. over night, plates were washed with TBS-0.05% Tween-20(v/v), pH 7.6 and TBS, pH 7.6, and 100 μl purified recombinant human TG2 (400 ng/ml Zedira, Germany) (tissue transglutaminase) in 50 mM Tris-HCl, pH7.4, containing 1 mM DTT, 10 mM CaCl$_2$ and 0.1 μM biotin-cadaverine added into the coated wells containing the appropriate concentration of inhibitor. The reaction was allowed to proceed for 2 h at 37° C. The plate was then washed twice with TBS-Tween-20 (v/v), pH 7.6 and once with TBS, pH 7.6 before being blocked with 100 μl of blocking buffer (3% (w/v) BSA in TBS-Tween, pH 7.6) for 30 min at 37° C. After blocking, the wells were incubated with 100 μl HRP-conjugated Extr-Avidin peroxidase (Sigma-Aldrich, UK) in blocking buffer (1:1,000 dilution) for 1 h at 37° C. After another set of washes, TG2 activity was measured using Sigma Fast OPD, tablets dissolved in 20 ml of distilled H$_2$O. The colour was developed by adding 2.5 M H$_2$SO$_4$ and the absorbance at 490 nm measured using a microplate reader ELx808™. All inhibitors were dissolved in DMSO as a 100 mM solution prior to addition to the assay.

For determination of the activity of transglutaminase 1, transglutaminase 3 and Factor X111a, a commercial microassay was used, TG-CovTest (Covalab, Lyon, France; see also Perez et al. Anal Biochem. 2009; 389:150-156).

Results

The results of the tissue transglutaminase IC50 assay are shown in Tables 1, 2, 3 and 4.

TABLE 1

Compound: R'—C(O)—N(piperazine)N—CH₂—C(O)—NH—C(O)—R''

| R' | R'' | IC50 for TG2 (μM) | Ref code |
|---|---|---|---|
| benzyl-O-Lig | Lig-CH₂-Br | 0.75 ± 0.07 | EB 1-32 |
| | Lig-CH₂-S⁺(CH₃)₂ | 1.4 ± 0.5 | EB 1-33 |
| | Lig-CH₂-S-(1,3-dimethyl-4,5-dimethylimidazolium) | 100 | EB 1-34 |
| | Lig—CH₃ | 4.25 ± 0.78 | EB 1-44 |
| | Lig-CH=CH₂ | 5.925 ± 0.11 | EB 1-50 |
| | Lig-CH₂-S⁺(Et)₂ | 1.85 ± 0 | EB 2-13 |
| tBu-O-Lig | Lig-CH₂-Br | 0.008 ± 0.003 | EB 1-37 |
| | Lig-CH₂-S⁺(CH₃)₂ | 0.070 ± 0.007 | EB 1-46 |
| | Lig-CH₂-S-(1,3-dimethyl-4,5-dimethylimidazolium) | 400 | EB 1-45 |
| naphth-2-yl-CH₂-O-Lig | Lig-CH₂-Br | 0.029 ± 0.019 | EB 1-87 |
| | Lig-CH₂-S⁺(CH₃)₂ | 1.07 ± 0.1 | EB 1-91 |
| | Lig-CH=CH₂ | 0.44 ± 0.057 | EB 1-81 |

TABLE 1-continued
Compound
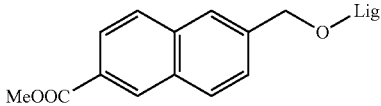
| R' | R" | IC50 for TG2 (μM) | Ref code |
|---|---|---|---|
| 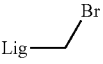 | 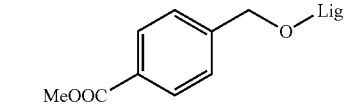 | 0.015 ± 0.007 | EB 1-137 |
| | 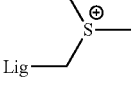 | 1.5 ± 0.4 | EB 1-138 |
| | 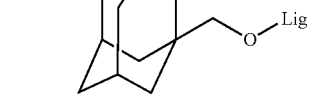 | 2.1 ± 0 | EB 1-136 |
| | 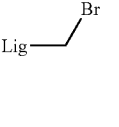 | 0.0067 ± 0.00021 | EB 2-58 |
| 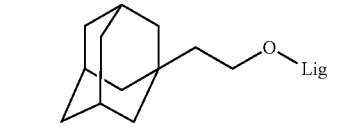 | 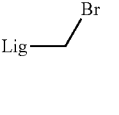 | 3.3 ± 0.3 | EB 1-128 (EB 2-28) |
| | 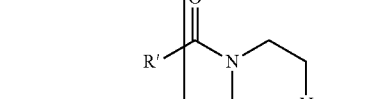 | 6.3 ± 2.9 | EB 1-123 |
| |  | 0.0021 ± 0.0002 | EB 1-111 |
| 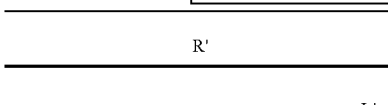 | 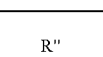 | <1 | EB 1-176 |
| |  | 0.775 ± 0.035 | EB 1-178 |
| | 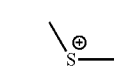 | 1.625 ± 0.035 | EB 1-180 |
|  | 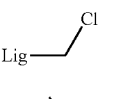 | 0.0063 ± 0.00049 | EB 1-177 |
| |  | 3.15 ± 0.92 | EB 2-30 |

TABLE 1-continued

Compound

[Structure: R'-C(=O)-N(piperazine)N-C(=O)-CH2-NH-C(=O)-R"; Lig]

| R' | R" | IC50 for TG2 (μM) | Ref code |
|---|---|---|---|
|  | Lig—CH=CH2 | 0.9 ± 0.14 | EB 1-181 |
| Adamantyl-Lig | Lig—CH2—Br | 0.0039 ± 0.0004 | EB 2-17 |
|  | Lig—CH2—Cl | 0.0088 ± 0.00035 | EB 2-54 |
|  | Lig—CH2—S⁺(CH3)2 | 0.89 ± 0.2 | EB 2-18 |
|  | Lig—CH=CH2 | 0.125 ± 0.066 | EB 2-16 |

TABLE 2

Compound

[Structure: R'-C(=O)-N(piperazine)N-C(=O)-CH(R")-; Lig]

| R' | R" | IC50 for TG2 (μM) | Ref code |
|---|---|---|---|
| Benzyl-O-Lig | Lig-NH-S(=O)2-CH=CH2 | 1.725 ± 0.11 | EB 2-35 |

TABLE 2-continued

Compound

[Structure: R'-C(=O)-N(piperazine)N-C(=O)-CH(R")-; Lig]

| R' | R" | IC50 for TG2 (μM) | Ref code |
|---|---|---|---|
| Adamantyl-Lig | Lig-NH-S(=O)2-CH=CH2 | 0.88 ± 0.035 | EB 2-32 |

TABLE 3
Compound
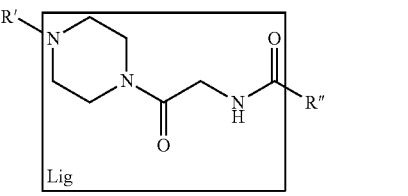
| R' | R'' | IC50 for TG2 (μM) | Ref code |
|---|---|---|---|
| 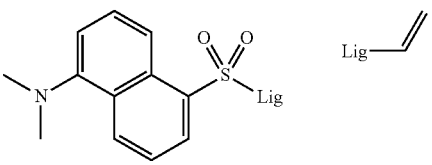 | 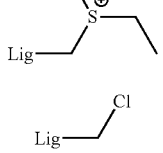 | 0.0061 ± 0.00042 | EB 1-155 |
| | 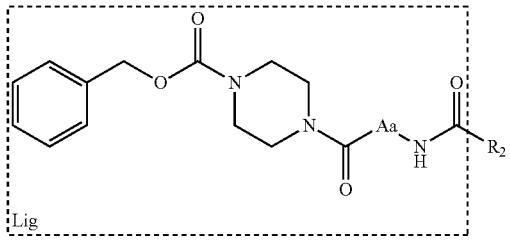 | 038 ± 0.057 | EB 1-159 |
| | 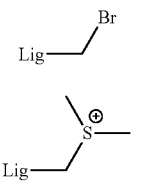 | 0.0059 ± 0.00014 | EB 2-57 |
TABLE 4
Compound
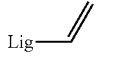
| Aa (amino acid side chain) | R2 | IC50 for TG2 (μM) | Ref code |
|---|---|---|---|
| D-Ala | 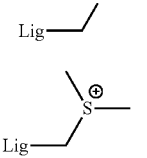 | 0.066 ± 0.001 | EB 1-100 |
| | 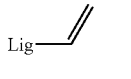 | 6.8 ± 2.0 | EB 1-106 |
| |  | >100 | EB 1-104 |
| L-Ala | 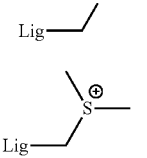 | 0.048 ± 0.006 | EB 1-101 |
| | 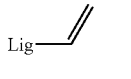 | 0.7 ± 0.3 | EB 1-107 |
| |  | >100 | EB 1-105 |

TABLE 4-continued

Compound

[structure: benzyl carbamate-piperazine-C(O)-NH-CH(Aa)-C(O)-R2, labeled Lig]

| Aa (amino acid side chain) | R2 | IC50 for TG2 (μM) | Ref code |
|---|---|---|---|
| D-Phe | Lig–S⁺(CH3)– | >100 | EB 1-127 |
|  | Lig–CH=CH2 | >100 | EB 1-131 |
| L-Phe | Lig–S⁺(CH3)– | >100 | EB 1-126 |
|  | Lig–CH=CH2 | >100 | EB 1-130 |

Further testing of the effects of exemplary compounds on the activity of other transglutaminases (TG1, TG3 and Factors X111a) revealed a selective inhibition of tissue transglutaminase (TG2), as shown in Table 5.

TABLE 5

| Compound ref code (See Tables 1 to 3) | Estimated IC50 | | |
|---|---|---|---|
|  | TG1 | TG3 | FXIII |
| EB 1-33 | >100 μM | >100 μM | >100 μM |
| EB 1-91 | >100 μM | >100 μM | >100 μM |
| EB 1-81 | >100 μM | >100 μM | >100 μM |
| EB 1-137 | 5 μM | 65 μM | <100 μM |
| EB -138 | >100 μM | <100 μM | <100 μM |
| EB 2-28 | >100 μM | >100 μM | 100 μM |
| EB 1-176 | 2 μM | 25 μM | >100 μM |
| EB 1-178 | >100 μM | >100 μM | >100 μM |
| EB 1-180 | 100 μM | >100 μM | >100 μM |
| EB 2-17 | 1 μM | 70 μM | <100 μM |
| EB 1-136 | >100 μM | >100 μM | >100 μM |
| EB 2-18 | >100 μM | >100 μM | >100 μM |
| EB 2-16 | 2 μM | 11 μM | 30 μM |
| EB 1-155 | 5 μM | >100 μM | >100 μM |
| EB 1-159 | >100 μM | >100 μM | >100 μM |
| EB 1-46 | >100 μM | >100 μM | >100 μM |
| EB 1-181 | 100 μM | >100 μM | >100 μM |
| EB 1-177 | 3 μM | 50 μM | >100 μM |

Example 3—Cell Permeability

This study shows that different inhibitors, depending on the chemistry of the $R_3$ group, show different cell permeabilities.

Methods

HUVEC cells, which have high TG2 expression (A novel extracellular role for tissue transglutaminase in matrix-bound VEGF-mediated angiogenesis. Z. Wang, et al, M. Griffin (2013) *Cell Death and Disease*. Z. Wang Z, et al, M. Griffin. *Cell Death Dis.* 4:e808), were grown in the complete endothelial growth medium EGM. The assay is based on the intracellular activation of TG2 using ionomycin to raise intracellular $Ca^{2+}$ levels and quantifying the intracellular incorporation of biotin cadaverine in the presence and absence of inhibitor. To induce the intracellular TG2 activity, the cells were incubated with fresh growth media with 0.5% FBS containing given 1 μM ionomycin and 1 mM biotin-cadaverine in the presence or absence of 50 uM of TG2 inhibitors. The inhibitors EB 1-155, 1-159, 1-178, 1-180, 2-16 and 2-18 were used in this protocol (see Example 2 above for compound structures). The non-cell permeable inhibitor R281 and cell permeable inhibitor R283 were used as the negative and positive controls, respectively. Intracellular activity was normalised to R281. After a 3 h incubation, the cells were collected in media, pelleted, washed once with PBS and resuspended in homogenization buffer (50 mM Tris-HCl, pH 7.5, 150 mM NaCl, 1 mM EDTA), sonicated on ice. The cell membrane was pelleted at 18,000×g for 15 min and the supernatant (the cytosol fraction) was used for the assay. 50 μg of total protein in 100 μl of the homogenization buffer was loaded to the high protein binding 96-well plate and was incubated at 4° C. for overnight. Following the incubation, 200 μl of blocking buffer (5% BSA, 0.01% Tween 20 in borate saline 100 mM boric acid, 20 mM Na-borate and 0.7 mM NaCl) was used to block the plate at 37° C. for 1 h. Each well was then rinsed 3 times with rinsing buffer (1% BSA, 0.01% Tween 20 in borate saline). 100 μl of extravidin-HRP solution (1:2,500 diluted extravidin-HRP in 3% BSA in 100 mM Tris-HCl, pH 7.4 and 5 mM EDTA) was added to each well and the plates were incubated overnight at 4° C. The plates were then washed four times with 50 mM Tris-HCl, pH 7.4. The signals were detected using OPD substrates and 3N HCl was used to stop the reaction and the reading was performed using the ELISA plate reader at 490 nm. Log P values were calculated as shown in the FIGURE.

Results

The results are shown in FIG. 1.

Discussion

Exemplary TGase inhibitor compounds EB 1-155, 1-180 and 2-16 all have an acrylamide-based warhead, which enables them to enter cells and have greater inhibition of intracellular TG2 activity.

Exemplary TGase inhibitor compounds EB 1-159, 1-178 and 2-18 all have a sulphonamide-based warhead, which prevents them from entering cells and affecting intracellular TG2 activity levels.

Thus, by selecting an appropriate R3 group, the TGase inhibitor compounds of the invention may be targeted either to intracellular or extracellular TG2 enzymes. Extracellular activity is believed to be a more important target in fibrotic/angiogenic disease states. Also preventing inhibitors from entering cells limits intracellular-based off-target/toxicity effects.

Example 4—Selectivity of Inhibitors to Different Transglutaminases

This study demonstrates that different inhibitors exhibit varying selectivity towards different transglutaminases.

Methods

TG transamidation activity and the effect of inhibitors on activity was measured by biotin X-cadaverine incorporation into N,N'-dimethylcasein. After coating 96 well plates with 100 µl of 10 mg/ml N,N'-dimethylcasein in 50 mM Tris-Cl, pH8 at 4° C. over night, plates were washed with TBS-0.05% Tween-20(v/v), pH 7.6 and TBS, pH 7.6, and either 100 µl purified recombinant human TG2 (2 µg/ml Zedira, Germany) or 100 µl purified recombinant human FXIIIa (2 µg/ml Zedira, Germany, preactivated by incubation with 0.01 U bovine thrombin/µg FXIII at room temperature for 30 minutes) in 50 mM Tris-HCl, pH7.4, containing 1 mM DTT, 10 mM $CaCl_2$ and 0.1 µM biotin-cadaverine added into the coated wells containing the appropriate concentration of inhibitor. The reaction was allowed to proceed for 1 h at 37° C. The plate was then washed twice with TBS-Tween-20 (v/v), pH 7.6 and once with TBS, pH 7.6 before being blocked with 100 µl of blocking buffer (3% (w/v) BSA in TBS-Tween, pH 7.6) for 30 min at 37° C. After blocking, the wells were incubated with 100 µl HRP-conjugated ExtrAvidin peroxidase (Sigma-Aldrich, UK) in blocking buffer (1:1,000 dilution) for 1 h at 37° C. After another set of washes, TG2 activity was measured using Sigma Fast OPD, tablets dissolved in 20 ml of distilled $H_2O$. The colour was developed by adding 2.5M $H_2SO_4$ and the absorbance at 490 nm measured using a microplate reader ELx808™. All inhibitors were dissolved in DMSO as a 100 mM solution prior to addition to the assay.

Results

The results are shown in Table 6

TABLE 6

| COMPOUND REF. | TG2 IC50 (µm) | FACTOR XIII IC50 (µm) |
|---|---|---|
| EB 1-126 | >500 | 15.5 ± 6.3 |
| EB 1-127 | >500 | 23.3 ± 5.5 |
| EB 1-131 | >500 | 13.5 ± 4.9 |

N.B. Errors shown are SD.

Discussion

The results demonstrate that the compounds of the invention exhibit different selectivity for different transglutaminases (notably, TG2 and Factor XIII). Whereas compounds EB 1-127, and 1-131 (which comprise a D-Phenylalanine moiety) and EB 1-126 (which comprises an L-Phenylalanine moiety) have negligible inhibitory effect on tissue transglutaminase (TG2), they are all very active against factor XIII. It is believed that the differential activity observed for some of the compounds may be due to the change in amino acids within the inhibitor structural core. These data indicate that the compounds of the invention may be "tuned" to inhibit specific TGs, in order to improve specificity and ultimate therapeutic value.

Example 5—Exemplary Pharmaceutical Formulations

The following examples illustrate pharmaceutical formulations according to the invention in which the active ingredient is a compound of the invention.

Example A: Tablet

| | |
|---|---|
| Active ingredient | 100 mg |
| Lactose | 200 mg |
| Starch | 50 mg |
| Polyvinylpyrrolidone | 5 mg |
| Magnesium stearate | 4 mg |
| | 359 mg |

Tablets are prepared from the foregoing ingredients by wet granulation followed by compression.

Example B: Ophthalmic Solution

| | |
|---|---|
| Active ingredient | 0.5 g |
| Sodium chloride, analytical grade | 0.9 g |
| Thiomersal | 0.001 g |
| Purified water to | 100 ml |
| pH adjusted to | 7.5 |

Example C: Tablet Formulations

The following formulations A and B are prepared by wet granulation of the ingredients with a solution of povidone, followed by addition of magnesium stearate and compression.

Formulation A

| | mg/tablet | mg/tablet |
|---|---|---|
| Active ingredient | 250 | 250 |
| Lactose B.P. | 210 | 26 |
| Povidone B.P. | 15 | 9 |
| Sodium Starch Glycolate | 20 | 12 |
| Magnesium Stearate | 5 | 3 |
| | 500 | 300 |

Formulation B

|  | mg/tablet | mg/tablet |
| --- | --- | --- |
| Active ingredient | 250 | 250 |
| Lactose | 150 | — |
| Avicel PH 101 ® | 60 | 26 |
| Povidone B.P. | 15 | 9 |
| Sodium Starch Glycolate | 20 | 12 |
| Magnesium Stearate | 5 | 3 |
|  | 500 | 300 |

Formulation C

|  | mg/tablet |
| --- | --- |
| Active ingredient | 100 |
| Lactose | 200 |
| Starch | 50 |
| Povidone | 5 |
| Magnesium stearate | 4 |
|  | 359 |

The following formulations, D and E, are prepared by direct compression of the admixed ingredients. The lactose used in formulation E is of the direction compression type.

Formulation D

|  | mg/capsule |
| --- | --- |
| Active Ingredient | 250 |
| Pre-gelatinised Starch NF15 | 150 |
|  | 400 |

Formulation E

|  | mg/capsule |
| --- | --- |
| Active Ingredient | 250 |
| Lactose | 150 |
| Avicel ® | 100 |
|  | 500 |

Formulation F (Controlled Release Formulation)

The formulation is prepared by wet granulation of the ingredients (below) with a solution of povidone followed by the addition of magnesium stearate and compression.

|  | mg/tablet |
| --- | --- |
| Active Ingredient | 500 |
| Hydroxypropylmethylcellulose (Methocel K4M Premium) ® | 112 |
| Lactose B.P. | 53 |
| Povidone B.P.C. | 28 |
| Magnesium Stearate | 7 |
|  | 700 |

Drug release takes place over a period of about 6-8 hours and was complete after 12 hours.

Example D: Capsule Formulations

Formulation A

A capsule formulation is prepared by admixing the ingredients of Formulation D in Example C above and filling into a two-part hard gelatin capsule. Formulation B (infra) is prepared in a similar manner.

Formulation B

|  | mg/capsule |
| --- | --- |
| (a) Active ingredient | 250 |
| (b) Lactose B.P. | 143 |
| (c) Sodium Starch Glycolate | 25 |
| (d) Magnesium Stearate | 2 |
|  | 420 |

Formulation C

|  | mg/capsule |
| --- | --- |
| (a) Active ingredient | 250 |
| (b) Macrogol 4000 BP | 350 |
|  | 600 |

Capsules are prepared by melting the Macrogel 4000 BP, dispersing the active ingredient in the melt and filling the melt into a two-part hard gelatin capsule.

Formulation D

|  | mg/capsule |
| --- | --- |
| Active ingredient | 250 |
| Lecithin | 100 |
| *Arachis* Oil | 100 |
|  | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

|  | mg/capsule |
|---|---|
| (a) Active ingredient | 250 |
| (b) Microcrystalline Cellulose | 125 |
| (c) Lactose BP | 125 |
| (d) Ethyl Cellulose | 13 |
|  | 513 |

Example E: Injectable Formulation

| Active ingredient | 0.200 g |
|---|---|
| Sterile, pyrogen free phosphate buffer (pH 7.0) to | 10 ml |

The active ingredient is dissolved in most of the phosphate buffer (35-40° C.), then made up to volume and filtered through a sterile micropore filter into a sterile 10 ml amber glass vial (type 1) and sealed with sterile closures and overseals.

Example F: Intramuscular Injection

| Active ingredient | 0.20 g |
|---|---|
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

Example G: Syrup Suspension

| Active ingredient | 0.2500 g |
|---|---|
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

Example H: Suppository

|  | mg/suppository |
|---|---|
| Active ingredient (63 μm) | 250 |
| Hard Fat, BP (Witepsol H15 - Dynamit Nobel) | 1770 |
|  | 2020 |

One fifth of the Witepsol H15 is melted in a steam jacketed pan at 45° C maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

Example I: Pessaries

|  | mg/pessary |
|---|---|
| Active ingredient | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

REFERENCES

Bailey, C. D., and G. V. Johnson. 2005. Tissue transglutaminase contributes to disease progression in the R6/2 Huntington's disease mouse model via aggregate-independent mechanisms. *J Neurochem.* 92:83-92.

Collighan, R. J., and M. Griffin. 2009. Transglutaminase 2 cross-linking of matrix proteins: biological significance and medical applications. *Amino Acids.* 36:659-670.

Dafik, L., and C. Khosla. 2011. Dihydroisoxazole analogs for labeling and visualization of catalytically active transglutaminase 2. *Chem Biol.* 18:58-66.

Griffin, M., R. Casadio, and C. M. Bergamini. 2002. Transglutaminases: nature's biological glues. *Biochem J.* 368:377-396.

Griffin, M., A. Mongeot, R. Collighan, R. E. Saint, R. A. Jones, I. G. Coutts, and D. L. Rathbone. 2008. Synthesis of potent water-soluble tissue transglutaminase inhibitors. *Bioorg Med Chem Lett.* 18:5559-5562.

Halim, D., K. Caron, and J. W. Keillor. 2007. Synthesis and evaluation of peptidic maleimides as transglutaminase inhibitors. *Bioorg Med Chem Lett.* 17:305-308.

Han, B.-G., J.-W. Cho, Y. D. Cho, K.-C. Jeong, S.-Y. Kim, and B. I. Lee. 2010. Crystal structure of human transglutaminase 2 in complex with adenosine triphosphate. *International Journal of Biological Macromolecules.* 47:190-195.

Hasegawa, G., M. Suwa, Y. Ichikawa, T. Ohtsuka, S. Kumagai, M. Kikuchi, Y. Sato, and Y. Saito. 2003. A novel function of tissue-type transglutaminase: protein disulphide isomerase. *Biochem. J.* 373:793-803.

Huang, L., J. L. Haylor, Z. Hau, R. A. Jones, M. E. Vickers, B. Wagner, M. Griffin, R. E. Saint, I. G. Coutts, A. M. El Nahas, and T. S. Johnson. 2009. Transglutaminase inhibition ameliorates experimental diabetic nephropathy. *Kidney Int.* 76:383-394.

Johnson, T., M. Fisher, J. Naylor, Z. Hau, N. Skill, R. Jones, R. Saint, I. Coutts, A. El Nahas, and M. Griffin. 2008. Transglutaminase inhibition ameliorates tissue scarring and fibrosis: experience in a kidney model. *J Am Soc.* 14:2052.

Klock, C., X. Jin, K. Choi, C. Khosla, P. B. Madrid, A. Spencer, B. C. Raimundo, P. Boardman, G. Lanza, and J. H. Griffin. 2011. Acylideneoxoindoles: A new class of reversible inhibitors of human transglutaminase 2. *Bioorg Med Chem Lett.* 21:2692-2696.

Lindemann, I., A. Heine, and G. Klebe. 2012. Transglutaminase 2 in complex with a novel inhibitor. *PDB codes:* 3S3P, 3S3S, 3S3J.

Liu, S., R. A. Cerione, and J. Clardy. 2002. Structural basis for the guanine nucleotide-binding activity of tissue transglutaminase and its regulation of transamidation activity. *Proc Natl Acad Sci USA.* 99:2743-2747.

Mastroberardino, P. G., C. Iannicola, R. Nardacci, F. Bernassola, V. De Laurenzi, G. Melino, S. Moreno, F. Pavone, S. Oliverio, L. Fesus, and M. Piacentini. 2002. 'Tissue' transglutaminase ablation reduces neuronal death and prolongs survival in a mouse model of Huntington's disease. *Cell Death Differ.* 9:873-880.

Mishra, S., and L. J. Murphy. 2004. Tissue transglutaminase has intrinsic kinase activity: identification of transglutaminase 2 as an insulin-like growth factor-binding protein-3 kinase. *J Biol Chem.* 279:23863-23868.

Nakaoka, H., D. M. Perez, K. J. Baek, T. Das, A. Husain, K. Misono, M. J. Im, and R. M. Graham. 1994. Gh: a GTP-binding protein with transglutaminase activity and receptor signaling function. *Science.* 264:1593-1596.

Pardin, C., S. M. Gillet, and J. W. Keillor. 2006. Synthesis and evaluation of peptidic irreversible inhibitors of tissue transglutaminase. *Bioorg Med Chem.* 14:8379-8385.

Pardin, C., J. N. Pelletier, W. D. Lubell, and J. W. Keillor. 2008a. Cinnamoyl inhibitors of tissue transglutaminase. *J Org Chem.* 73:5766-5775.

Pardin, C., I. Roy, W. D. Lubell, and J. W. Keillor. 2008b. Reversible and competitive cinnamoyl triazole inhibitors of tissue transglutaminase. *Chem Biol Drug Des.* 72:189-196.

Pinkas, D. M., P. Strop, A. T. Brunger, and C. Khosla. 2007. Transglutaminase 2 undergoes a large conformational change upon activation. *PLoS Biol.* 5:e327.

Prime, M. E., O. A. Andersen, J. J. Barker, M. A. Brooks, R. K. Cheng, I. Toogood-Johnson, S. M. Courtney, F. A. Brookfield, C. J. Yarnold, R. W. Marston, P. D. Johnson, S. F. Johnsen, J. J. Palfrey, D. Vaidya, S. Erfan, O. Ichihara, B. Felicetti, S. Palan, A. Pedret-Dunn, S. Schaertl, I. Sternberger, A. Ebneth, A. Scheel, D. Winkler, L. Toledo-Sherman, M. Beconi, D. Macdonald, I. Munoz-Sanjuan, C. Dominguez, and J. Wityak. 2012. Discovery and structure-activity relationship of potent and selective covalent inhibitors of transglutaminase 2 for Huntington's disease. *J Med Chem.* 55:1021-1046.

Verderio, E. A., T. Johnson, and M. Griffin. 2004. Tissue transglutaminase in normal and abnormal wound healing: review article. *Amino Acids.* 26:387-404.

The invention claimed is:

1. A method of treating a disease or condition in a subject in need thereof, wherein said disease or condition is characterized by abnormal levels of transglutaminase activity, wherein said method comprises administering to said subject a compound of Formula I

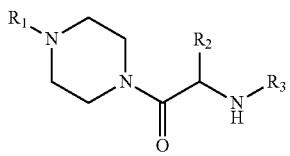

Formula I wherein $R_1$ is selected from the group consisting of $R_4C(O)$—, $R_5OC(O)$— and $R_6S(O)_2$— wherein $R_4$ is a lower alkyl group $R_5$ and $R_6$ are selected from the group consisting of heterocyclic groups, aralkyl groups and lower alkyl groups $R_2$ is —H; and $R_3$ is selected from the group consisting of —C(O)$R_7$ and —S(O)$_2$CHCH$_2$ wherein $R_7$ is selected from the group consisting of alkyl halide, alkylene dialkyl sulfonium, and lower alkenyl or a pharmaceutically and/or veterinarily acceptable salt or solvate thereof, wherein said disease or condition is selected from the group consisting of fibrosis, scarring, neurodegenerative diseases, autoimmune diseases, thrombosis, proliferative disorders, AIDS, psoriasis, and inflammation.

2. The method according to claim 1 wherein $R_1$ is $R_4C(O)$—.

3. The method according to claim 2 wherein $R_4$ is

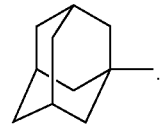

4. The method according to claim 1 wherein $R_1$ is $R_5OC(O)$—.

5. The method according to claim 4 wherein $R_5$ comprises a phenyl or naphthyl group, linked to the ester moiety of $R_5OC(O)$— by a straight chain $C_{1-6}$ alkylene group.

6. The method according to claim 1 wherein $R_5$ is

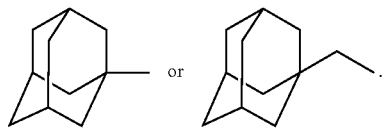

7. The method according to claim 1 wherein $R_1$ is $R_6S(O)_2$—.

8. The method according to claim 7 wherein $R_6$ is an aralkyl group and comprises a phenyl or naphthyl group.

9. The method according to claim 1 wherein $R_7$ is an alkyl halide group.

10. The method according to claim 1 wherein $R_7$ is an alkylene dialkyl sulfonium group.

11. The method according to claim 1 wherein $R_7$ is a lower alkenyl group.

12. The method according to claim 1 wherein $R_3$ is —S(O)$_2$CHCH$_2$.

13. The method according to claim 1, wherein the compound is selected from the group consisting of:

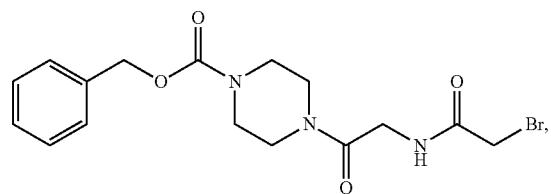

-continued

EB 1-111
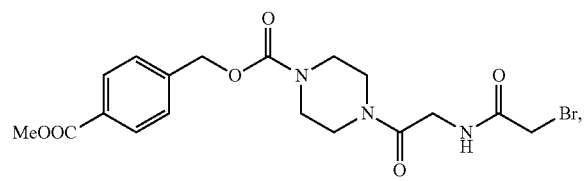

EB 1-176
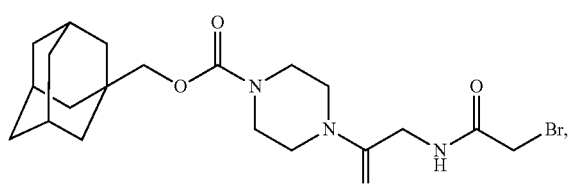

EB 1-178
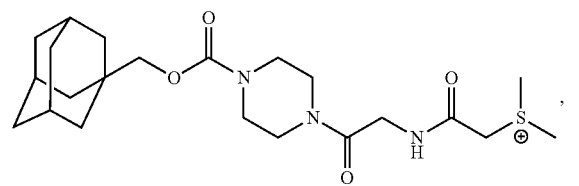

EB 1-180
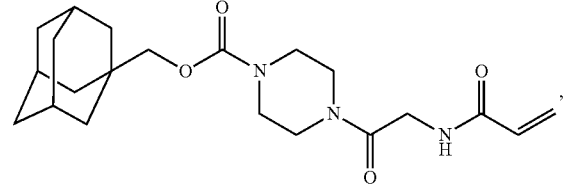

EB 1-177
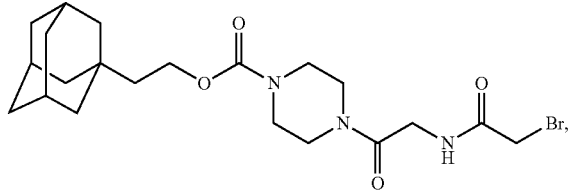

EB 2-30
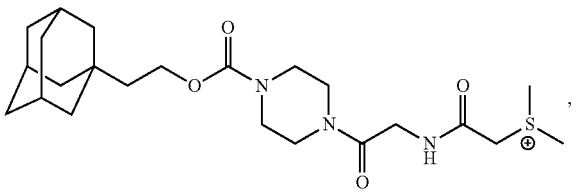

EB 1-181
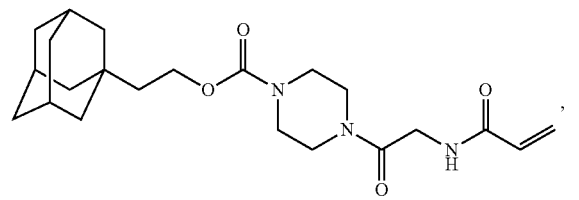

-continued

EB 2-17
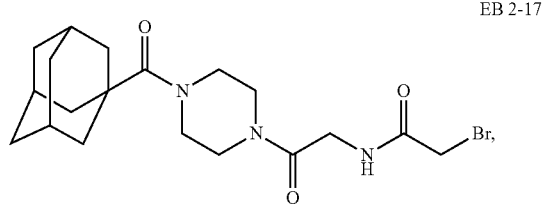

EB 2-54
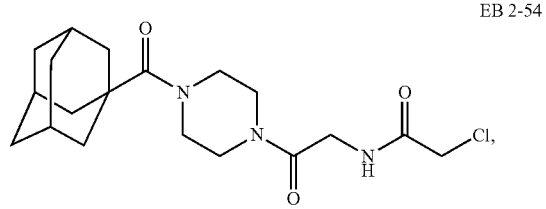

EB 2-18
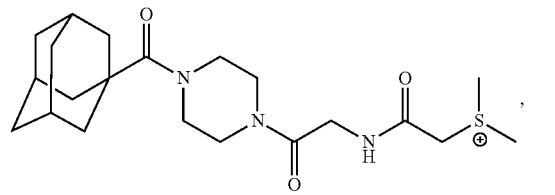

EB 2-16
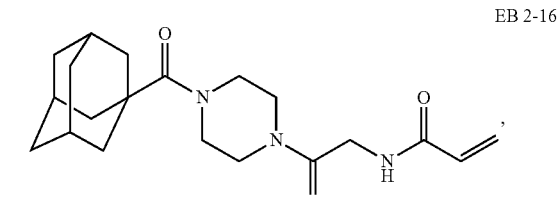

EB 2-35
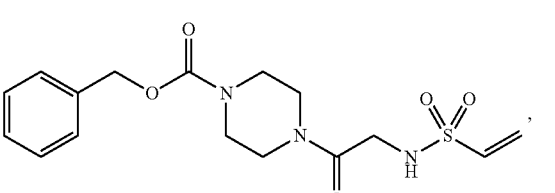

and

EB 2-32
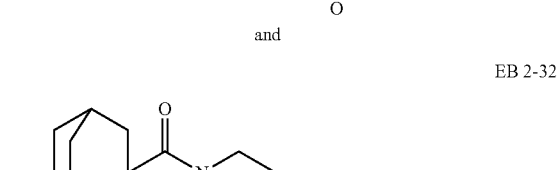

14. The method according to claim 1 wherein the subject has a disease or condition selected from the group consisting of cystic fibrosis, scarring, Alzheimer's disease, Huntington's disease, Parkinson's disease, multiple sclerosis, coeliac disease, thrombosis, cancers, AIDS, psoriasis, and chronic inflammatory disease.

15. The method according to claim 1 wherein the compound is administered in an amount sufficient to inhibit, at least in part, tissue transglutaminase-mediated protein modification.

16. The method according to claim 1 wherein the compound is administered in an amount sufficient to inhibit, at least in part, angiogenesis.

17. The method according to claim 1, wherein said disease or disorder is pathological angiogenesis.

18. The method according to claim 1, wherein said lower alkenyl is a $C_2$-$C_5$ alkenyl.

19. A method of treating a disease or condition in a subject in need thereof, wherein said disease or condition is characterized by abnormal levels of transglutaminase activity, wherein said method comprises administering to said subject a compound of Formula I

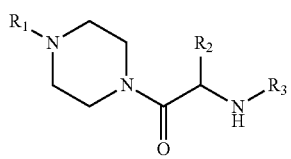

Formula I wherein
  $R_1$ is $R_6S(O)_2$—
    wherein
      $R_6$ is an optionally substituted phenyl or naphthyl, wherein the phenyl or naphthyl is optionally substituted with one or more substituents selected from the group consisting of fluoro, cyano, nitro, lower alkyl, —OR, —C(O)R, —C(O)OR, —C(O)NRR' and NRR', wherein R and R' are lower alkyls
  $R_2$ is —H; and
  $R_3$ is selected from the group consisting of —C(O)$R_7$ and —S(O)$_2$CHCH$_2$
    wherein
      $R_7$ is selected from the group consisting of alkyl halide, alkylene dialkyl sulfonium, and lower alkenyl
or a pharmaceutically and/or veterinarily acceptable salt or solvate thereof,
    wherein said disease or condition is selected from the group consisting of fibrosis, scarring, neurodegenerative diseases, autoimmune diseases, thrombosis, proliferative disorders, AIDS, psoriasis, and inflammation.

20. The method according to claim 19, wherein $R_1$ is dansyl.

21. The method according to claim 19, wherein the compound is selected from the group consisting of:

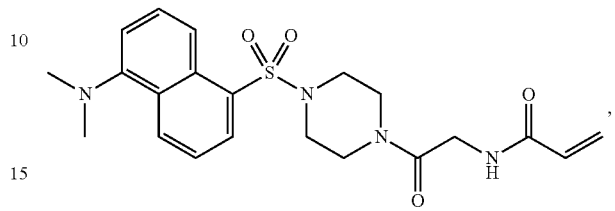

EB 1-555

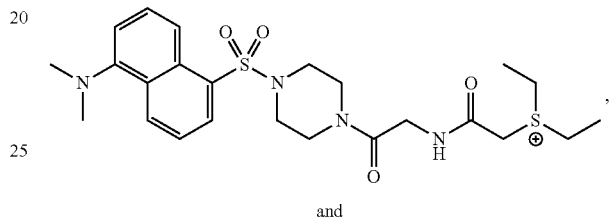

EB 1-159 and

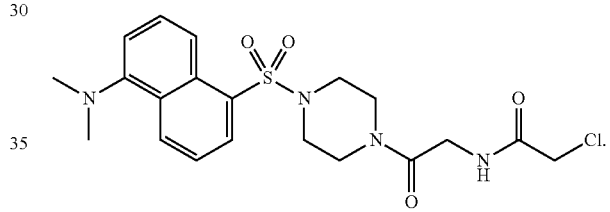

EB 2-57

\* \* \* \* \*